US005798355A

United States Patent [19]

Steiner et al.

[11] Patent Number: 5,798,355

[45] Date of Patent: *Aug. 25, 1998

[54] INHIBITORS OF ROTAMASE ENZYME ACTIVITY

[75] Inventors: Joseph P. Steiner, Hampstead; Solomon Snyder, Baltimore; Gregory S. Hamilton, Catonsville; Ted Dawson, Baltimore, all of Md.

[73] Assignees: GPI NIL Holdings, Inc., Wilmington, Del.; Johns Hopkins University School of Medicine, Baltimore, Md.

[*] Notice: The term of this patent shall not extend beyond the expiration date of Pat. No. 5,696,135.

[21] Appl. No.: 474,072

[22] Filed: Jun. 7, 1995

[51] Int. Cl.$^6$ .................. A61K 31/50; A61K 31/44; A61K 31/445

[52] U.S. Cl. .................. 514/248; 514/293; 514/300; 514/302; 514/248; 514/326; 514/330

[58] Field of Search .................. 514/248, 293, 514/300, 318, 326, 330, 302

[56] References Cited

U.S. PATENT DOCUMENTS

| | | |
|---|---|---|
| 4,310,461 | 1/1982 | Krapcho et al. |
| 4,390,695 | 6/1983 | Krapcho et al. |
| 4,531,964 | 7/1985 | Shimano et al. |
| 4,578,474 | 3/1986 | Krapcho et al. |
| 4,593,102 | 6/1986 | Shanklin, Jr. |
| 5,192,773 | 3/1993 | Armistead et al. ............ 514/315 |
| 5,330,993 | 7/1994 | Armistead et al. ............ 514/330 |
| 5,385,918 | 1/1995 | Connell et al. ............ 514/330 |
| 5,414,083 | 5/1995 | Hackl et al. |
| 5,504,197 | 4/1996 | Schubert et al. ............ 536/23.5 |
| 5,516,797 | 5/1996 | Armistead et al. |
| 5,543,423 | 8/1996 | Zelle et al. |

FOREIGN PATENT DOCUMENTS

| | | |
|---|---|---|
| 0564924A2 | 5/1992 | European Pat. Off. |
| WO9535308 | 12/1985 | WIPO |
| WO9200278 | 1/1992 | WIPO |
| WO9204370 | 3/1992 | WIPO |
| WO9216501 | 10/1992 | WIPO |
| WO9219593 | 11/1992 | WIPO |
| WO9219745 | 11/1992 | WIPO |
| WO9221313 | 12/1992 | WIPO |
| WO9307269 | 4/1993 | WIPO |
| WO9323548 | 11/1993 | WIPO |
| WO9405639 | 3/1994 | WIPO |
| WO9407858 | 4/1994 | WIPO |
| WO9413629 | 6/1994 | WIPO |
| WO9524385 | 9/1995 | WIPO |
| WO9526337 | 10/1995 | WIPO |
| WO9535367 | 12/1995 | WIPO |
| WO9615101 | 5/1996 | WIPO |
| WO96/3318 | 10/1996 | WIPO |
| WO96/36630 | 11/1996 | WIPO |
| WO96/41609 | 12/1996 | WIPO |

OTHER PUBLICATIONS

Dragovich et al., "Structured–Based Design of Novel, Urea–Containing FKBP12 Inhibitors." J. Med. Chem., 1996, 39, 1872–1884.

Gold et al., The Immunosuppressant FK506 Increases the Rate of Axonal Regeneration in Rat Sciatic Nerve. The Journal of Neuroscience, 1995, 15(11), 7509–7516.

Gold et al, "The Immunosuppressant FK506 increases functional recovery and nerve regeneration following peripheral nerve injury," Restorative Neurology and Neuroscience, 1994, 6, 287–296.

Lyons et al., "Immunosuppressant FK506 promotes neurite outgrowth in culture of PC12 cells and sensory ganglia," Proc. Natl. Acad. Sci. USA, 1994, 91, 3191–3195.

Gold, et al. "Multiple signals underlie the anatomy–induced up–regulation of c–JUN in adult sensory neurons," Neuroscience Letters 176, 1994, 123–127.

Gold et al., "Regulation of the transcription factor c–JUN by *nerve growth* factor in adult sensory neurons," Neuroscience Letters 154, 1993, 129–133.

Schreiber, Chemical Abstract, vol. 123:275997, 1995.
Rinehart, Chemical Abstract, vol. 121:887, 1994.
Takeuchi, Checmical Abstract, vol. 122:131140, 1994.
Thaisrivongs, Chemical Abstract, vol. 117:112083, 1992.
Yamada, Chemical Abstract, vol. 117:212981, 1992.
Someno, Chemical Abstract, vol. 116:236174, 1992.
Schreiber, Chemical Abstract, vol. 116:34554, 1991.
Rinehart, Chemical Abstract, vol. 115:248086, 1991.
Baader, Chemical Abstract, vol. 116.129617, 1991.
Prasit, Chemical Abstract, vol. 115:207870, 1991.
Askin, Chemical Abstract, vol. 114:228633, 1991.
Jones, Chemical Abstract, vol. 114:81436, 1990.
Takeuchi, Chemical Abstract, vol. 115:90647, 1990.
Dreyer, Chemical Abstract, vol. 113:153045, 1990.
Bieringer, Chemical Abstract, vol. 113:226420, 1990.
Askin, Chemical Abstract, vol. 114:23615, 1990.
Goulet, Chemical Abstract, vol. 114:81347, 1990.
Jones, Chemical Abstract, vol. 112:235036, 1990.
Jones, Chemical Abstract, vol. 113:23463, 1990.
Rao, Chemical Abstract, vol. 113:191007, 1990.
Waldmann, Chemical Abstract, vol. 114:82457, 1990.
Finberg, Chemical Abstract, vol. 113:184256, 1990.
Gold, Chemical Abstract, vol. 111:195414, 1989.
Gold, Chemical Abstract, vol. 111:97735, 1989.
Matsuo, Chemical Abstract, vol. 112:158977, 1989.
Goodfellow, Chemical Abstract, vol. 111:93084, 1989.
Wasserman, Chemical Abstract, vol. 112:35516, 1989.
Wasserman, Chemical Abstract, vol. 111:57366, 1989.
Askin, Chemical Abstract, vol. 111:232396, 1989.

(List continued on next page.)

*Primary Examiner*—William R. A. Jarvis
*Attorney, Agent, or Firm*—Gary M. Nath; Todd L. Juneau; Nath & Associates

[57] ABSTRACT

This invention relates to the method of using neurotrophic pipecolic acid derivative compounds having an affinity for FKBP-type immunophilins as inhibitors of the enzyme activity associated with immunophilin proteins, and particularly inhibitors of peptidyl-prolyl isomerase or rotamase enzyme activity to stimulate or promote neuronal growth or regeneration.

34 Claims, 18 Drawing Sheets

OTHER PUBLICATIONS

Faelth, Chemical Abstract, vol. 112:97901, 1989.
Boulmedais, Chemical Abstract, vol. 112:44174, 1989.
Coleman, Chemical Abstract, vol. 112:7219, 1989.
Egbertson, Chemical Abstract, vol. 110:57371, 1989.
De Luca, Chemical Abstract, vol. 111:23387, 1988.
Arzeno, Chemical Abstract, vol. 110:8697, 1988.
Williams, Chemical Abstract, vol. 109:170092, 1988.
Kocienski, Chemical Abstract, vol. 110:212441, 1988.
Tanaka, Chemical Abstract, vol. 107:175741, 1987.
Soai, Chemical Abstract, vol. 108:38323, 1987.
Munegumi, Chemical Abstract, vol. 107:218023, 1987.
Gavras, Chemical Abstract, vol. 105:6828, 1986.
Nestor, Chemical Abstract, vol. 106:214389, 1986.
Gante, Chemical Abstract, vol. 107:97131, 1986.
Soai, Chemical Abstract, vol. 105:134309, 1986.
Soai, Chemical Abstract, vol. 107:197713, 1986.
Soai, Chemical Abstract, vol. 103:70915, 1985.
Soai, Chemical Abstract, vol. 102, 78344, 1984.
Harris, Chemical Abstract, vol. 99:88574, 1983.
Smith, Chemical Abstract, vol. 100:175294, 1983.
Ryan, Chemical Abstract, vol. 100:103897, 1983.
Soai, Chemical Abstract, vol. 99:105651, 1983.
Neustadt, Chemical Abstract, vol. 97:216730, 1982.
Ryan, Chemical Abstract, vol. 97:163506, 1982.
Colombo, Chemical Abstract, vol. 98:161133, 1982.
Soai, Chemical Abstract, vol. 98:88478, 1982.
Patchett, Chemical Abstract, vol. 95:25634, 1980.
Bender, Chemical Abstract, vol. 89:128811, 1978.
Steglich, Chemical Abstract, vol. 89:214864, 1978.
Cushman, Chemical Abstract, vol. 88:18091, 1977.
Steglich, Chemical Abstract, vol. 85:108966, 1976.
Bycroft, Chemical Abstract, vol. 84:106021, 1975.
Marshall, Chemical Abstract, vol. 83:178991, 1975.
Haeusler, Chemical Abstract, vol. 80:108833, 1974.
Hearn, Chemical Abstract, vol. 68:22217, 1967.
Chakraborty, Chemical Abstract, vol. 125:115111, 1996.
Shu, Chemical Abstract, vol. 124:342921, 1996.
Chakraborty, Chemical Abstract, vol. 124:290256, 1996.
Slee, Chemical Abstract, vol. 124:105570, 1995.
Tatlock, Chemical Abstract, vol. 124:86677, 1995.
Teague, Chemical Abstract, vol. 124:29474, 1995.
Stocks, Chemical Abstract, vo. 124:290735, 1995.
Wang, Chemical Abstract, vol. 123:275108, 1995.
Nicolaou, Chemical Abstract, vol. 123:285602, 1995.
Armistead, Chemical Abstract, vol. 123:217939, 1995.
Luengo, Chemical Abstract, vol. 123:187705, 1995.
Furber, Chemical Abstract, vol. 123:47577, 1995.
Chakraborty, Chemical Abstract, vol. 123:74408, 1995.
Wang, Chemical Abstract, vol. 123:74101, 1995.
Smith, Chemical Abstract, vol. 123:55541, 1995.
Baumann, Chemical Abstract, vol. 122:314327, 1995.
Nelson, Chemical Abstract, vol. 122:80964, 1994.
Caffrey, Chemical Abstract, vol. 123:82999, 1994.
Birkenshaw, Chemical Abstract, vol. 122:187213, 1994.
Hauske, Chemical Abstract, vol. 122L45705, 1994.
Stocks, Chemical Abstract, vol. 121:271263, 1994.
Teague, Chemical Abstract, vol. 121:255492, 1994.
Mashkovskii, Chemical Abstract, vol. 121:212542, 1993.
Ranganathan, Chemical Abstract, vol. 121:205990, 1994.
Wang, Chemical Abstract, vol. 121:170041, 1994.
Baader, Chemical Abstract, vol. 121:102790, 1994.
Luengo, Chemical Abstract, vol. 121:49600, 1994.
Holt, Chemical Abstract, vol. 121:224, 1994.
Teague, Chemical Abstract, vol. 121:215, 1993.
Karle, Chemical Abstract, vol. 120:324190, 1994.
Skotnicki, Chemical Abstract, vol. 120:323021, 1994.
Skotnicki, Chemical Abstract, vol. 120:323020, 1994.
Holt, Chemical Abstract, vol. 120:323019, 1993.
Rao, Chemical Abstract, vol. 120:323003, 1993.
Yamashita, Chemical Abstract, vol. 120:315168, 1994.
Andrus, Chemical Abstract, vol. 120:134101, 1993.
Holt, Chemical Abstract, vol. 120:134099, 1993.
Luengo, Chemical Abstract, vol. 120:54365, 1993.
Steffan, Chemical Abstract, vol. 120:54360, 1993.
Nicolaou, Chemical Abstract, vol. 119:270859, 1993.
Hayward, Chemical Abstract, vol. 119:249751, 1993.
Pattenden, Chemical Abstract, vol. 119:95189, 1993.
Yohannes, Chemical Abstract, vol. 119:49108, 1993.
Furber, Chemical Abstract, vol. 119:27877, 1993.
Luengo, Chemical Abstract, vol. 118:233723, 1993.
Ranganathan, Chemical Abstract, vol. 118:213513, 1993.
Yohannes, Chemical Abstract, vol. 118:147360, 1992.
Hauske, Chemical Abstract, vol. 118:22591, 1992.
Cunliffe, Chemical Abstract, vol. 117:49183, 1992.
Goulet, Chemical Abstract, vol. 116:193989, 1991.
Waldmann, Chemical Abstract, vol. 116:491997, 1991.
Goulet, Chemical Abstract, vol. 115:255882, 1991.
Krit, Chemical Abstract, vol. 115:232847, 1991.
Rao, Chemical Abstract, vol. 114:247016, 1991.
Fisher, Chemical Abstract, vol. 114:228608, 1991.
Linde, Chemical Abstract, vol. 114:206955, 1991.
Harding, M.W., et al. "A receptor for the immunosuppressant FK506 is a *cis–trans* peptidyl–prolyl isomerase," Nature Lett., 1989, 341, 758–60.
Ponticelli, Claudio, "Treatment of the Nephrotic Syndrome with Cyclosporin A," J. of Autoimmunity, 1992, 5, 315.
Tindall, Richard S.A., "Immunointervention with Cyclosporin A in Autoimmune Neurological Disorders," J. of Autoimmunity, 1992, 5, 301.
Tugwell, Peter, "Cyclosporin in the Treatment of Rheumatoid Arthritis," J. of Autoimmunity, 1992, 5, 231–40.
Fry, Lionel, "Psoriasis: Immunopathology and Long–term treatment with Cyclosporin," J. of Autoimmunity, 1992, 5, 277–83.
Feutren, Gilles, "The Optimal use of Cyclosporin A in Autoimmune Diseases," J. of Autoimmunity, 1992, 5, 183–95.
Kaczmar, et al., Makromol. Chem., 1976, 177, 1981–9.
Steiner, Joseph P. et al., "High brain densities of the immunophilin FKBP colocalized with calcineurin," Nature Lett., 1992, 358, 584–7.
Dawson, Ted M. et al., "Immunosuppressant FK506 enhances phosphorylation of nitric oxide synthase and protects against glutamate neurotoxicity," Proc. Natl. Acad. Sci. USA, 1993, 90, 9808–12.
Blaschke et al., Chemical Abstracts, 1974, 85, 78405k.
Caufield, Craig E. and Musser, John H., *Annual Reports in Medicinal Chemistry*, Johns (Ed.), Academic Press, Inc., Chapter 21, 195–204, 1989.
Effenberger F. et al., "Diastereoselective addition of benzenesulfenyl chloride to 1–acryloylproline esters," Chemical Abstracts, 1989, 10, 778–9.
Nakatsuta, M. et al. "Total Synthesis of FK506 and an FKBP Probe Reagent, ($C_8$, $C_9$–$^{13}C_2$) –FK–506," J. Am. Chem. Soc., 1990, 112 (14), 5583–90.

Dawson, T.M. et al., "The immunophilins, FK506 Binding Protein and Cyclophilin, are Discretely Localized in the Brain: Relationship to Calcineurin," Neuroscience, 1994, 62(2), 569–80.

Cameron, Andrew et al., "Immunophilin FK506 binding protein associated with inositol 1,4,5–trisphosphate receptor modulates calcium flux," Proc. Natl. Acad. Sci. USA, 1995, 92, 1784–88.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Lyons, W. Ernest et al., "Neuronal Regeneration Enhances the Expression of the Immunophilin FKBP–12," The Journal of Neuroscience, 1995, 15, 2985–94.

Hayward, C.M., et al., "An application of the Suarez reaction to the regiospecific synthesis of the $C_{28}$–$C_{42}$ segment of rapamycin," 1993, 3989–92.

Hovarth, R. et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Kino, Toru et al., "FK–506, A novel immunosuppressant isolated from A Streptomyces," J. of Antibiotics, 1987, 40(9), 1249–55.

Burbaum, Chemical Abstract, vol. 123:170197, 1995.
Burbaum, Chemical Abstract, vol. 121:109686, 1994.
Armistead, Chemical Abstract, vol. 121:170549, 1994.
Armistead, Chemical Abstract, vol. 117:131071, 1992.
Holt, Chemical Abstract, vol. 125:86501, 1996.
Smith, Chemical Abstract, vol. 125:114400, 1996.
Baker, Chemical Abstract, vol. 123:313433, 1995.
Camaggi, Chemical Abstract, vol. 124:30417, 1995.
Armistead, Chemical Abstract, vol. 122:55896, 1994.
Skotnicki, Chemical Abstract, vol. 120:54388, 1993.
Luethy, Chemical Abstract, vol. 123:313999, 1993.
Frenette, Chemical Abstract, vol. 121:35325, 1993.
Krantz, Chemical Abstract, vol. 120:245776, 1993.
Ito, Chemical Abstract, vol. 120:245780, 1993.
Casini, Chemical Abstract, vol. 120:270095, 1993.
Armistead, Chemical Abstract, vol. 119:95338, 1992.
Goulet, Chemical Abstract, vol. 118:80723, 1992.
Kasahara, Chemical Abstract, vol. 117:48221, 1992.
Long, Chemical Abstract, vol. 118:169119, 1992.
Lyons et al, Chemical Abstracts, vol. 120, No. 25, 1994, abstract No. 315423r, p. 48.
Sharkey et al, Chemical Abstracts, vol. 121, No. 19, 1994, abstract No. 221398e.

Kelly et al, Chemical Abstracts, vol. 122, No. 10, 1995, abstract No. 114965m, p. 659.

Hauske, James R. et al., "Design and Synthesis of Novel FKBP Inhibitors," J. Med. Chem., 1992, 35, pp. 4284–4296.

Holt, Dennis A. et al., "Structure–Activity Studies of Nonmacrocylic Rapamycin Derivatives," Bioorganic & Medical Chemistry Letters, 1993, vol. 3, No.10, pp. 1977–1980.

Yamashita, Dennis S. et al., "Design Synthesis and Evaluuation of Dual Domain FKBP Ligands," Bioorganic & Medicinal Chemistry Letters, 1994, vol. 4, No. 2 pp. 325–328.

Teague, Simon J. et al., "Synthesis and Study of a Non Macrocyclic FK506 Derivative," Bioorganic & Medical Chemistry Letters, 1994, vol. 4, No. 13, pp. 1581–1584.

Luengo, Juan I. et al., "Synthesis and Structure–Activity Relationships of Macrocyclic FKBP Ligands," Bioorganic & Medicinal Chemistry Letters, 1994, vol. 4, No. 2, p. 321–324.

Holt, Dennis A. et al., "Structure–Activity Studies of Synthetic FKBP Ligands as Peptidyl–Prolyl Isomerase Inhibitors," Bioorganic & Medicinal Chemistry Letters, 1994, vol. 4, No. 2, pp. 315–320.

Teague, Simon J. et al., "The Affinity of the Excised Binding Dommain of FK–506 for the Immunophilin FKBP12," Bioorganic & Medicinal Chemistry Letters, 1993, vol. 3, No. 10, pp. 1947–1950.

Caffrey, Moya V. et al., "Synthesis and Evaluation of Dual Domain Macrocyclic FKBP12 Ligands," Bioorganic & Medicinal Chemistry Letters, 1994, vol. 4, No. 21, pp. 2507–2510.

Birkenshaw, Timothy N. et al., "Synthetic FKBP12 Ligands. Design and Synthesis of Pyranose Replacements," Bioorganic & Medicinal Chemistry Letters, 1994, vol. 4, No. 21, pp. 2501–2506.

Holt, Dennis A. et al., "Design, Synthesis, and Kinetic Evaluation of High–Affinity FKBP Ligands and the X–ray Crystal Structures of Their Complexes with FKB912," J. Am. Chem. Soc., 1993, 115, pp. 9925–9938.

Wang, Gary T. et al., "Synthesis and FKBP Binding of Small Molecule Mimics of the Tricarbonyl Region of FK506," Bioorganic & Medicinal Chemistry Letters, 1994, vol. 4, No. 9, pp. 1161–1166.

Snyder, Solomon H. and Sabatini, David M., Immunophilins and the Nervous Systems, Nature Medicine, 1995 vol. 1, No. 1, pp. 32–37.

Stocks, Michael J. et al., "The Contribution to Binding of the Pyranoside Substitutents in the Excised Binding Domain of FK–506," Bioorganic & Medicinal Chemistry Letters, 1994, vol. 4, No. 12, pp. 1457–1460.

FIG. 3A
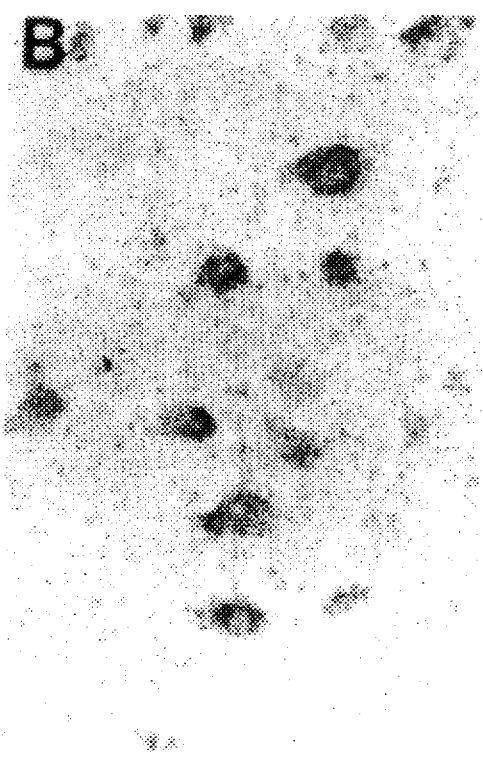
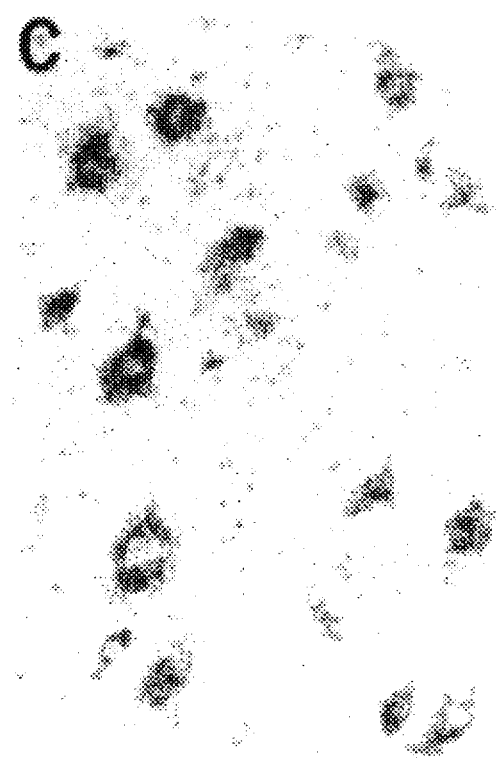
FIG. 3B
FIG. 3C

FKBP IN SITU

Control

FKBP IN SITU

Crush

FK-506 AUTORAD

Control

FK-506 AUTORAD

Crush

FIG. 13A  FIG. 13B  FIG. 13C
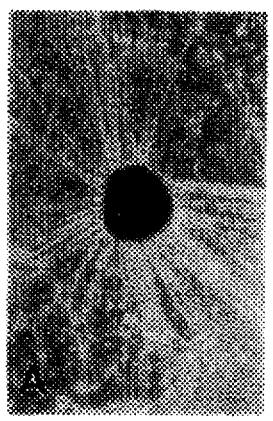 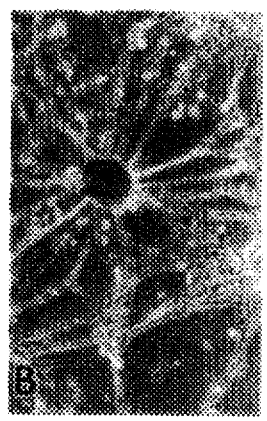 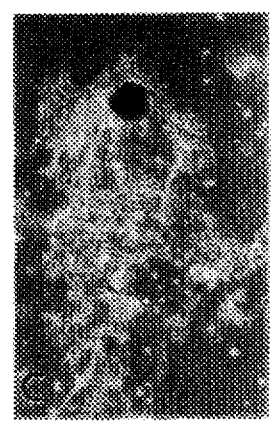
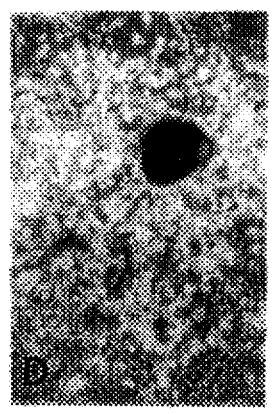 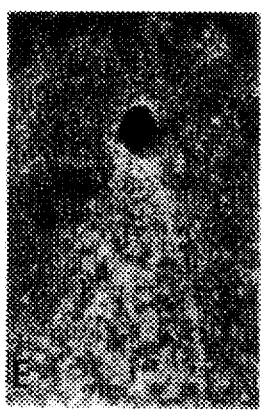 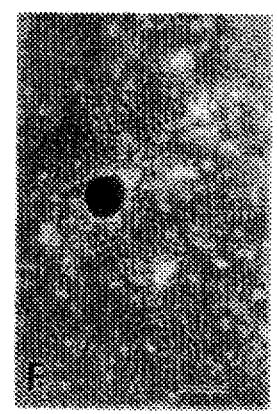
FIG. 13D  FIG. 13E  FIG. 13F

INHIBITORS OF ROTAMASE ENZYME ACTIVITY

BACKGROUND OF THE INVENTION

1. Field of the Invention

This invention relates to the method of using neurotrophic pipecolic acid derivative compounds having an affinity for FKBP-type immunophilins as inhibitors of the enzyme activity associated with immunophilin proteins, and particularly inhibitors of peptidyl-prolyl isomerase or rotamase enzyme activity.

2. Description of the Prior Art

The term immunophilin refers to a number of proteins that serve as receptors for the principal immunosuppressant drugs, cyclosporin A (CsA), FK506, and rapamycin. Known classes of immunophilins are cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Schreiber et al. *Science* 1990, 250, 556–559. Instead immunosuppression appears to stem from the formulation of a complex of immunosuppressant drugs and immunophilins. It has been shown that the immunophilin-drug complexes interact with ternary protein targets as their mode of action. Schreiber et al., *Cell* 1991, 66, 807–815. In the case of FKBP-FK506 and FKBP-CsA, the drug-immunophilin complexes bind to the enzyme calcineurin, inhibiting T-cell receptor signalling leading to T-cell proliferation. Similarly, the complex of rapamycin and FKBP interacts with the RAFT1/FRAP protein and inhibits signalling from the IL-2 receptor.

Immunophilins have been 4found to be present at high concentrations in the central nervous system. Immunophilins are enriched 10–50 times more in the central nervous system than in the immune system. Within neural tissues, immunophilins appear to influence nitric oxide synthesis, neurotransmitter release, and neuronal process extension.

Nitric oxide serves several roles in the body. In the brain, nitric oxide appears to be a neurotransmitter. It is formed, from arginine, by nitric oxide synthetase which oxidizes the guanidino group of arginine forming nitric oxide and citrulline. Stimulation of the N-methyl-d-aspartate (NMDA) subtype of glutamate receptors rapidly and markedly activates nitric oxide synthetase and stimulates cGMP formation. Inhibition of nitric oxide synthetase with arginine derivatives such as nitroarginine blocks the glutamate induced increase in cGMP levels. Nitric oxide synthetase is a calcium-calmodulin requiring enzyme and N-methyl-d-aspartate receptor activation stimulates nitric oxide synthetase activity because the N-methyl-d-aspartate receptor possesses a calcium channel which is opened by glutamate stimulation, allowing calcium to rush into the cells and activate the nitric oxide synthetase.

Glutamate is a physiologic neurotransmitter. However, when released in-excess, glutamate elicits neurotoxicity via N-methyl-d-aspartate receptors. Treatment of cerebral cortical neuronal cultures with glutamate or N-methyl-d-aspartate kills up to 90% of neurons and these effects are blocked by N-methyl-d-aspartate antagonist drugs. This N-methyl-d-aspartate neurotoxicity is thought to be a major contributor to neuronal damage following vascular stroke. Thus, there is a massive release of glutamate following cerebral vascular occlusion and numerous N-methyl-d-aspartate antagonists block stroke damage. Phosphorylation of nitric oxide synthetase inhibits its catalytic activity. By enhancing nitric oxide synthetase phosphorylation, FK506 might functionally inhibit nitric oxide formation and thus block glutamate neurotoxicity. Indeed, low concentrations of FK506 and cyclosporin A both block N-methyl-d-aspartate neurotoxicity in cortical cultures. The mediating role of FKBP is evident, as rapamycin reverses the therapeutic effect of FK506. Presumably FK506, already marketed as an immunosuppressant, could be clinically employed in stroke patients.

FK506 also augments the phosphorylation of growth-associated protein-43 (GAP43). GAP43 is involved in neuronal process extension and its phosphorylation appears to augment this activity. Accordingly, the effects of FK506 rapamycin and cyclosporin in neuronal process extension have been examined using PC12 cells. PC12 cells are a continuous line of neuronal-like cells which extend neurites when stimulated by nerve growth factor (NGF).

Surprisingly, it has been found that picomolar concentrations of an immunosuppressant such as FK506 and rapamycin stimulate neurite out growth in PC12 cells and sensory nervous, namely dorsal root ganglion cells (DRGs). Lyons et al. *proc. Natl. Acad. Sci. USA*, 1994, 91, 3191–3195. In whole animal experiments, FK506 has been shown to stimulate nerve regeneration following facial nerve injury and results in functional recovery in animals with sciatic nerve lesions.

More particularly, it has been found that drugs with a high affinity for FKBP are potent rotamase inhibitors and exhibit excellent neurotrophic effects. Snyder et al., "Immunophilins and the Nervous System", *Nature Medicine*, Volume 1, No. 1, January 1995, 32–37. These findings suggest the use of immunosuppressants in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived growth factor, glial derived growth factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

The present invention provides non-immunosuppressive as well as immunosuppressive pipecolic acid derivative compounds containing small molecule FKBP rotamase inhibitors which are extremely potent in augmenting neurite outgrowth, and for promoting neuronal growth, and regeneration in various neuropathological situations where neuronal repair can be facilitated including peripheral nerve damage by physical injury or disease state such as diabetes, physical damage to the central nervous system (spinal cord and brain), brain damage associated with stroke, and for the treatment of neurological disorders relating to neurodegeneration, including Parkinson's disease, Alzheimer's disease, and amyotrophic lateral sclerosis.

SUMMARY OF THE INVENTION

This invention relates to the method of using neurotrophic pipecolic acid derivative compounds having an affinity for FKBP-type immunophilins as inhibitors of the enzyme activity associated with immunophilin proteins, and particularly inhibitors of peptidyl-prolyl isomerase or rotamase enzyme activity.

A preferred embodiment of this invention is a method of treating a neurological disorder in an animal, comprising:

administering to an animal an effective amount of a pipecolic acid derivative having an affinity for FKBP-type immunophilins to stimulate growth of damaged peripheral nerves or to promote neuronal regeneration, wherein the FKBP-type immunophilin exhibits rotamase activity and the pipecolic acid derivative inhibits said rotamase activity of the immunophilin.

Another preferred embodiment of this invention is a method of treating a neurological disorder in an animal, comprising:

administering to an animal an effective amount of a pipecolic acid derivative having an affinity for FKBP-type immunophilins in combination with an effective amount of a neurotrophic factor selected from the group consisting of neurotrophic growth factor, brain derived growth factor, glial derived growth factor, cilial neurotrophic factor, and neurotropin-3, to stimulate growth of damaged peripheral nerves or to promote neuronal regeneration, wherein the FKBP-type immunophilin exhibits rotamase activity and the pipecolic acid derivative inhibits said rotamase activity of the immunophilin.

Another preferred embodiment of this invention is a method of stimulating growth of damaged peripheral nerves, comprising;

administering to damaged peripheral nerves an effective amount of a pipecolic acid derivative compound having an affinity for FKBP-type immunophilins to stimulate or promote growth of the damaged peripheral nerves, wherein the FKBP-type immunophilins exhibit rotamase activity and the pipecolic acid derivative inhibits said rotamase activity of the immunophilin.

Another preferred embodiment of this invention is a method of stimulating growth of damaged peripheral nerves, comprising:

administering to damaged peripheral nerves an effective amount of a pipecolic acid derivative compound having an affinity for FKBP-type immunophilins to stimulate growth of damaged peripheral nerves, wherein the FKBP-type immunophilin exhibit rotamase activity and the pipecolic acid derivative inhibits said rotamase activity of the immunophilin.

Another preferred embodiment of this invention is a method for promoting neuronal regeneration and growth in animals, comprising:

administering to an animal an effective amount of a pipecolic acid derivative compound having an affinity for FKBP-type immunophilins to promote neuronal regeneration, wherein the FKBP-type immunophilins exhibit rotamase activity and the pipecolic acid derivative inhibits said rotamase activity of the immunophilin.

Yet another preferred embodiment of this invention is a method for preventing neurodegeneration in an animal, comprising:

administering to an animal an effective amount of a pipecolic acid derivative having an affinity for FKBP-type immunophilins to prevent neurodegeneration, wherein the FKBP-type immunophilin exhibits rotamase activity and the pipecolic acid derivative inhibits said rotamase activity of the immunophilin.

Figure 1:
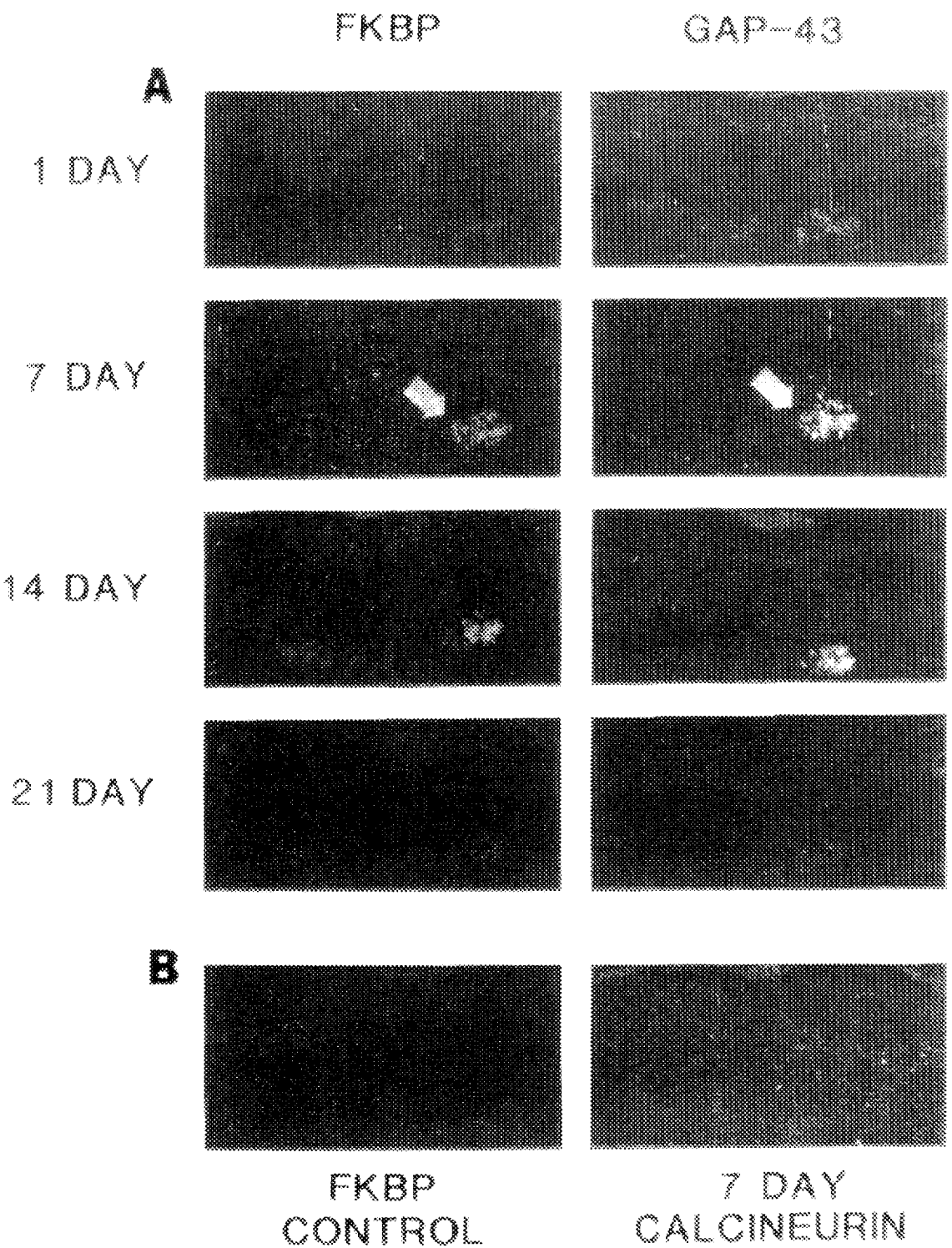
FIG. 1

FKBP-12 and GAP-43 expression in the facial nucleus after nerve crush (FIG. 1A). In situ hybridization comparing the time course of expression of mRNA in the facial nucleus for FKBP12 (left) and GAP-43 (right). The right facial nucleus is ipsilateral to the crush, and the left side is an unoperated control (FIG. 1B). In situ hybridization for FKBP-12 on an untreated control (left) and for calcineurin A$\alpha,\beta$ 7 days following facial nerve crush (right).

Experiments were replicated at least 3 times with similar results.

FIG. 2

Figure 2A:
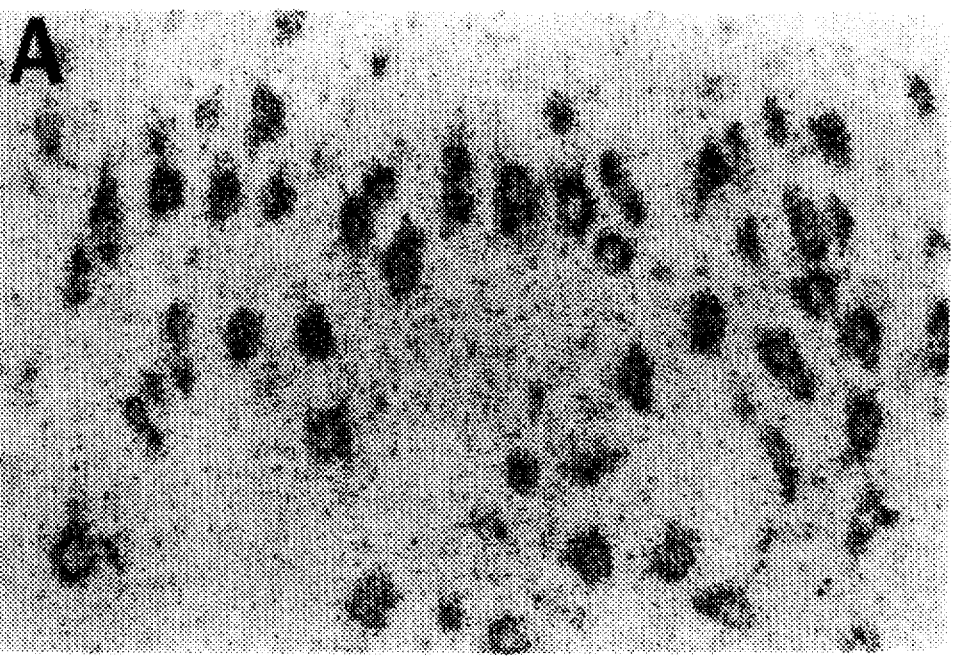
Figure 2B:
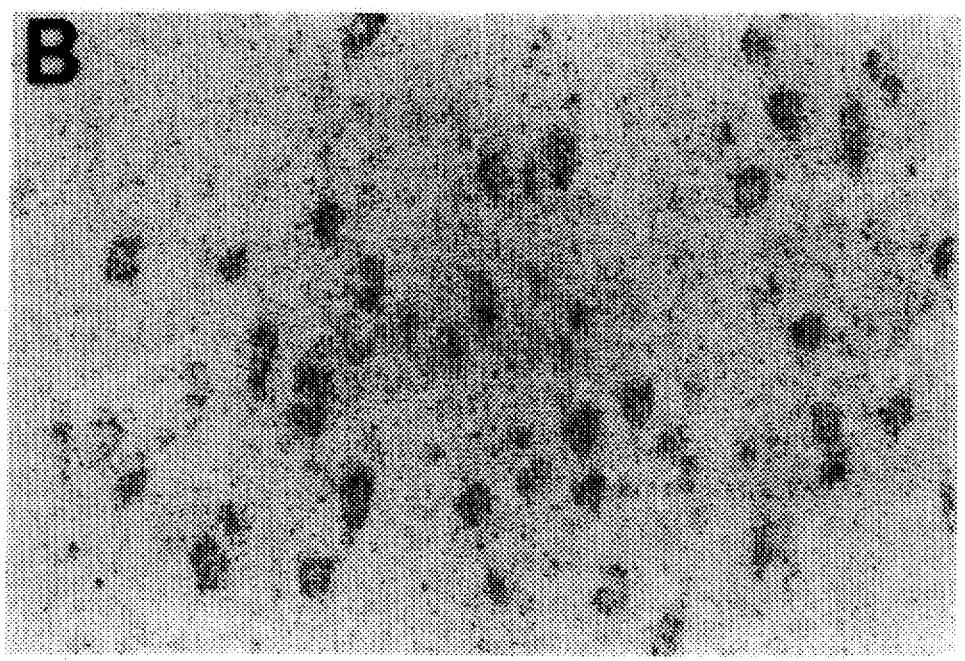

Localization of FKBP-12 to facial motor neurons following nerve crush. Bright-field photomicrographs of in situ hybridization for FKBP-12 in motor neurons of the facial nucleus 7 days after crush (FIG. 2A), and in motor neurons of control facial nucleus (FIG. 2B).

FIG. 3

Upregulation of FKBP-12 mRNA in lumbar spinal cord motor neurons after sciatic nerve crush. In situ hybridization for FKBP-12 7 days after crush of the right sciatic nerve. Top panel (FIG. 3A) shows the response of motor neurons in the ventral horn of lower lumbar spinal cord (indicated by the arrow). Bright field photomicrographs of corresponding motor neuron pools are shown in the bottom panels: (FIG. 3B) left side contralateral to nerve crush, (FIG. 3C) right side ipsilateral to the nerve crush. This experiment was repeated 3 times with similar results.

FIG. 4

Induction of FKBP and FKBP-12 mRNA in the dorsal root ganglion 1 and 6 weeks after sciatic nerve crush. Dark-field photomicrographs of sections through the L4 dorsal root ganglion ipsilateral to sciatic nerve crush processed for FKBP in situ hybridization are shown in the left panels and for [³H]FK506 autoradiography in the right panels. These results were replicated 3 times for each time point.

FIG. 5

Figure 5A:
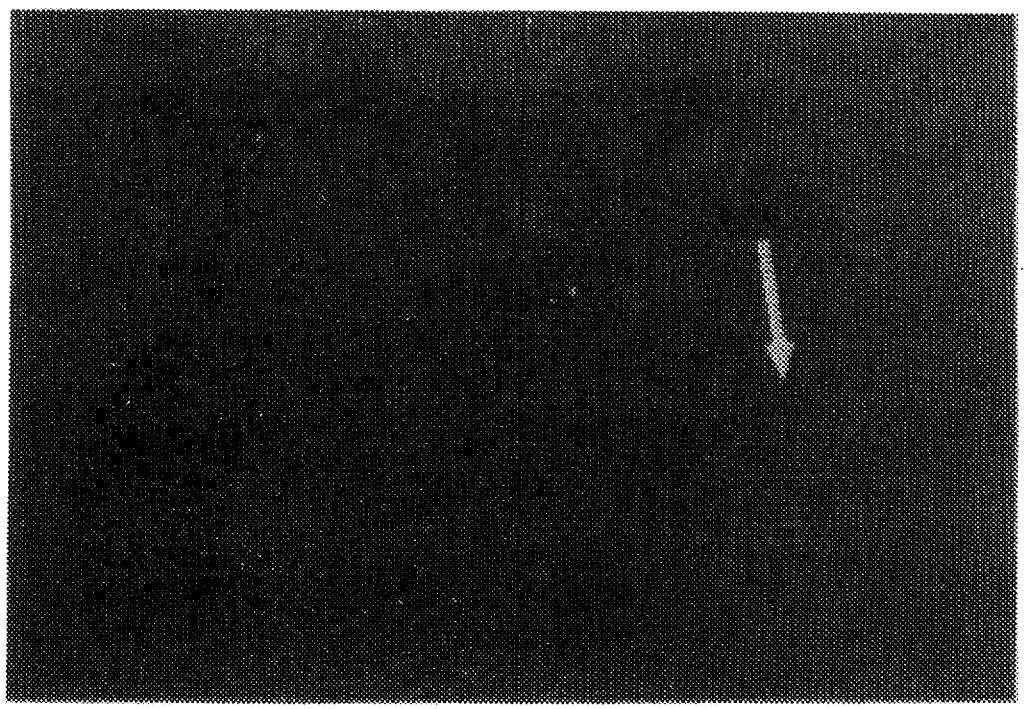
Figure 5B:
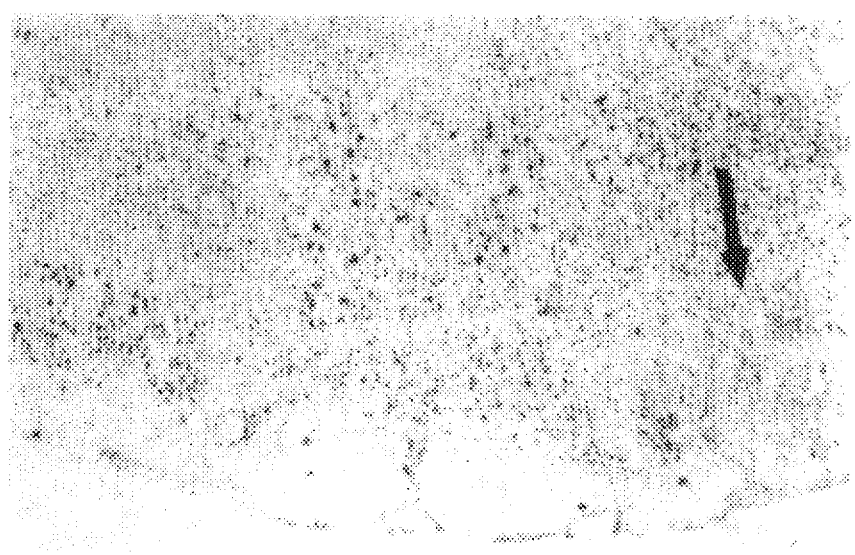

Ricin lesion of the right facial nerve. Nissl stain (bottom panel. FIG. 5A) reveals extensive degeneration of motor neurons in the right facial nucleus with an accompanying glial proliferation 7 days following injection of ricin into the facial nerve. In situ hybridization for FKBP mRNA 7 days after ricin lesion of the facial nerve/nucleus is shown in the top panel (FIG. 5B). This experiment was replicated 3 times with similar results.

FIG. 6

[³H]FK506 binding in segments of sciatic nerve 7 days following crush. The diagram illustrates the 3 mm segments of nerve taken: constrictions indicate positions of ligatures applied at day 7 for the 6 hr collection time as described in the methods. The distal ligature site is 10 mm proximal to the original crush site. Anterograde transport of FKBP is 124 mm/day. Data are the means±S.E.M. (n=3).

FIG. 7

Figure 7A:
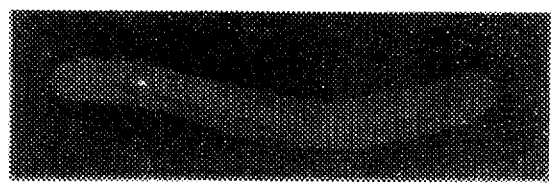
Figure 7B:
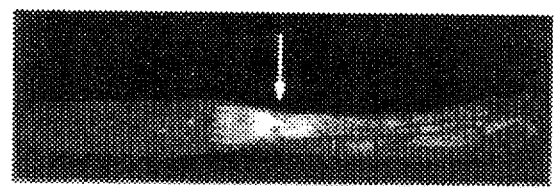
Figure 7C:
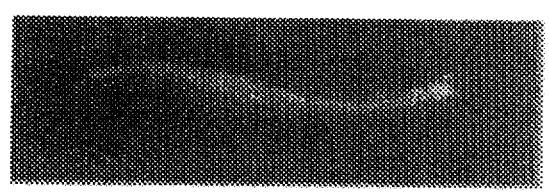
Figure 7D:
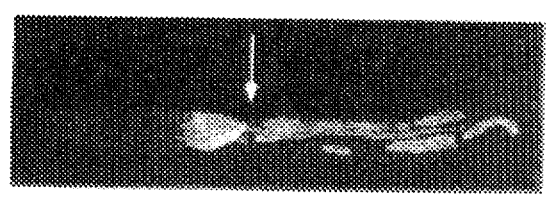

Transport of FKBP in the sciatic nerve. Dark-field photomicrographs of sections through a control (untreated) sciatic nerve and a 7 day sciatic nerve crush site processed for FKBP-12 in situ hybridization (FIG. 7A, FIG. 7B) and for [³H]FK-506 autoradiography (FIG. 7C, FIG. 7D). Arrows indicate the sight of the nerve crush. This experiment was repeated 3 times with similar results.

FIG. 8

Levels of [³H]FK506 binding in PC-12 cells maintained in the presence or absence of NGF (50 ng/ml).n=3 for each time point. Bars represent S.E.M.

FIG. 9

Figure 9A:
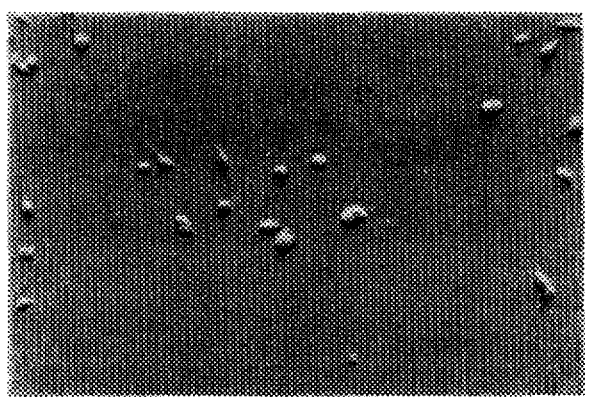
Figure 9B:
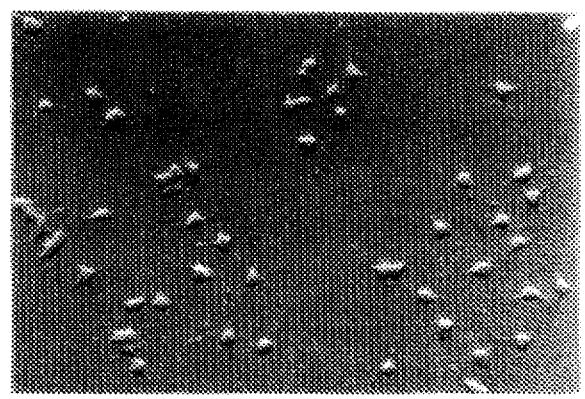
Figure 9C:
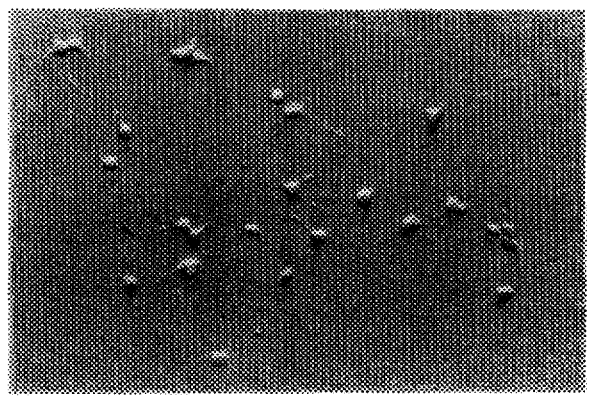
Figure 9D:
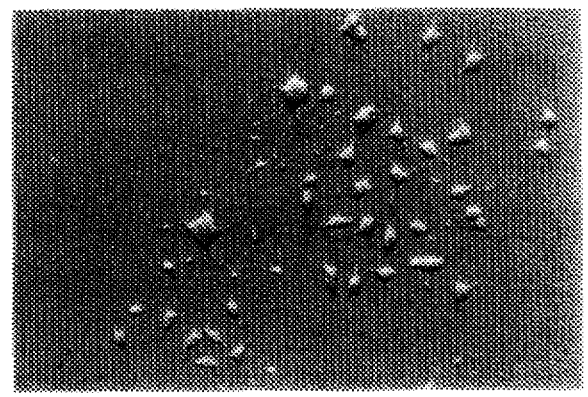

Immunosuppressant mediated enhancement of neurite outgrowth in PC-12 cells. Hoffman contrast photomicrographs (64) of cultures grown for 48 hr in the presence of NGF with or without added FK506 or rapamycin. FIG. 9A: PC-12 cells grown in 1.0 ng/ml NGF. FIG. 9B: 50 ng/ml NGF. FIG. 9C: 1.0 ng/ml NGF and 100 nM FK506. FIG. 9D: 1.0 ng/ml NGF and 100 nM rapamycin. Magnification 200×.

FIG. 10

Effects of FK506 on neurite outgrowth in PC-12 cells. Cultures were treated with varying concentrations of NGF in the presence or absence or 100 nM FK506, and neurite sprouting was measured at 48 hr. Outgrowth was quantitated as described in Methods by counting cells with neuritic processes greater than 5 μm. n=4 separate experiments for each point and error bars represent SEM.

FIG. 11

Concentration-response relationship for FK506 potentiation of neurite outgrowth in PC-12 cells. Cells were treated for 48 hr with 1 ng/ml NGF and varying concentrations of FK506. Neurite outgrowth response was measured as described in FIG. 10 and Methods. n=4 separate experiments for each data point *p<.001 Students t test.

FIG. 12

[³H]FK-506 autoradiography on dorsal root ganglion explant cultures. After 26 days of cultures with 100 ng/ml NGF the extensive processes display abundant FKBP associated silver grains. Autoradiographic grains are abolished with 1 μM unlabeled FK506.

FIG. 13

Phase-contrast micrographs of dorsal root ganglia grown with different substances. FIG. 13A: NGF 100 ng/ml. FIG. 13B: FK506 1 μM. FIG. 13C: FK506 1 μM and anti-NGF antibody. FIG. 13D: No added growth factor. FIG. 13E: FK506 1 pM. FIG. 13F: FK506 1 μM. and rapamycin 1 μM. Scale bar is 205 μm. NGF produces abundant axon outgrowth (FIG. 13A), as does 1 μM FK506 (FIG. 13B). The effects of FK506 are substantially decreased by reducing the concentration to 1 pM (FIG. 13E). However, neurite outgrowth with 1 pM FK506 is greater than in its absence (FIG. 13D). FK506 effects are also diminished by adding anti-NGF antibody to eliminate the effects of NGF produced by non-neuronal cells in the cultures. The abundant neurites that occur in large fascicles in response to NGF (100 ng/ml]) (FIG. 13A) or 1 μM FK506 (FIG. 13B) appear white, while small fascicles or individual neurites appear black. Non-neuronal cells. Schwann cells and some fibroblasts, are more evident with 1 pM FK506 (FIG. 13E) or anti-NGF antibody (FIG. 13C) than with 1 μM FK506 (FIG. 13B). NGF produced by non-neuronal cells in the cultures results in the limited axon outgrowth seen in cultures with no added growth factors (FIG. 13D). The large number of refractile non-neuronal cells, appearing white, tend to overshadow the few neurites (FIG. 13D). Rapamycin completely inhibits axon outgrowth in the presence of FK506 (FIG. 13F). Micrographs are representative of 12–30 ganglia from each experimental condition. Differences between all experimental groups were highly reproducible.

FIG. 14

Effects of FK506 and rapamycin on NGF-mediated neurite extension in PC12 cells. PC12 cells (passage 60) were treated with various concentrations of NGF alone or in the presence of 100 nM FK506, 100 nM rapamycin or 100 nM WAY-124,466. Neurite outgrowth was measured after 96 hours with cells bearing processes longer than the diameter of the cells scoring positive. n=3 separate experiments for each point and error bars represent S.E.M.

FIG. 15

Picomolar concentrations of (A) FK506 and (B) rapamycin and WAY-124,466 potentiate neurite extension elicited by NGF (0.5 ng/ml) in PC12 cells. Low passage PC12 cells were treated for 4 days with 0.5 ng/ml NGF in the presence of various concentrations of FK506 (□), rapamycin ( ) or WAY-124,466 ( ). Neurite expression was quantitated as described above in FIG. 14. The levels of neurite production in the presence of 0.5 ng/ml NGF (designated L) and 50 ng/ml NGF (designated H) are indicated for comparative purposes.

FIG. 16

Photomicrographs of PC12 cells treated with immunophilin ligands+0.5 ng/ml NGF itself or 50 ng/ml NGF.

FIG. 17

Immunophilin ligands reduce the amount of NGF required to produce maximal neurite extension in chick sensory ganglia. Whole dorsal root ganglion explants were isolated from day 9–10 chick embryos and cultured in Matrigel-coated 12-well dishes containing L15 medium plus high glucose , with 10% fetal calf serum supplemented with 10 μM Ara C penicillin and streptomycin) at 37° C. in a 5 % $CO_2$ environment. Sensory ganglia were treated with 1 ng/ml NGF. 1 ng/ml NGF plus 100 nM FK506 or 100 ng/ml NGF for 48 hr, and neuronal processes were counted and photographed.

FIG. 18

FK506, rapamycin, and WAY-124,466 potentiate NGF-dependent neurite production in sensory ganglia. Explants of chick DRG were cultured as described in FIG. 17 above. FK506, rapamycin and WAY-124,466 (100 nM each plus or minus 0.1 ng/ml NGF were added to the DRG explant cultures. At 48 hrs., neurite outgrowth was quantitated and the cultures were photographed.

DETAILED DESCRIPTION OF THE INVENTION

The novel neurotrophic pipecolic acid derivative compounds of this invention have an affinity for the FK506 binding proteins such as FKBP-12. When the neurotrophic compounds of the invention are bound to FKBP, they have been found to inhibit the prolyl- peptidyl cis-trans isomerase activity, or rotamase activity of the binding protein and unexpectedly stimulate neurite growth.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathic such as those caused by lead, dapsone, ticks, porphyria, or Guillain-Barré syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets the immunophilin-drug complex should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg. of the active ingredient compound are useful in the treatment of the above conditions, with preferred levels of about 0.1 mg. to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Methods and Procedures
Sciatic Nerve Crush

This example demonstrates high levels of FKBP in normal peripheral nerve and that these increase following nerve crush.

If FKBP were physiologically associated with neuronal process extension in the actions of GAP-43, then one might anticipate substantial levels of FKBP in peripheral nerve. Accordingly, we measured [$^3$H]FK-506 binding in rat sciatic nerve, as well as in growth cones isolated from 2-day-old rat pups, and compared values with those of the cerebral cortex and several peripheral tissues.

[$^3$H]FK-506 autoradiography was carried out as described on unfixed sections which were thawed and air dried before preincubation for 1 hr in buffer consisting of 50 mM Hepes, 2 mg/ml bovine serum albumin, 5% ethanol, and 0.02% Tween 20 pH 7.4. Sections were then exposed to 1 nM [$^3$H]FK-506 (86.5 Ci/mMol; DuPont-NEN, Boston, MA) for 1 hr at room temperature in preincubation buffer. Non-specific binding was defined by addition of 1 AM FK-506. Following incubation, the slides were washed 4×5 min in ice cold preincubation buffer and air dried. The radiolabeled sections were then juxtaposed to tritium-sensitive film or coverslips coated with Kodak NTB-2 emulsion.

TABLE I

[$^3$H]FK506 Binding to Sciatic Nerve and Growth Cones (A) [$^3$H]FK506 Binding in Sciatic Nerve

| Tissue | Bmax (pmol/mg protein) |
|---|---|
| Adult Rat | |
| Sciatic Nerve | 22.1 |
| Cerebral Cortex | 38.0 |
| Thymus | 9.5 |
| Spleen | 8.0 |
| Neonatal Rat | |
| Forebrain | 25.5 |
| Growth Cones | 10.2 |

(B) [$^3$H]FK506 Binding After Sciatic Nerve Crush

| protein | Bmax fmol/5 mm segment | Bmax pmol/mg |
|---|---|---|
| Unoperated | 31.8 ± 2.1 | 21.2 ± 1.4 |
| 7-Day Crush | 136.5 ± 15.7* | 40.1 ± 2.0* |

[$^3$H]FK506 binding was assayed as described in methods. In Table 1A experiments were replicated three times with less than 10% variation. In Table 1B values are presented as the mean ± S.E.M. (n = 3). *P ≤ 0.05 Students' t-test for independent means.

Of all the tissues examined sciatic nerve binding levels are the highest, somewhat higher than those of the cerebral cortex and about 10× higher than levels in the thymus and spleen, which contain FKBP associated with lymphocytes. See Table 1A.

Evidence for a role of FKBP in nerve regeneration comes from experiments in which we crushed the sciatic nerve of adult rats and 7 days later measured [$^3$H]FK506 binding in a 5 mm segment immediately proximal to the nerve crush.

Sprague-Dawley rats (175–200g) were anesthetized with a mixture of Rompun (12 mk/kg) Ketamine (30 mg/kg). Using aseptic techniques, the facial nerve was crushed with jewelers forceps 2×30 sec 2 mm distal to its exit from the stylomastoid foramen. Identical procedures were used to crush the sciatic nerve at the level of the mid-thigh.

Total binding in the segment proximal to the crush was quadrupled compared to control values. Since total protein is substantially augmented in the proximal segment, [$^3$H] FK-506 binding per mg protein is only doubled in the proximal segment.

Facial Nerve Crush

This example demonstrates that facial nerve lesions augment the coincident expression of FKBP and GAP-43.

Following the crush of the facial nerve, mRNA levels of GAP-43 increase in the facial nerve nucleus. Utilizing in situ hybridization, we examined mRNA levels of FKBP, GAP-43 and calcineurin following facial nerve crush.

Rats were perfused transcardially with 150–200 ml ice cold phosphate-buffered saline (PBS) (0.1M, pH 7.4). Tissues were removed and immediately frozen in isopentane (−80° C.). Cryostat sections 18 µm thick) were cut and thaw mounted on gelatin coated slides.

In situ hybridization was performed as previously described, using antisense oligonucleotide probes end labeled with [$^{35}$]dATP. For FKBP, three separate oligonucleotides complementary to the following regions of the cloned cDNA disclosed by Maki, et al. (1990) Proc. Natl. Acad. Sci. USA 87, 5440–5443, and Standaert, R. F., et al. (1990) Nature 346, 671–674 and incorporated herein by reference.

were used: 70–114, 214–258, 441–485. For GAP-43, three separate antisense oligonucleotides complementary to nucleotides 961–1008, 1081–1128, 1201–1248 of the cloned cDNA disclosed by Rosenthal, A., et al. (187) *EMBO J.* 6, 3641–3646 and incorporated herein by reference were used. For calcineurin Aα antisense oligonucleotides complementary to the nucleotides 1363–1410 and 1711–1758, disclosed by Ito et al. (1989) *Biochem. Biophys. Res. Commun.* 163, 1492–1497 and incorporated herein by reference, and for calcineurin Aβ 1339–1386 and 1569–1616 disclosed by Kuno, T., et al. (1989) *Biochem. Biophys. Res. Commun.* 165, 1352–1358 and incorporated herein by reference, were used. Sections were thawed and allowed to dry, then fixed for 5 min in 4% freshly depolymerized paraformaldehyde in PBS. Following two rinses in PBS, sections were acetylated with 0.25% acetic anhydride in 0.1M triethanolamine 0.5% NaCl (pH 8.0), and then dehydrated in graded alcohols, defatted in chloroform for 5 min, rehydrated to 95% ethanol and allowed to air dry. Hybridization was performed overnight at 37° C. in buffer containing 50% deionized formamide, 10% dextran sulfate, 4×SSC, 1×Denhardt's solution, 20 mM phosphate buffer, 0.1 mg/ml salmon sperm DNA, 0.1 mg/ml yeast transfer RNA, 10 mM dithiothreitol, 2.0% betamercaptoethanol (BMD), 1.0 mM EDTA and labelled probe (2,000,000 dpm/section). Following hybridization, sections were rinsed in 1×SSC, 1.0% BME for 15 min at room temperature, then twice for 10 min at 55° C. air dried and placed on film or dipped in Kodak NTB-2 emulsion.

Striking enhancement of FKBP and GAP-43 expression is observed, while no changes are evident in calcineurin expression. As early as 24 hr following facial nerve crush FKBP expression is increased with peak levels evident a 1–2 weeks, while mRNA concentrations diminish substantially at 3 weeks. Examination under higher magnification reveals that the increased levels of silver grains for FKBP mRNA are confined to neuronal cell bodies (FIG. 2). Northern blot analysis of the dissected facial nucleus confirms the increased levels of FKBP specific mRNA. GAP-43 mRNA levels follow a time course closely similar to those of FKBP. By contrast, no changes in calcineurin expression are detected at any of the time points examined.

Total cellular RNA from the dissected facial nucleus was isolated. Samples of 10 or 20 ug total RNA were electrophoresed through a 1% agarose, 2.0% formaldehyde gel and transferred to a nylon membrane in 10 nM NaOH. cDNA probes to FKBP labeled with [$^{35}$]dCTP to a specific activity of 1×10$^9$ cpm/ug by random priming were hybridized overnight at 42° C. in buffer consisting of 50% formamide, 2×SSPE, 7% SDS, 0.5% Blotto and 100 ug/ml salmon sperm DNA. The blots were washed for 20 min at room temperature, and 2×15 min at 65° C. in 0.15×SSC, 0.15% SDS and then exposed to film for 48096 hrs.

On the unlesioned side a modest increase in silver grains compared to control sections are observed. This is consistent with findings that contralateral neurons also respond to axotomy.

Following facial nerve crush, rats develop a facial nerve palsy, which is evident by the lack of whisker movement with functional recovery at 3 weeks coincident with the completion of nerve regeneration. In our rats we also observed the loss of whisker movement following nerve crush with a return of function at 3 weeks. Thus, the time course of increased expression of GAP-43 and FKBP correlates with the process of nerve regeneration.

Sciatic Nerve Regeneration

This example demonstrates alterations in FKBP and GAP-43 associated with sciatic nerve regeneration.

Figure 4:
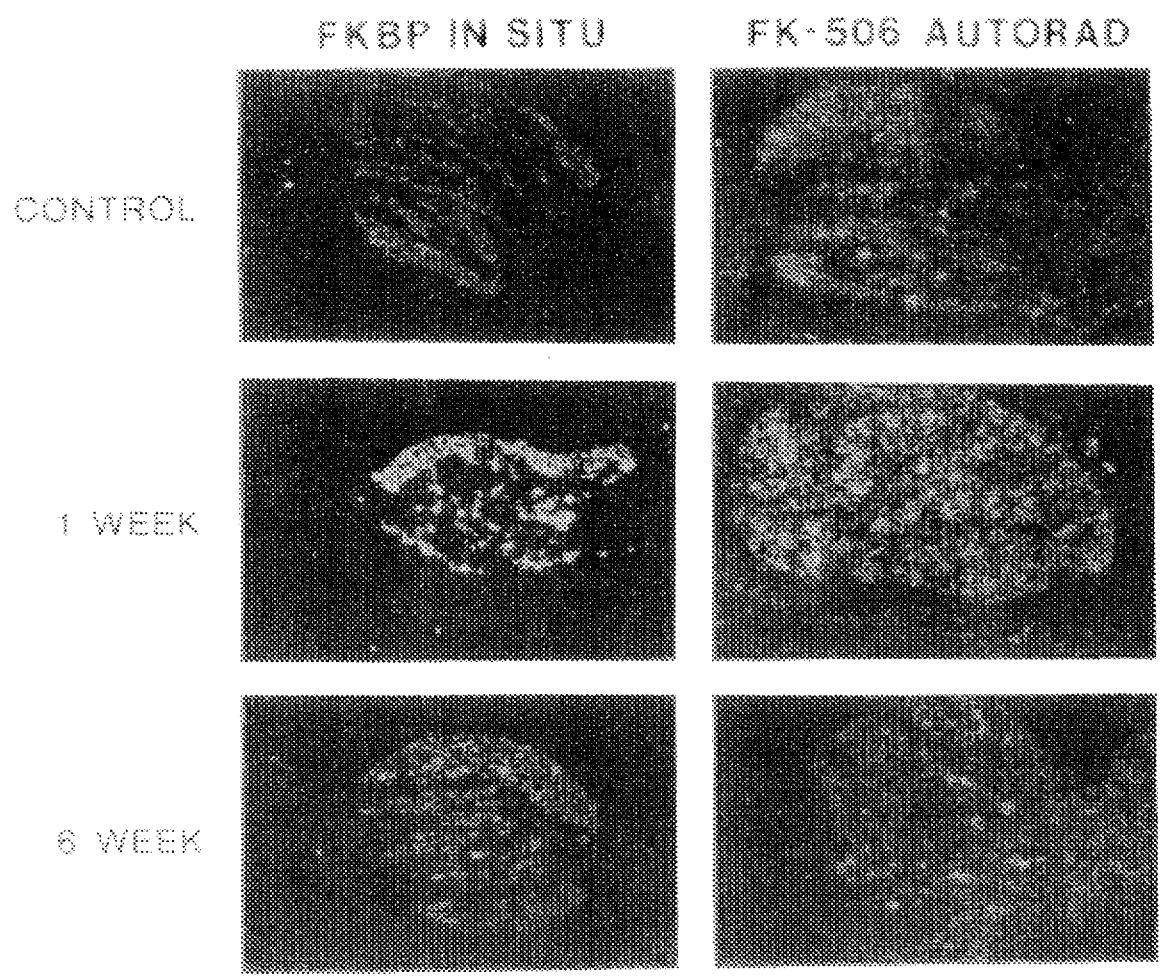

Following sciatic nerve lesions GAP-43 mRNA levels are enhanced in both spinal cord motor neurons and in dorsal root ganglia neuronal cells. In rats subjected to sciatic nerve crush, we observed a striking enhancement in mRNA levels for FKBP in motor neurons at L-4, 5 (FIG. 3) and in dorsal root ganglia neuronal cells coincident with the reported enhancement of GAP-43 expression (FIG. 4). At high magnification we observed the FKMB mRNS silver grains localized to neuronal cell bodies (FIG. 3). We monitored FKBP protein levels by autoradiography of [$^3$H]FK-506 binding under conditions in which it binds selectively to FKBP (FIG. 4). Increased FKBP is detected in the primary sensory neurons in the dorsal root ganglia, though no increases are evident in motor neuronal cells following sciatic nerve crush.

The association of augmented FKBP expression with regeneration selectively is further supported by experiments with ricin. When injected into peripheral nerves ricin is transported back into the cell body which is destroyed without associated nerve regeneration. We injected 0.5 ug ricin (RCA 60, Sigma, St. Louis, Mo.) into the facial nerve at the same site where crushes had been performed in other experiments according to the method of Streit and Kreutzbnerg in 0.5 ul PBS and 0.1 Fast Green. Streit et al., (1988) *J. Comp. Neurol.* 268, 248–263.

We conducted in situ hybridization localization studies for FKBP mRNA at 2, 4 and 7 days following ricin treatment (FIG. 5). No increase in FKBP mRNA is observed following ricin treatment. Gliosis occurs both following ricin treatment and nerve crush. The failure of FKBP mRNA to increase following ricin treatment fits with the selective neuronal localization of FKBP mRNA in the facial nucleus.

FKBP Transport in the Sciatic Nerve

This example demonstrates that FKBP is rapidly transported in the sciatic nerve.

Figure 6:
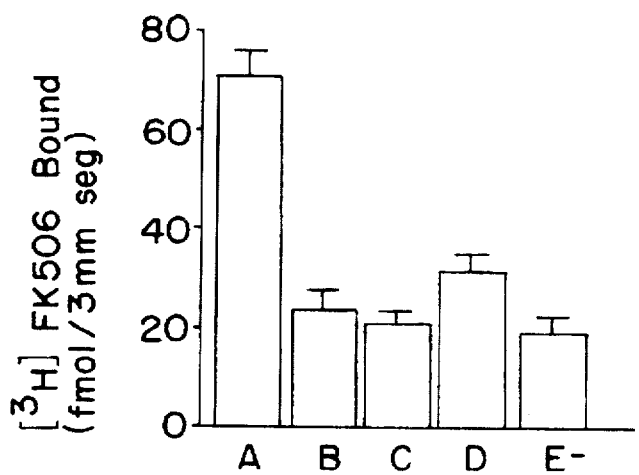

The failure of FKBP protein to increase in motor neurons following sciatic nerve crush despite the increase in FKBP mRNA suggests that the protein is rapidly transported out of the cell body into nerve processes. This fits with out earlier observations that FKBP mRNA is concentrated in granule cells of the cerebellum which contain low levels of FKBP protein, while FKBP protein levels are highly concentrated in the molecular layer in the cerebellum associated with the parallel fibers arising from granule cells. To examine for possible transport of FKBP, we crushed the sciatic nerve and 7 days later applied ligatures 10 and 20 mm proximal to the crush. Six hr following ligature, we monitored [$^3$H]FK-506 binding in 3 mm segments spanning the area of the ligatures. (FIG. 6).

For axon transport experiments, classic ligature techniques were used following the methods of Tetzlaff et al. One week following sciatic nerve crush two collection ligatures (510 sutures) were placed on the nerve approximately 10 mm apart with the distal most ligature positioned 10 mm proximal to the initial crush site. Six hours later, 5–3 mm segments of the nerve were collected from regions proximal to, distal to, and between the collection ligatures as illustrated in FIG. 5. The nerve segments were prepared for [$^3$H]FK-506 binding assays by homogenizing in 10 volumes of 50 mM Tris-HCl, pH 7.4 Homogenates were centrifuged at 15,000×g for 20 min at 4° C., and supernatants were collected and assayed for total protein concentration using the Coomassie blue dye binding assay (Pearce). [$^3$H]FK-506 binding was carried out as described (4) on aliquots containing 2 ug of total soluble protein in a final volume of 0.4 ml assay buffer consisting of 50 mM Tris-HCl, pH 7.4, 2 mg/ml bovine serum albumin, 250 pM [$^3$H]FK-506, and varying concentrations of unlabeled FK-506. Following incubation at 25° C. for 60 min, 0.35 ml was layered over a 0.8 ml column of LH-20 Sephadex (Pharmacia LKB) and washed with 0.4 ml of assay buffer. The eluates were collected and counted in a scintillation counter.

Results are shown in FIG. 5. [$^3$H]FK-506 binding levels are highest in the segment just proximal to the ligature 20 cm from the crush, being almost quadruple levels in the other segments. Based on the levels of [$^3$H]FK-506 binding in segments A–D, we calculated the rate of anterograde transport for FKBP. This rate of 240 mm per day is essentially the same as transport rates for GAP-43 representing the most rapid transport rates for neuronal proteins.

To visualize the accumulation of FKBP following nerve crush, we applied a loose ligature to mark the site of crush of the sciatic nerve and conducted in situ hybridization for FKBP mRNA as well autoradiography for [$^3$H]FK-506 binding (FIG. 7). Most FKBP mRNA and [$^3$H]FK-506 binding accumulate immediately proximal to the crush. These levels are considerably higher than in control uncrushed sciatic nerve. Examination of the in situ hybridization an autoradiography preparations at high magnification reveals silver grains associated with neuronal fibers. There are also silver grains localized to cells whose identity we could not determine definitively, so that they may be Schwann cells, macrophages or fibroblasts.

FKBP in PC12 Cells

This example demonstrates that PC-12 cells contain FKBP and that FKBP levels are enhanced by nerve growth factor. We examined PC-12 cells for the presence of FKBP by monitoring the binding of [$^3$H]FK-506 to cells under basal conditions and following treatment with nerve growth factor (NGF).

Levels of FKBP in PC-12 cells were obtained from Scatchard analysis of [$^3$H]FK-506 binding curves. Cultures were scraped from the culture wells and homogenized in 10 volumes of 50 mM Tris-HCl,pH 7.4, 1 mM EDTA, 100 µg/ml phenylmethylsulfonylfluoride and centrifuged at 40,000×g for 20 min at 4° C. Protein was determined by the-Coomassie blue dye binding assay using bovine serum albumin as a standard. Binding of 250 pM [$^3$H]dihydro FK506 (86.5 Ci/mmol, DuPont/NEN) was assessed for samples containing 5 µg soluble protein in a final volume of 0.4 ml assay buffer containing 50 mM Tris-HCl, pH 7.4, 2 mg/ml BSA and varying concentrations of unlabeled FK506. After 60 min incubation at 25° C., 0.35 ml was layered over a 0.8 ml column of LH-20 Sephadex (Pharmacia LKB), pre-equilibrated with assay buffer. The column was further washed with 0.4 ml of assay buffer, the eluates collected, mixed with Formula 963 (DuPont/NEN) and counted in a Beckman scintillation counter. Specific binding was determined by subtracting binding obtained in the presence of 1 µM unlabeled FK506 from total [$^3$H]FK506 bound.

Figure 8:
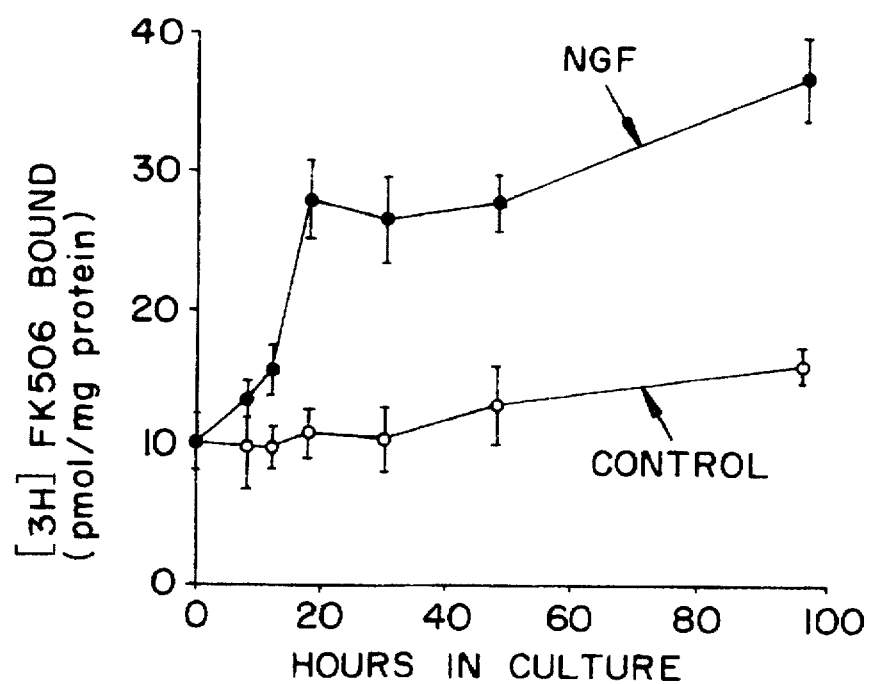

Results are shown in FIG. 8. [$^3$H]FK506 binds saturably to untreated PC-12 cell homogenates. In typical experiments about 1,000 cpm are bound while nonspecific binding in the presence of 1 µM FK506 is about 150 cpm. Fifty percent inhibition of [$^3$H]FK506 binding occurs with 1–2 nM FK506 indicating that the binding sites correspond to authentic FKBP. [$^3$H]FK506 binding increases markedly following NFG treatment. Significant increases are evident by 10–15 hr. Binding triples by 20 hr and a modest further increase is evident at 100 hr.

Increased Neurite Extension in PC12 Cells

This example demonstrates that FK506 and rapamycin increase neurite extension in PC-12 cells.

PC-12 cells were maintained at 37° C., 5% $CO_2$, in Dulbecco's modified Eagle medium (DMEM) supplemented with 10% heat-inactivated horse serum and 5% heat-inactivated fetal bovine serum. For differentiation in NGF, cells were plated at 1×10$^5$ in 35 mm culture wells coated with rat tail collagen at 5 µg/cm$^2$, and allowed to attach before replacing the media with DMEM supplemented with 2% fetal horse serum, NGF and/or FK506 of rapamycin. For quantitation of neurite outgrowth, random photographs were made (3–4 per well), and process bearing neurons were counted with processes being greater than 5 µm. Experimental conditions were unknown by the photographer and cell counter. Four separate experiments were performed in duplicate for each data point presented. Neurites were identified and counted from approximately 100 cells per photograph. Thus, neurites from 1200–1600 cells were counted per data point.

Figure 10:
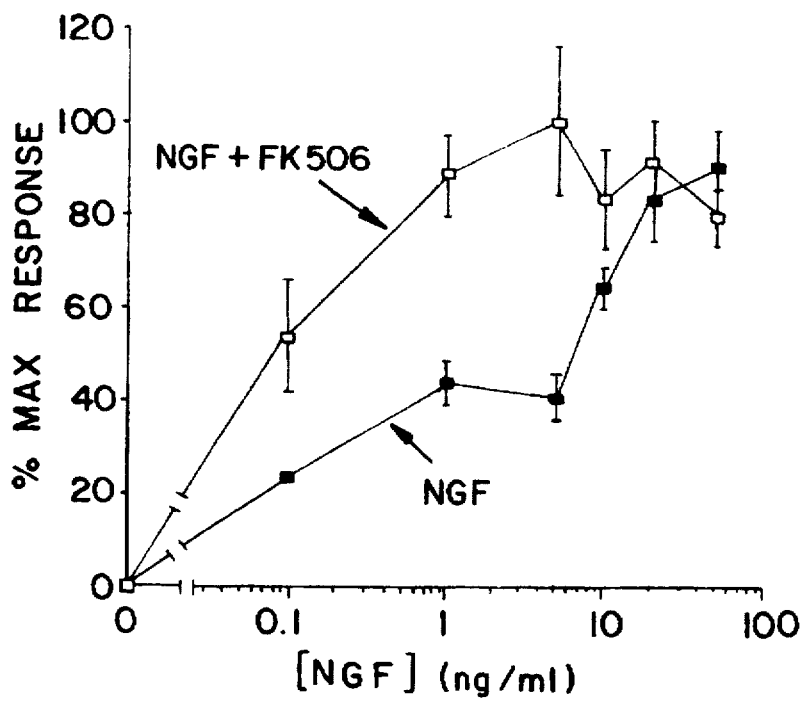

As observed, NGF potently stimulates neurite outgrowth with half-maximal stimulation at 1 ng/ml and maximal augmentation at about 50–100 ng/ml (FIGS. 9, 10). FK506 (100 nM) markedly augments the effect of NGF by increasing sensitivity to NGF. Thus, FK506 reduces by 20–50 fold the NGF concentration needed to elicit maximal outgrowth. Half maximal outgrowth in the absence of FK506 occurs at 5 ng/ml NGF and in the presence of FK506 at 0.1 ng/ml NGF. At maximal concentrations of NGF (10–100 ng/ml), FK506 fails to produce additional neurite outgrowth.

Figure 11:
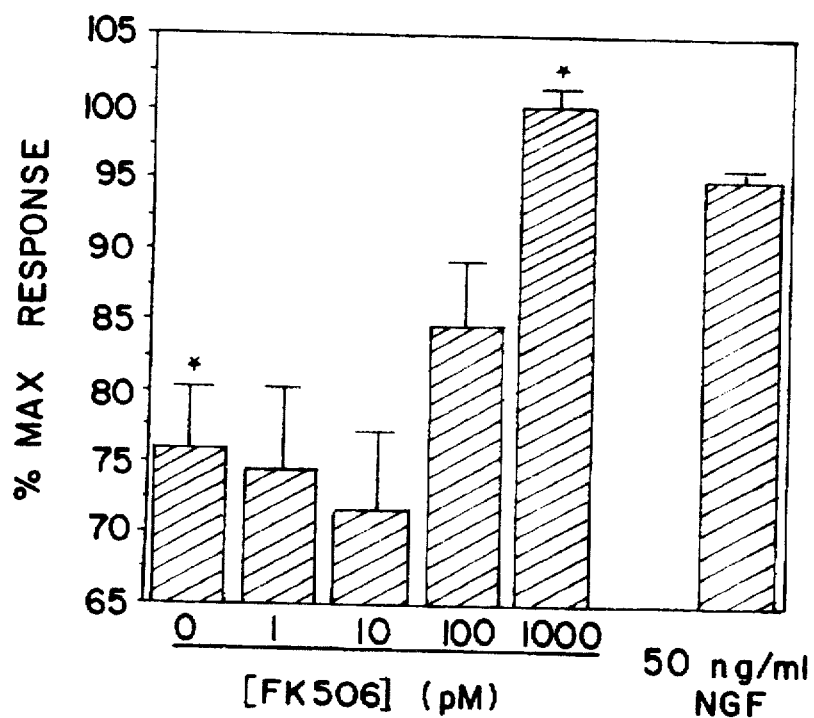

FK506 is extremely potent in its neurotrophic effects. In the presence of a submaximal concentration of NGF (1 ng/ml) FK506 at 1 nM elicits the same maximal outgrowth observed with 50 ng/ml NGF (FIG. 11). Half maximal effects of FK506 occur at approximately 100 pM. In the absence of NGF, FK506 fails to elicit neurite outgrowth (FIG. 10).

Rapamycin is a potent immunosuppressant which is not thought to act through calcineurin but which may influence other phosphorylation cascades. Rapamycin potently blocks actions of FK506 that occur through FKBP and calcineurin presumably by acting as an FK506 antagonist at FKBP. Rapamycin (1 µM) fails to block the neurotrophic actions of FK506. Instead, rapamycin is itself neurotrophic providing major neurite outgrowth at 1 nM. Rapamycin and FK506 seem to be acting via different mechanisms. Thus, rapamycin augments the number of processes as well as their length, while FK506 primarily increases neurite length. Moreover, effects of FK506 and rapamycin appear to be additive.

Dorsal Root Ganglia

This example demonstrates that FK506 is neurotrophic for sensory ganglia. We examined the action of FK506 on primary cultures of dorsal root ganglia from rats at embryonic day 16.

Stage E16 embryos were removed from pregnant Sprague-Dawley rats and the dorsal root ganglia dissected. Whole ganglia explants were cultured in collagen-coated 35 mm dishes (Falcon) using N2 medium (Dulbecco's Modified Eagle medium and Ham's F12 medium mixed 1:1 and supplemented with progesterone, selenium, insulin, putrescine, glucose, and penicillin-streptomycin) at 37° C. in a 15% $CO_2$ environment. Sensory ganglia were treated with various concentrations of NGF and/or FK506 or rapamycin or anti-NGF antibody. Ganglia were observed every 2–3 days under phase-contrasting using an Olympus IMT-2 inverted microscope, and measurements of axon length were made. The axonal field of each ganglion was divided into four quadrants, and the length of the longest axons in each quadrant was measured in microns using an eye-piece micrometer. The average of these measurements was taken as the axon length for the ganglion.

For [$^3$H]FK506 autoradiography, dorsal root ganglia cultures were grown on chamber slides coated with collagen, 5

μg/cml. Cultures were fixed on the slide with ice cold 4.0% freshly depolymerized paraformaldehyde in 0.1M sodium phosphate buffer, pH 7.4, for 1 hr, then washed two times with phosphate buffered saline. Fixed cultures were labeled with [$^3$H]FK506 by pre-incubating the slides in a buffer consisting of 50 mM Hepes, 2 mg/ml bovine serum albumin, 0.02% Tween-20 pH 7.4. This was followed by incubation in the same assay buffer containing 1 nM [$^3$H]FK506. Non-specific binding was determined by adding 1 μM unlabeled FK506. The slides were then rinsed 4×5 min prior to drying, and juxtaposed to tritium-sensitive film for 10 days.

Figure 12:
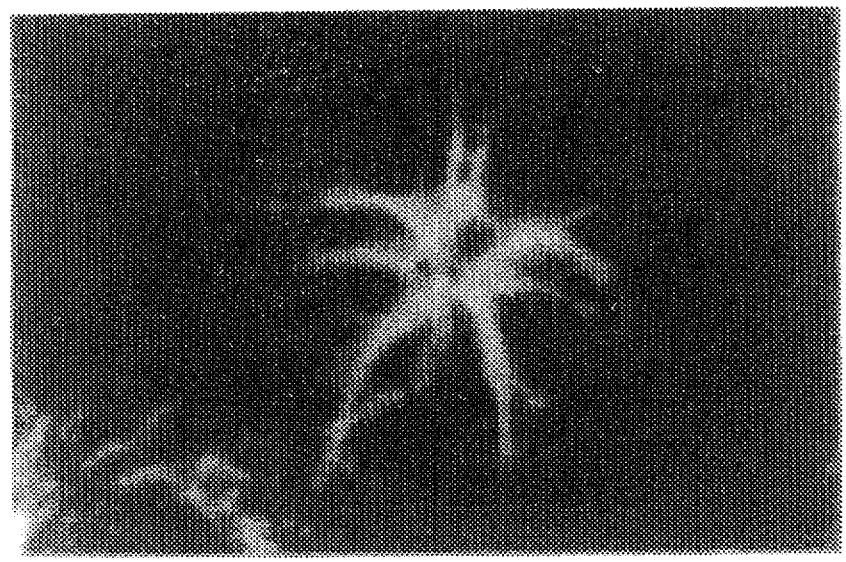

Autoradiography of [$^3$H]FK506 binding sites reveals substantial levels of FKBP associated silver grains in these ganglia (FIG. 12). At 1 μM unlabeled FK506, autoradiographic grains are abolished indicating the specificity of binding. As reported previously, NGF (100 ng/ml) markedly increases the number and length of ganglia processes (FIG. 13). FK506 (1 μM) alone produces a similar neurotrophic effect, while as little as 1 nM FK506 produces a noticeable increase in growth. Rapamycin (1 μM) which acts as an FK506 antagonist, completely blocks the effects of FK506 (1 μM), thus the action of FK506 displays a drug specificity characteristic of FKBP.

Whereas FK506 fails to stimulate neurite outgrowth in PC-12 cells in the absence of added NGF, in sensory ganglia FK506 alone is neurotrophic. Schwann cells in the ganglia can fabricate NGF, and the production of NGF by Schwann cells is regulated by a protein phosphorylation event. To ascertain whether the actions of FK506 alone involve potentiation of endogenous NGF, we examined the influence of antibodies to NGF (FIG. 13). Anti-NGF markedly reduces the neurotrophic effects of FK506 (1 μM). The anti-NGF is not acting in a toxic fashion as we observe no morphologic evidence of toxicity in the cells exposed to anti-NGF in the presence or absence of added NGF.

FK506 is extremely potent in stimulating neurite outgrowth. As little as 1 pM FK506 produces detectable augmentation. Progressively greater outgrowth occurs at 0.1 and 10 nM FK506 (data not shown), while maximal outgrowth requires 1 μM FK506.

The time course of neurite outgrowth is similar at all concentrations of NGF and FK506. Some outgrowth is evidence by 1 day, while growth begins to plateau at about 5–6 days.

FK506 neurotrophic effects involve FKBP (FK506 binding protein) in sensory ganglia since the effects of FK506 are reversed by low concentrations of rapamycin, a known antagonist of FK506 at FKBP. The failure of rapamycin to block FK506 effects in PC-12 cells probably reflects the separate stimulatory effects of rapamycin. Mechanisms for rapamycin stimulation of neurite outgrowth in PC-12 cells are not immediately evident. Its immunosuppressant actions are thought to involve different mechanisms than those of FK506. Rapamycin can inhibit S6 kinase which phosphorylates the S6 ribosomal subunit. Rapamycin also inhibits phosphatidylinositol-3-kinase.

Protein kinase C (PKC) -mediated phosphorylation has been implicated in process outgrowth during neuronal regeneration. Other evidence suggests inhibitory effects of PKC in neuronal process extension.

GAP43 is a prominent calcineurin substrate highly concentrated in neurites and its phosphorylation is regulated by FKBP. GAP43 may not be directly involved in neurite extension, as PC-12 cell lines with low levels of GAP43 display normal neurite outgrowth. However, GAP43 and its phosphorylation may be involved in targeting neurites, as levels of phosphorylated GAP43 are increased when neurites approach their targets. Phosphorylation of GAP-43 may also influence mobilization of $Ca^2$ that regulates neurite extension. Phosphorylated GAP-43 inhibits phosphatidyl inositol bis-phosphate formation, which should diminish level of inositol 1,4,5-triphosphate and associated $Ca^{2+}$ release. In addition, phosphorylation of GAP-43 decreases its affinity for calmodulin with the resultant free calmodulin available to bind $Ca^{2+}$.

Immunophilins may act at sites besides calcineurin which affect $Ca^{2+}$ that regulates neurite outgrowth. FKBP binds to the ryanodine receptor, which is a $CA^{2+}$ release channel. In skeletal muscle sarcoplasmic reticulum FK506 dissociates FKBP from the ryanodine receptor to facilitate the $Ca^{2+}$ induced $Ca^{2+}$ release mechanism. In addition, FK506 acts at other sites including FKBP25 steroid receptors and other unidentified targets such as those related to FKBP13. Thus other potential mechanisms may play some role in neurite extension.

Non-Immunosuppressive and Immunosuppressive Ligands of Immunophilins Stimulate Neurite Outgrowth In PC-12 Cells In the present study we have examined in detail influences of a number of ligands of the immunophilins upon neurite extension in PC-12 cells and in intact chick sensory ganglia. We report that non-immunosuppressive as well as immunosuppressive ligands are extremely potent in augmenting neurite outgrowth in both PC-12 cells and sensory ganglia.

In our earlier study we found that immunosuppressants stimulate neurite outgrowth in PC-12 cells by increasing the potency of nerve growth factor (NGF) about 10-fold (Lyons et. al., 1994). In the absence of added NGF no neurotrophic effects are observed. In the present study we evaluated effects of the immunosuppressant drugs FK506 and rapamycin on PC-12 neurite outgrowth in the presence of 0.1–100 ng/ml of NGF.

Figure 14:
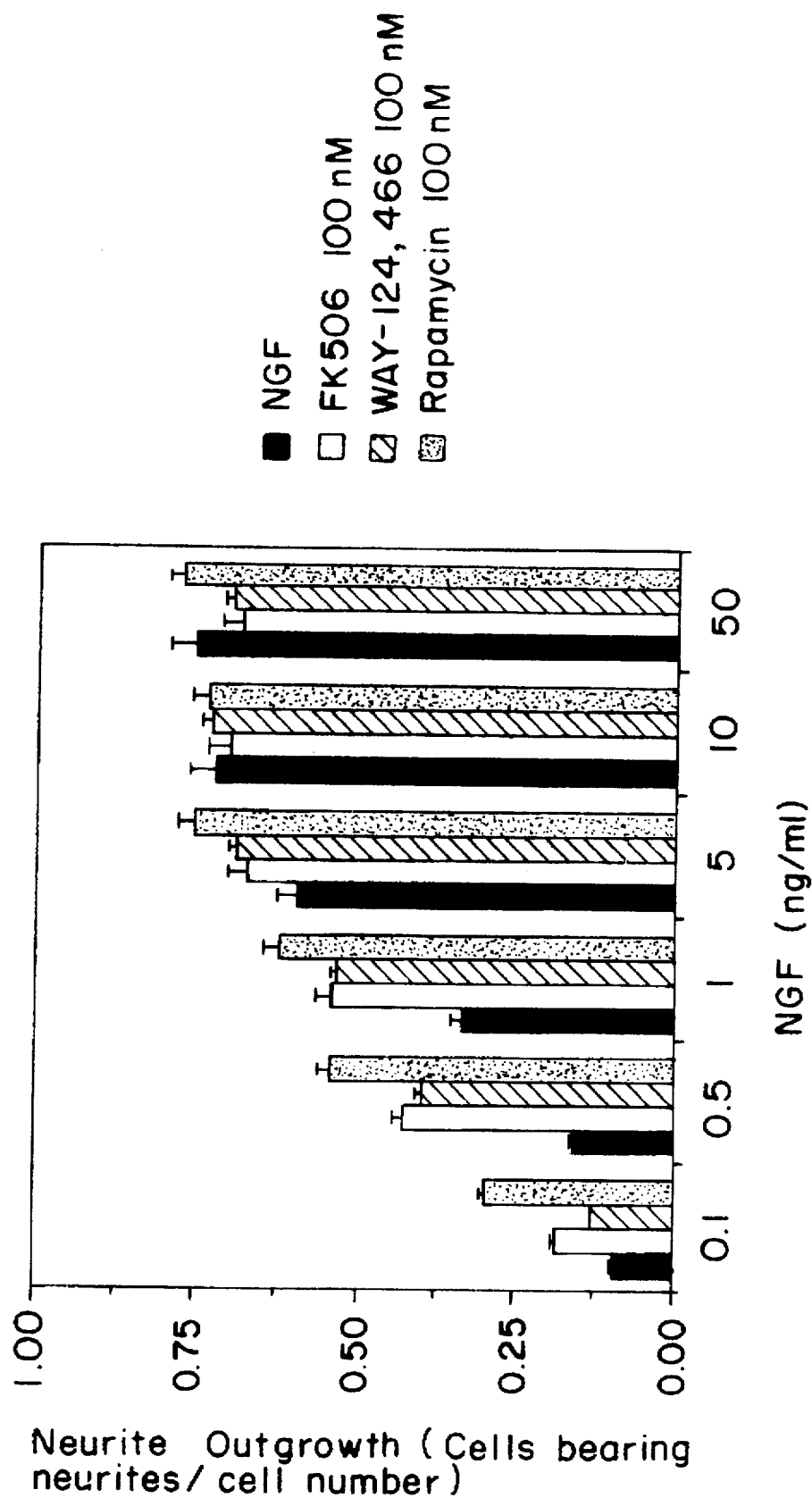

In the absence of added NGF, none of the drugs stimulate neurite outgrowth. At 0.1 ng/ml NGF alone produces a small increase in neurite extension only about 15% of maximal effects that are evident at 50 ng/ml (FIG. 14). Rapamycin stimulates neurite outgrowth to a greater extent than the other drugs, with a 3–4 fold stimulation at 0.1–0.5 ng/ml NGF. The extent of augmentation elicited by rapamycin decreases with higher concentration of NGF and is not statistically significant at 5–50 ng/ml NGF. FKSO6 also is neurotrophic with effects most apparent at lower NGF concentrations and a maximal 2.5-fold enhancement of neurite outgrowth evident at 0.5 ng/ml NGF.

There are three principal structural classes of immunosuppressant drugs related in structure to cyclosporin A, FK506, and rapamycin. Though FK506 and cyclosporin A bind to distinct immunophilin proteins, they both act as immunosuppressants by inhibiting calcineurin. Rapamycin bind with very high affinity to FKBP-12, but the drug-immunophilin complex does not in turn bind to calcineurin. Instead, immunosuppressant actions result from the rapamycin-FKBP-12 complex binding to a recently identified and cloned protein designated RAFT-1 (rapamycin and FK506 target) and also designated FRAP (Sabatini and Snyder, 1994; Brown et. al., 1994; Chen et. al., 1994). Because rapamycin binds potently to FKBP-12 but does not inhibit calcineurin, it can serve as an antagonist to FK506. There exist non-immunosuppressive derivatives of rapamycin. One of these, WAY-124,466, a triene derivative of rapamycin, binds with high affinity to FKBP-12 and inhibits rotamase activity, but is devoid of immunosuppressant actions. Cyclosporin A is a large cyclic undecapeptide. The mere addition of a methyl group to an alanine at the 6 position results in an agent that does not inhibit calcineurin and lacks immunosuppressive effects, though it inhibits the rotamase activity of cyclophilin to a similar extent as cyclosporin A (Me CsA ref).

Figure 15:
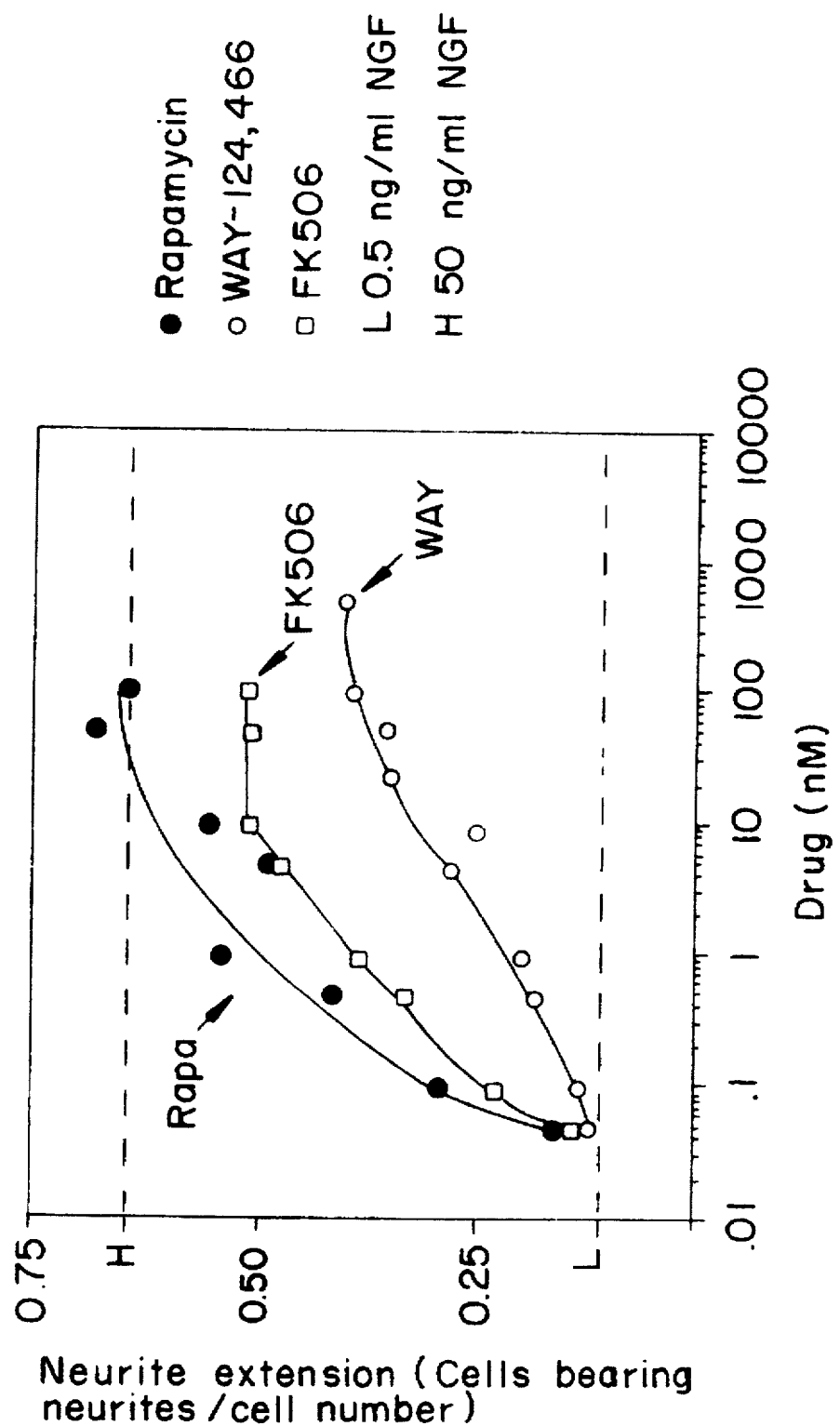
Figure 16A:
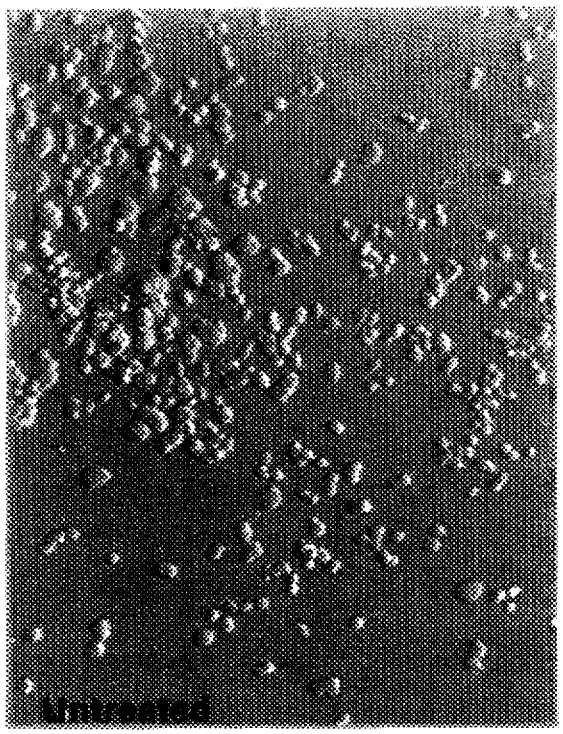
Figure 16B:
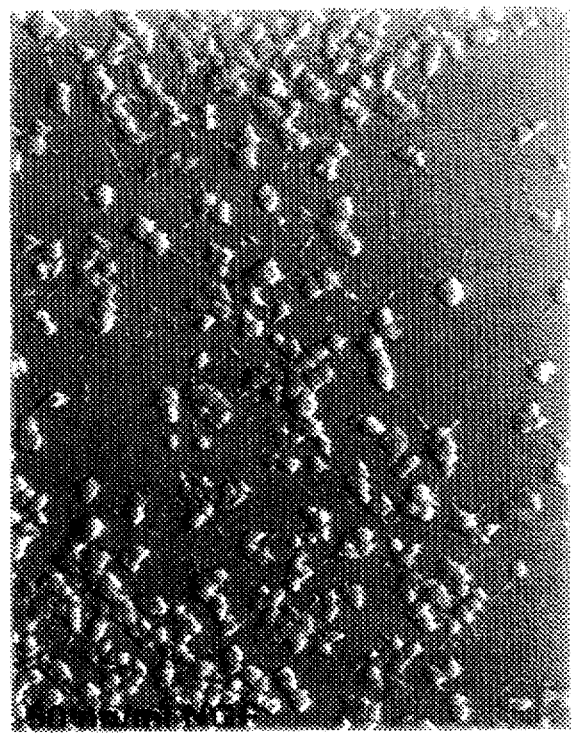
Figure 16C:
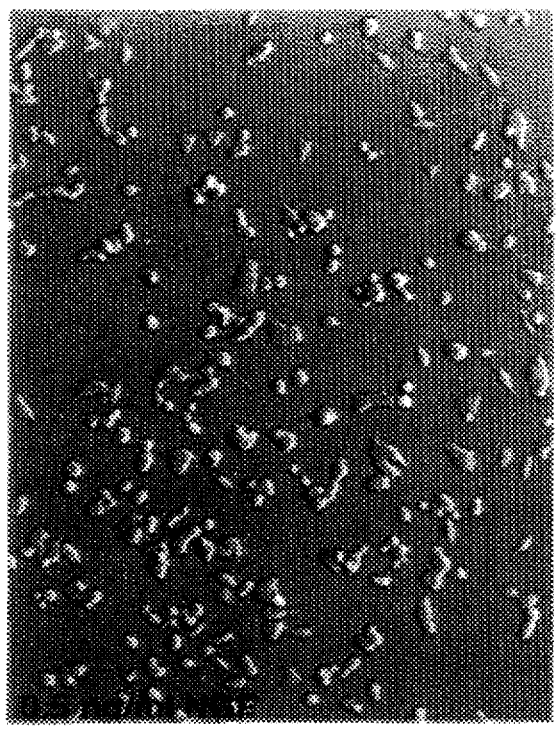
Figure 16D:
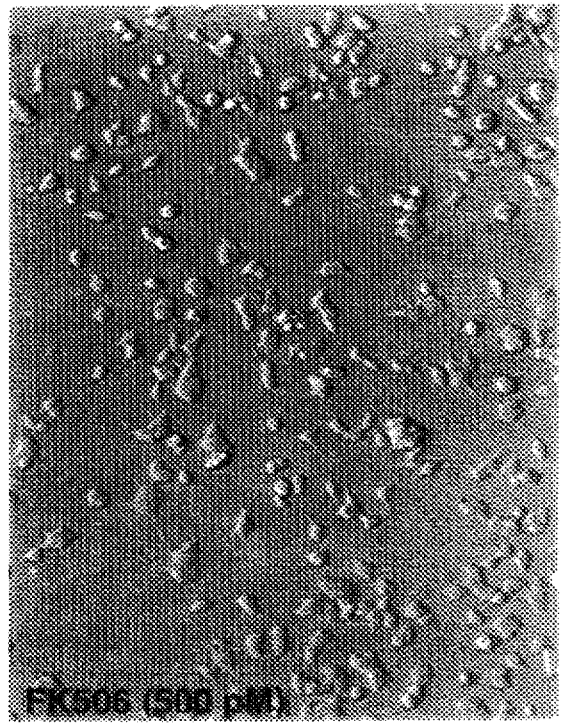
Figure 16E:
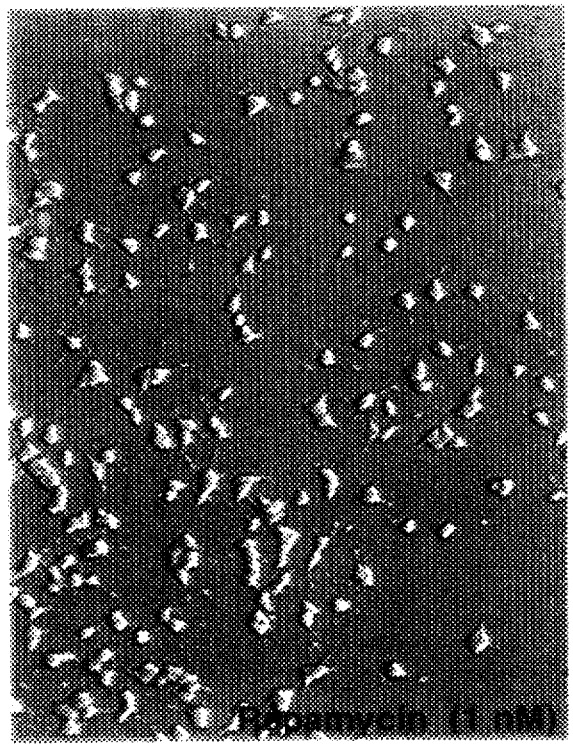
Figure 16F:
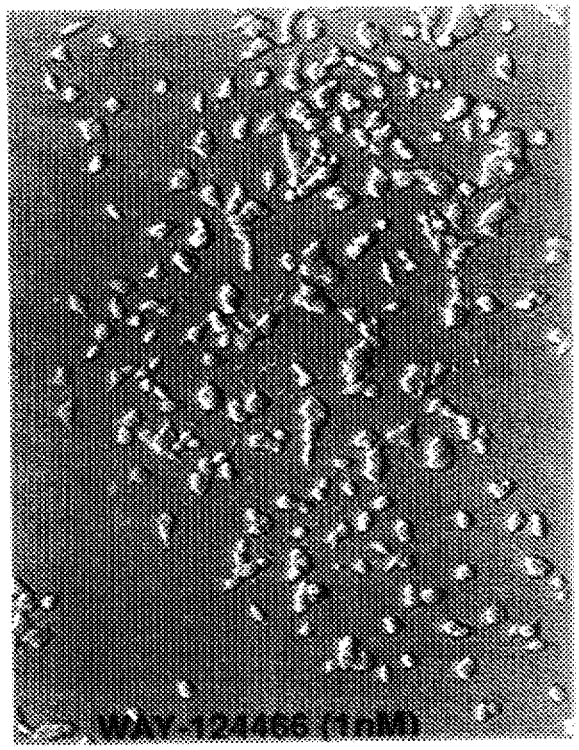

To ascertain whether immunosuppressant activity is required for neurotrophic actions, we compared the neurotrophic effects of FK506, rapamycin and cyclosporin A with non-immunosuppressant WAY-124,466, evaluating a wide range of concentrations on PC-12 cells (FIGS. 15, 16). All studies were done in the presence of 0.5 ng/ml NGF. As observed previously, FK506 very potently stimulates neurite extension with half-maximal stimulation at 0.5 nM and maximal effects at 5–100 nM.

Rapamycin is the most potent agent examined and produces the greatest maximal level of neurite extension. In repeated experiments 50% of maximal extension is evident at about 0.2–0.4 nM while maximal effects are evident at about 10–100 nM. Maximal neurite extension with rapamycin is comparable to maximal effects of 50 ng/ml NGF. WAY-124466 also is neurotrophic, but is less potent and produces a lesser maximal effect than rapamycin. Half-maximal stimulation with WAY-124,466 occurs at about 10 nM and maximal effects occur at 100–1,000 nM. Thus, rapamycin is about 100-fold more potent than WAY-124, 466, resembling its 40-fold greater potency in binding to FKBP-12 (Table II).

Cyclosporin A is substantially less potent than FK506 or rapamycin in stimulating neurite outgrowth, corresponding to its substantially lesser potency in inhibiting rotamase activity. Fifty percent maximal stimulation of neurite outgrowth with cyclosporin A is evident at 50 nM with maximal effects at 100 nM and a decrease in neurite outgrowth at higher concentrations of cyclosporin A. Maximal stimulation with cyclosporin A is about 60% of effects of 50 ng/ml NGF.

The general pattern of process extension is similar with the various immunophilin ligands and with NGF. At concentrations that elicit 50% of maximal effects, NGF (1–5 ng/ml) 40–50% of cells extend processes at least as long as the cell body while 15% extent longer processes, up to 3–5 times the length of the cell body. The pattern is fairly similar with the various drugs examined. Rapamycin and WAY-124, 466 tend to result in a greater number of processes per cell than FK506. Cyclosporin A tends to be intermediate in terms of numbers or processes.

Figure 17A:
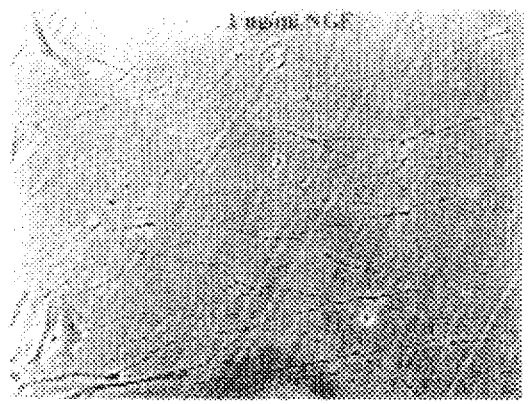
Figure 17B:
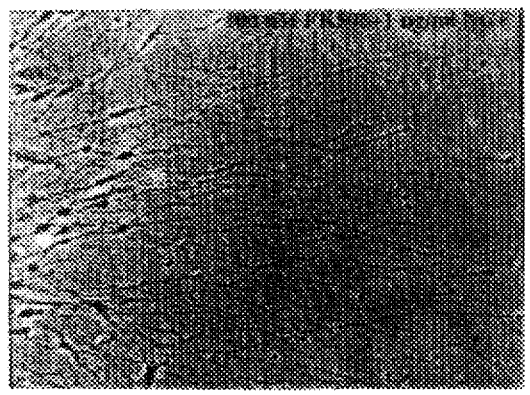
Figure 17C:
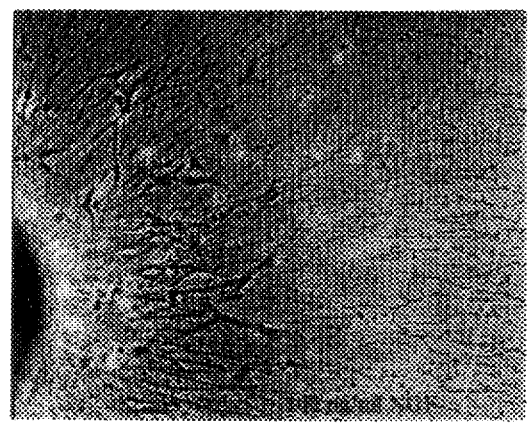
Figure 18:
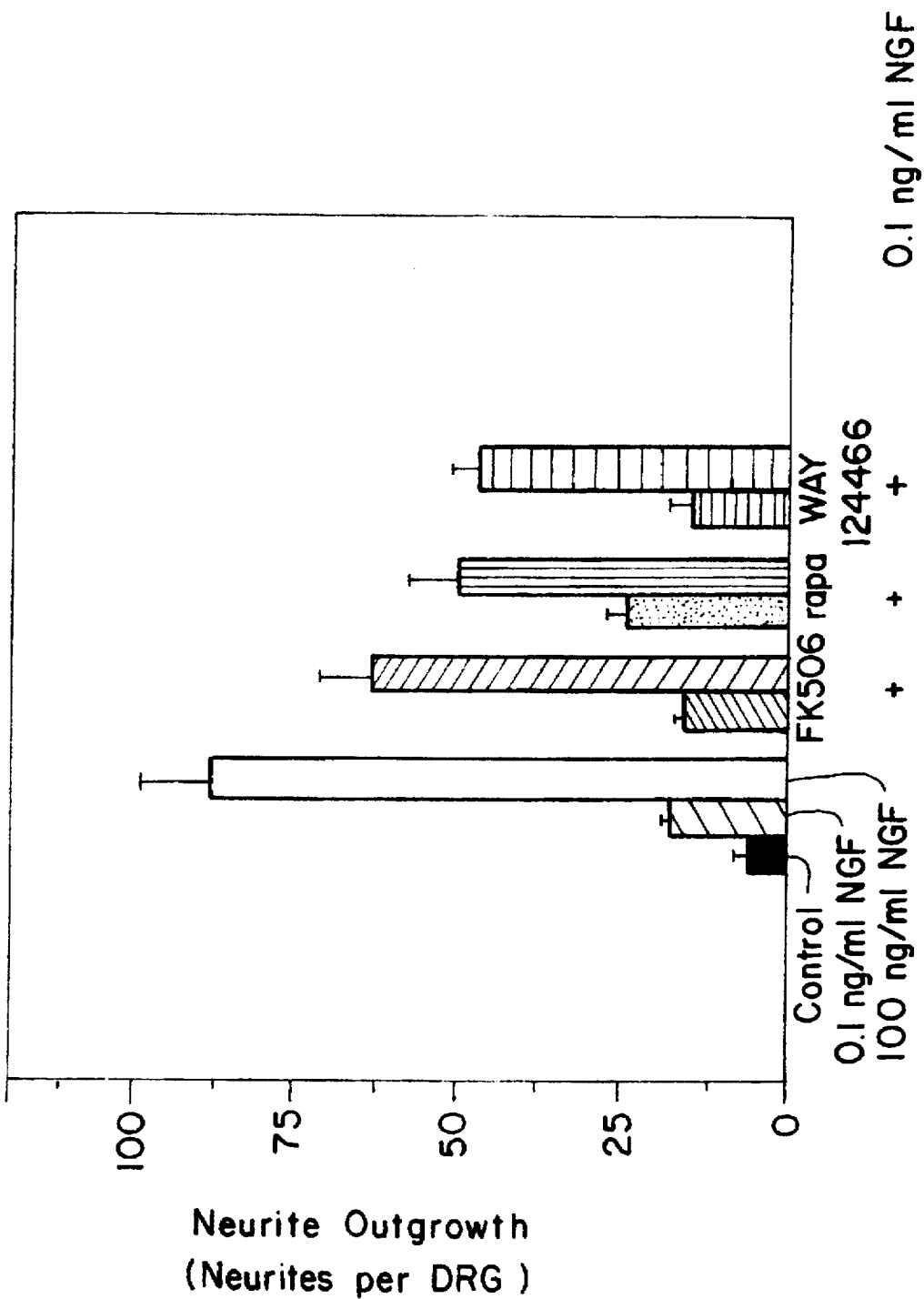

Nerve Extension Elicited in Chick Dorsal Root Ganglia by Non-Immunosuppressive and Immunosuppressive Ligands of Immunophilins In our previous study, we observed neurotrophic effects of immunosuppressant drugs in explants of rat dorsal root ganglia with significant augmentation in nerve outgrowth observed with FK506 concentrations as low as 1 picomolar (Lyons et. al., 1994). In the rat ganglia neurotrophic effects were observed with FK506 even in the absence of NGF. In the present study we have employed explants of chick dorsal root ganglia, which are easier to employ in studies of nerve outgrowth. In the absence of added NGF, we observe minimal effects of immunophilin ligand drugs. The chick cells are more sensitive to NGF than PC-12 cells so that we employ 0.1 ng/ml NGF to produce minimal neurite outgrowth and to demonstrate neurotrophic actions of immunophilin ligands (FIG. 17,18).

Dorsal root ganglion were dissected from chick embryos of ten day gestation. Whole ganglin explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRG's were treated with various concentrations of nerve growth factor, immunophilin ligands or combinations of NGF plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The relative potencies of the various immunophilin ligands in stimulating nerve outgrowth in the ganglia are similar to their relative potencies in PC-12 cells. Thus, rapamycin is the most potent agent with an $EC_{50}$ of 1 nM, 10-fold more potent than WAY-124,466, while FK506 displays an $EC_{50}$ of 1–2 nM.

The maximal increase in the number of processes, their length and branching is quite similar at maximally effective contractions of the immunophilin ligands and of NGF (100 ng/ml). With progressively increasing concentrations of the various drugs, one observes a larger number of processes, more extensive branching and a greater length of individual processes.

We evaluated the potencies of drugs in binding to FKBP-12 by examining inhibition of $^3$H-FK506 binding to recombinant FKBP-12. There is a striking parallel between affinities of drugs for FKBP-12 and their potencies in stimulating neurite outgrowth and inhibiting rotamase activity. Clearly, stimulation of nerve outgrowth is unrelated to calcineurin inhibition. Calcineurin inhibition fits well with immunosuppressant actions. WAY-124,466 is not immunosuppressive and fails to inhibit calcineurin. Rapamycin is a potent immunosuppressant, but the rapamycin-FKBP-12 complex binds to RAFT-1 to initiate immunosuppressive processes (Sabatini and Snyder, 1994; Snyder and Sabatini, 1995). The results are set forth in Table 2.

TABLE 2

IMMUNOPHILIN LIGAND NEUROTROPHISM PARALLELS INHIBITION OF ROTAMASE, NOT CALCINEURIN

| DRUG | [$^3$H]-FK506-FKBP12 ($IC_{50}$) | CALCINEURIN INHIBITION | ROTAMASE ($K_i$) | NEURITE OUTGROWTH ($ED_{50}$) |
|---|---|---|---|---|
| FK506 | 0.6 nM | YES | 0.4 nM | 0.5 nM |
| Rapamycin | 0.5 nM | NO | 0.2 nM | 0.5 nM |
| WAY-124466 | 10.0 nM | NO | 12.0 nM | 10 nM |

TABLE 2-continued

IMMUNOPHILIN LIGAND NEUROTROPHISM PARALLELS INHIBITION OF ROTAMASE, NOT CALCINEURIN

| DRUG | [³H]-FK506-FKBP12 (IC$_{50}$) | CALCINEURIN INHIBITION | ROTAMASE NEURITE OUTGROWTH | |
|---|---|---|---|---|
| | | | (K$_i$) | (ED$_{50}$) |
| Cyclosporin A (CsA) | None | YES | 20 nM | 50 nM |

We compared the ability of non-immunosuppressive immunophilin ligands to promote neurite outgrowth in chick dorsal root ganglion explant cultures (Table 3). Each of these compounds is incapable of inhibiting calcineurin, but they interact with the immunophilin FKBP-12 to inhibit it's rotamase activity with the various inhibitory constants listed in Table 3. The ability of these compounds to promote neurite outgrowth in the DRG's correlates well with their ability to inhibit the rotamase activity of FKBP-12.

TABLE 3

IMMUNOPHILIN LIGAND NEUROTROPHISM PARALLELS INHIBITION OF ROTAMASE, NOT CALCINEURIN

| Drug | [³H]-FK506-FKBP12 (IC$_{50}$) | Calcineurin Inhibition | Rotamase (K$_i$) | Neurite Outgrowth (ED$_{50}$) |
|---|---|---|---|---|
| Example 12 | 8 µM | NO | 250 nM | 300 nM |
| Example 13 | 4 µM | NO | 25 nM | 80 nM |

The very close correlation between the potencies of drugs in binding to immunophilins, inhibiting their rotamase activity and stimulating neurite outgrowth implies that inhibition of rotamase activity is responsible for neurotrophic effects of the drugs. The extraordinarily high potency of the drugs in stimulating neurite outgrowth and in binding to immunophilins makes it most unlikely that any other target could account for the neurotrophic effects. It is conceivable that a biological activity of immunophilins other than rotamase could be influenced by the drugs to mediate neurotrophic actions. However, no such activity has yet been reported.

Because of the extraordinary potency of the drugs and the close correlation between rotamase inhibition and neurotrophic actions, we conclude that rotamase inhibition is likely involved in neurotrophic effects. A number of proteins have been reported as substrates for the rotamase activity of immunophilins including collagen (Steinmann et. al., 1991) and transferrin (Lodish and King, 1991). Recently highly purified preparations of ryanodine receptor and the IP-3 receptor, prominent intracellular calcium channels have been reported to exist in a complex with FKBP-12. Dissociation of FKBP-12 from these complexes causes the calcium channel to become "leaky" (Cameron et. al., 1995) Calcium fluxes are involved in neurite extension so that the IP-3 receptor and the ryanodine receptor might be involved in the neurotrophic effects of drugs. Since the drugs bind to the same site on FKBP-12 as the IP-3 receptor or the ryanodine receptor, one would have to postulate that the drugs displace the channels from FKBP-12. No interaction between these calcium channels in cyclophilin has been reported so that this model would not explain the neurotrophic actions of cyclosporin A.

The neurotrophic actions of the drugs studied here are exerted at extremely low Concentrations indicating potencies comparable to those of neurotrophic proteins such as brain derived growth factor, neurotropin-3 and neurotrophic growth factor.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

Illustrative pipecolic acid derivative compounds which can be used for the purposes of this invention include:

EXAMPLE 1

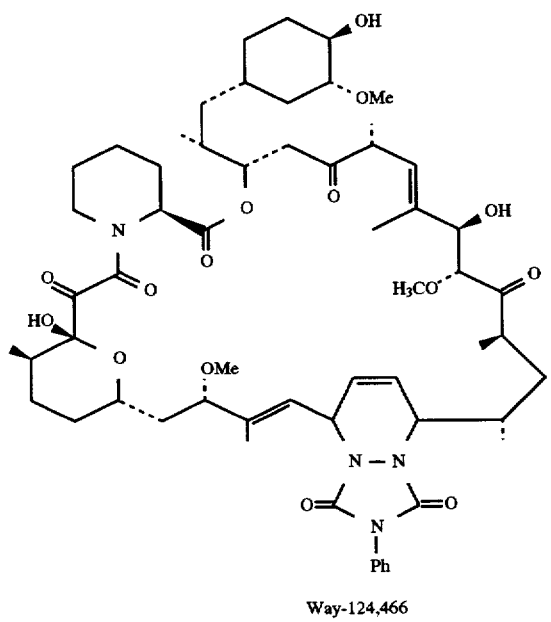

Way-124,466

This exemplary pipecolic acid derivative compound is disclosed by Ocain et al., *Biochemical and Biophysical Research Communications*, Vol. 192, No. 3, 1993. The compound was synthesized at Wyeth-Ayerst by Dr. Phil Hughes by reaction of 4-phenyl-1,2,4-triazoline-3,5-dione with rapamycin.

EXAMPLE 2

21

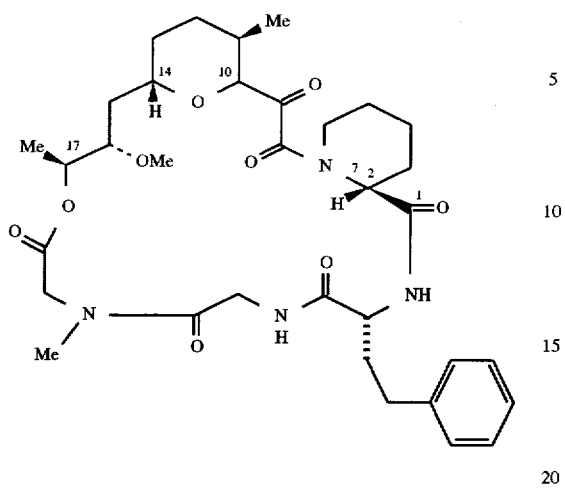

This pipecolic acid derivative compound is disclosed by Chakraborty et al., *Chemistry and Biology*, March 1995, 2:157–161.

EXAMPLES 3-5

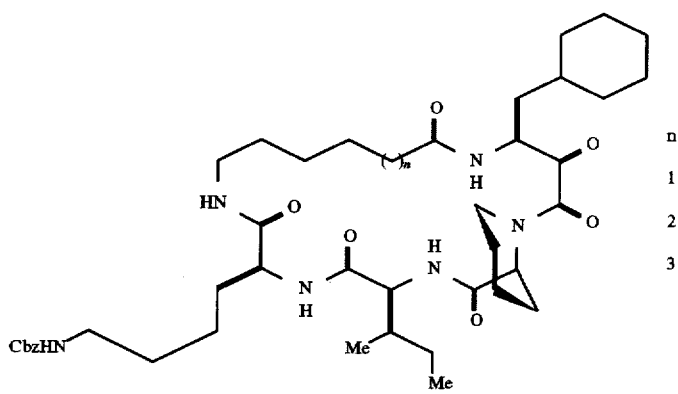

EXAMPLES 6-9

Exemplary pipecolic acid derivative compounds are disclosed by Wang et al., *Bioorganic and Medicinal Chemistry Letters*, Vol. 4, No. 9, pp. 1161–1166, 1994, particularly compounds 2a–2d and are incorporated herein by reference.

EXAMPLE 10

22

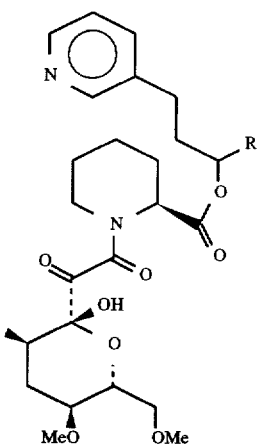

This exemplary pipecolic acid derivative, compound 10, is disclosed by Birkenshaw et al., *Bioorganic & Medicinal Chemistry Letters*, Vol. 4, No. 21, pp. 2501–2506, 1994, and is incorporated herein by reference.

EXAMPLES 11-21

Exemplary pipecolic acid derivative compounds are disclosed by Holt et al., *J. Am. Chem. Soc.*, 1993, 115, 9925–9938, particularly compounds 4–14, and are incorporated herein by reference.

EXAMPLES 22-30

Exemplary pipecolic acid derivative compounds are disclosed by Caffery et al., *Bioorganic & Medicinal Chemistry Letters*, Vol. 4, No. 21, pp. 2507–2510, 1994, and are incorporated herein by reference.

Exemplary pipecolic acid derivative compounds are disclosed by Ikeda et al., *J. Am. Chem. Soc.*, 1994, 116, 4143–4144, and are incorporated herein by reference.

EXAMPLE 31

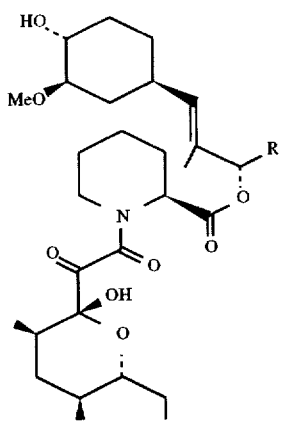

This exemplary pipecolic acid derivative, compound 31, is disclosed by Teague et al., *Bioorganic & Medicinal Chemistry Letters*, Vol. 3, No. 10, pp. 1947–1950, 1993 and is incorporated herein by reference.

EXAMPLES 32–34

Exemplary pipecolic acid derivative compounds are disclosed by Yamashita et al., *Bioorganic & Medicinal Chemistry Letters*, Vol. 4., No. 2, pp. 325–328, 1994, particularly, compounds 11, 12, and 19, and are incorporated herein by reference.

EXAMPLE 35–55

Exemplary pipecolic acid derivatives are disclosed by Holt et al., *Bioorganic & Medicinal Chemistry Letters*, Vol. 4, No. 2, pp. 315–320, 1994, particularly, compounds 3–21, and 23–24, and are incorporated herein by reference.

EXAMPLES 56–68

Exemplary pipecolic acid derivative compounds are disclosed by Holt et al., *Bioorganic & Medicinal Chemistry Letters*, Vol. 3, No. 10, pp. 1977–1980, 1993, particularly compounds 3–15 and are incorporated by reference herein.

EXAMPLES 69–83

Exemplary compounds of the present invention are disclosed by Hauske et al., *J. Med. Chem.* 1992, 35, 4284–4296, particularly compounds 6, 9–10, 21–24, 26, 28, 31–32, and 52–55, and are incorporated herein by reference.

EXAMPLE 84

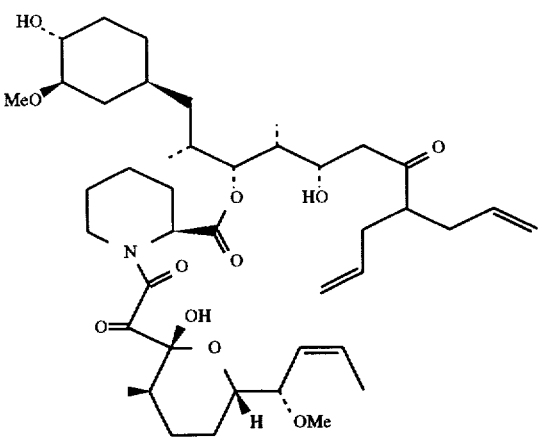

SLB506

This exemplary pipecolic acid derivative is disclosed by Teague et al., *Bioorganic & Med. Chem. Letters*, Vol. 4, No. 13, pp. 1581–1584, 1994, and is incorporated herein by reference.

EXAMPLES 85–88

Exemplary pipecolic acid derivative compounds are disclosed by Stocks et al., *Bioorganic & Med. Chem. Letters*, Vol. 4, No. 12, pp. 1457–1460, 1994, particularly compounds 2, 15–17 and are incorporated herein by reference.

SCHEME 1

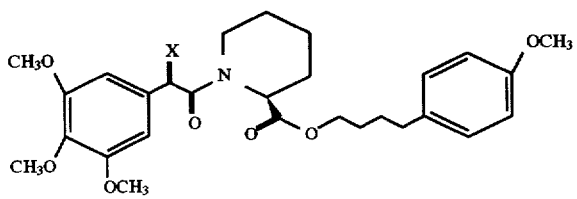

| EXAMPLE/COMPOUND | STRUCTURE |
|---|---|
| 6 | X = $H_2$ |
| 7 | X = $CH_2$ |
| 8 | X = H, $CH_3$ |
| 9 | X = O |

SCHEME 2
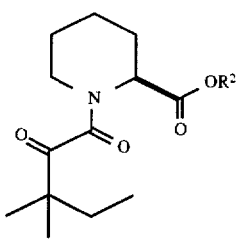
| EXAMPLE/ COMPOUNDS NO. | R₂ |
|---|---|
| 11 | 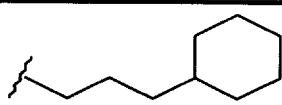 |
| 12 | 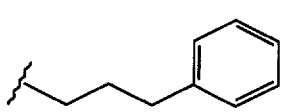 |
| 13 | 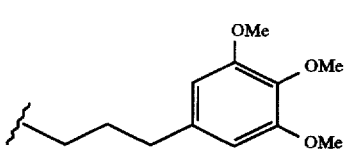 |
| 14 | 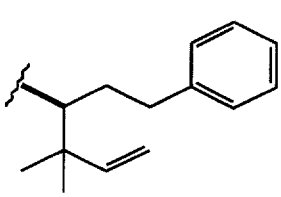 |
| 15 | 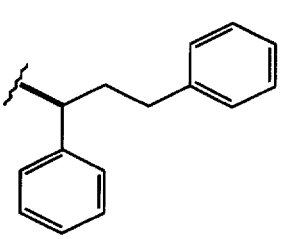 |
| 16 | 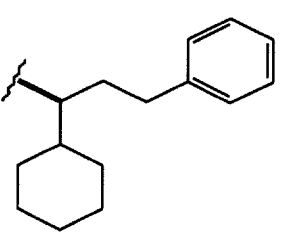 |
-continued
SCHEME 2
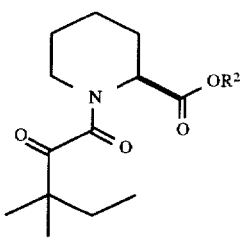
| EXAMPLE/ COMPOUNDS NO. | R₂ |
|---|---|
| 17 | 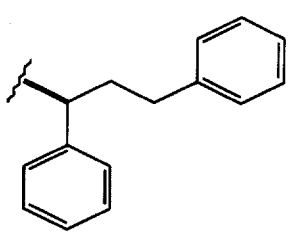 |
| 18 | 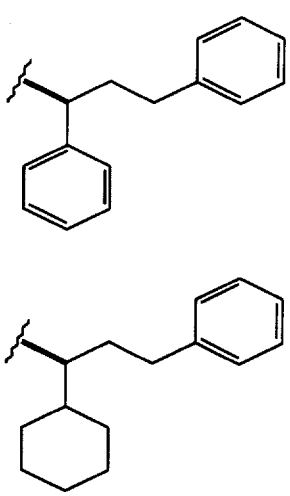 |

SCHEME 3
| EXAMPLE/COMPOUND NO. | STRUCTURE |
|---|---|
| 19 | 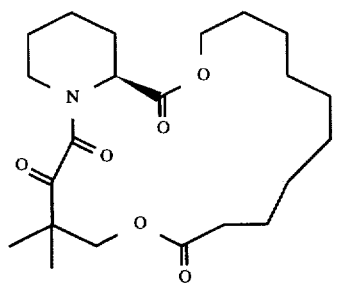 |
| 20 | 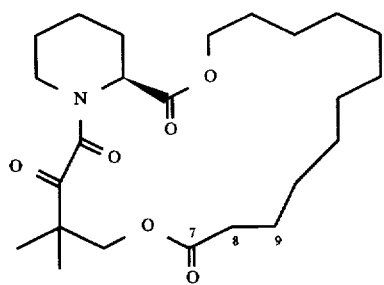 |
| 21 | 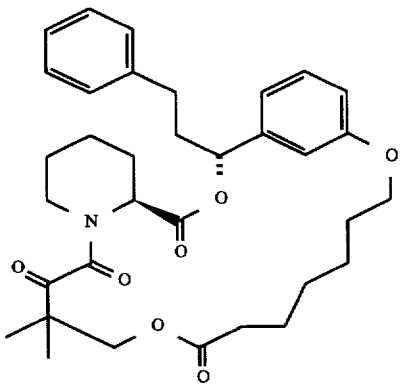 |

TABLE 1
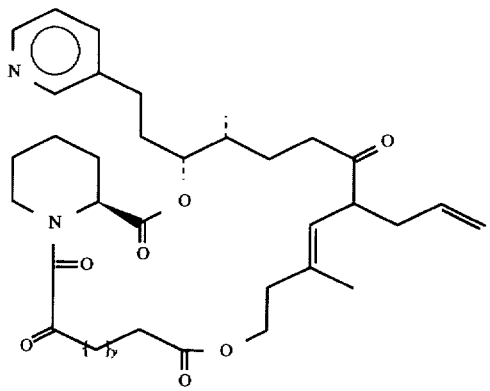
| Example/Compound No. | Structure |
|---|---|
| 22 | y = 1 |
| 23 | y = 2 |
| 24 | y = 3 |
TABLE 2
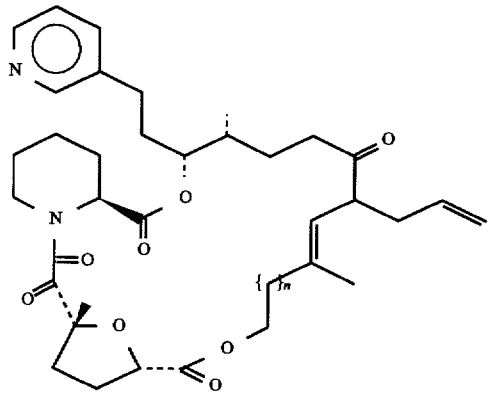
| Example/Compound No. | Structure |
|---|---|
| 25 | n = 1 |
| 26 | n = 2 |
| 27 | n = 3 |
TABLE 3
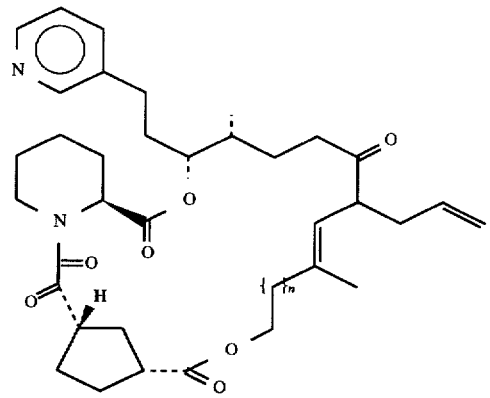
| Example/Compound No. | Structure |
|---|---|
| 28 | n = 1 |
| 29 | n = 2 |
| 30 | n = 3 |
SCHEME 5
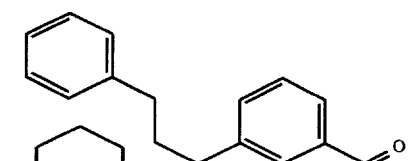
| EXAMPLE/COMPOUND NO. | STRUCTURE |
|---|---|
| 32 | R = phenyl |
| 33 | R = N(allyl)$_2$ |
| 34 | 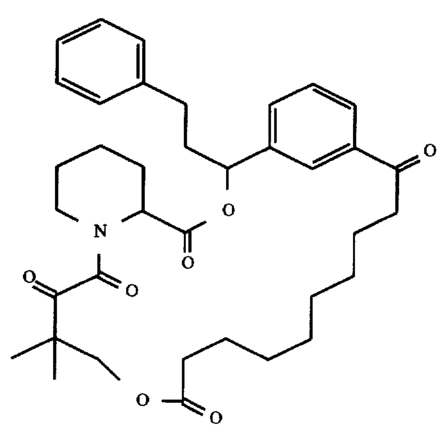 |
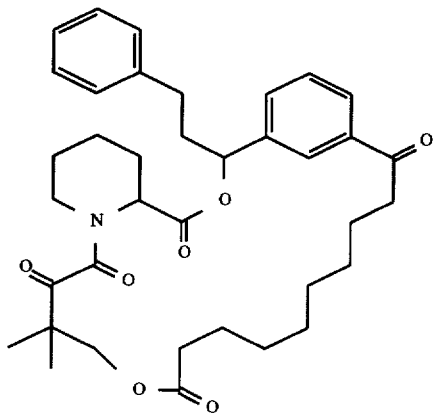

TABLE 1
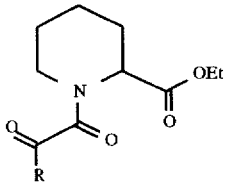
| Example/Compound No. | Structure R |
|---|---|
| 35 | 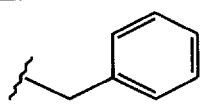 |
| 36 |  Me |
| 37 | 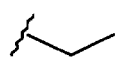 |
| 38 | 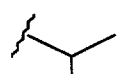 |
| 39 | 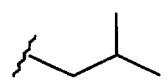 |
| 40 | 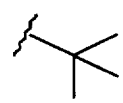 |
| 41 | 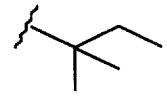 |
| 42 | 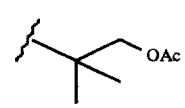 OAc |
| 43 | 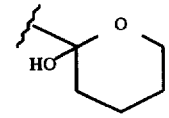 |
| 44 | 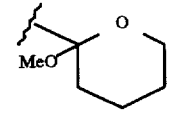 |
TABLE 1-continued
| Example/Compound No. | Structure R |
|---|---|
| 45 | 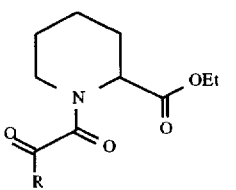 |
| 46 | 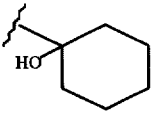 |
| 47 | 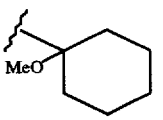 |
| 48 | 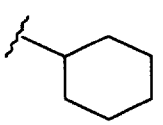 |
| 49 | 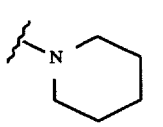 |
| 50 | 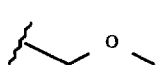 |

TABLE 2
| Example/Compound No. | Structure |
|---|---|
| 51 | 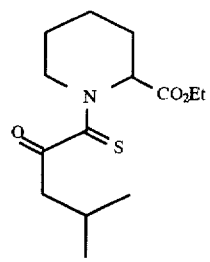 |
| 52 | 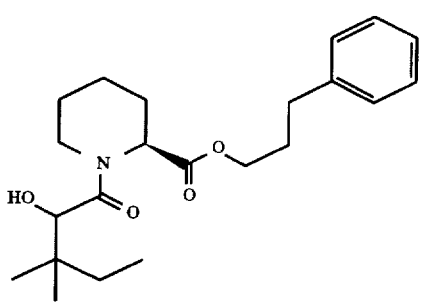 |
| 53 | 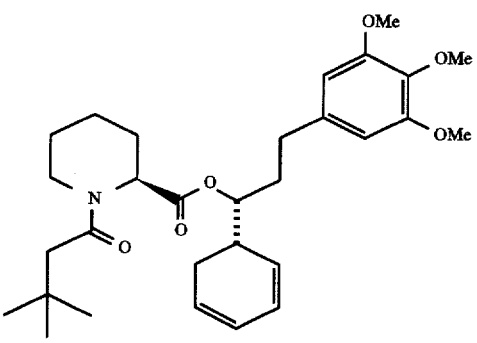 |
| 54 | 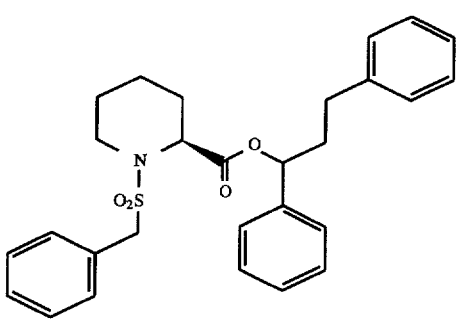 |

TABLE 2-continued
| Example/Compound No. | Structure |
|---|---|
| 55 | 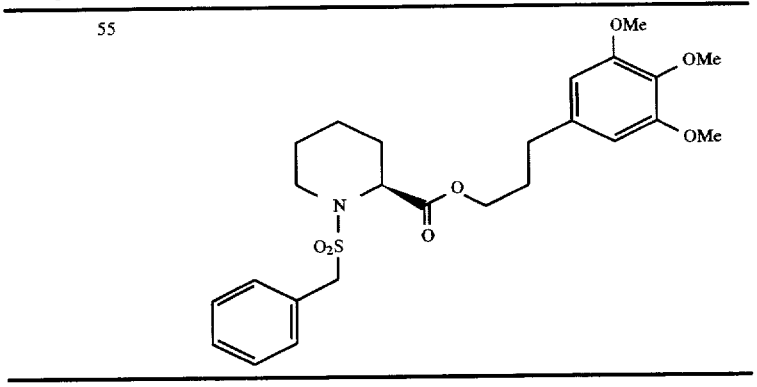 |
TABLE 1
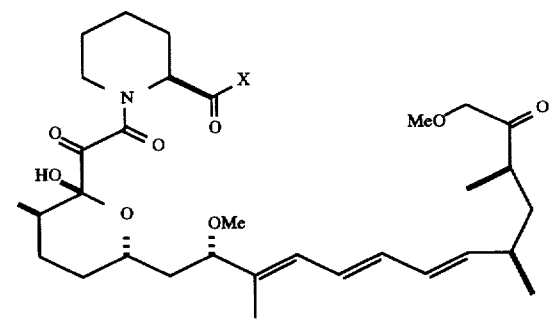
| 56 | x = OH |
| 57 | x = OMe |
| 58 | x = OiPr |
| 59 | x = OBn |
| 60 | x = OCH MePh |
| 61 | x = OCH₂CHCHPh |
| 62 | x = OCH₂CH₂CH₂(3,4-OMe₂)Ph |
| 63 | x = NHBn |
| 64 | x = NHCH₂CH₂CH₂Ph |
TABLE 2
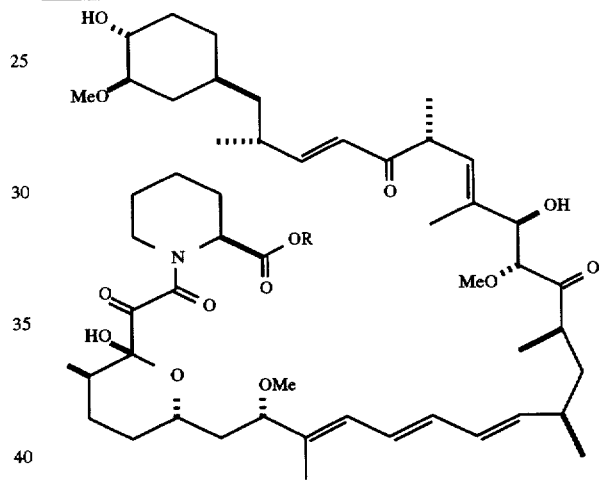
| 65 | R = Me |
| 66 | R = Bn |
TABLE 3
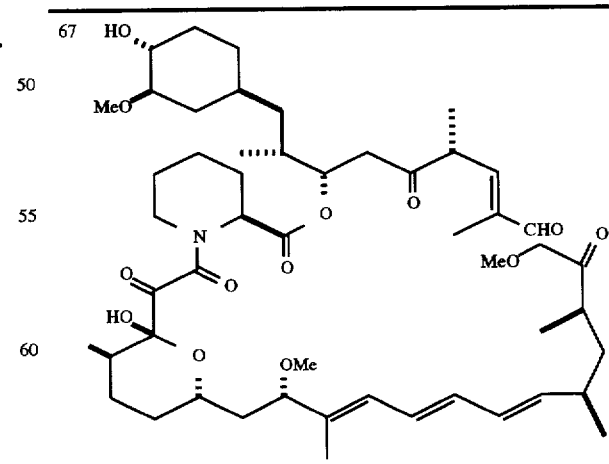
67

TABLE 3-continued
| | |
|---|---|
| 68 | 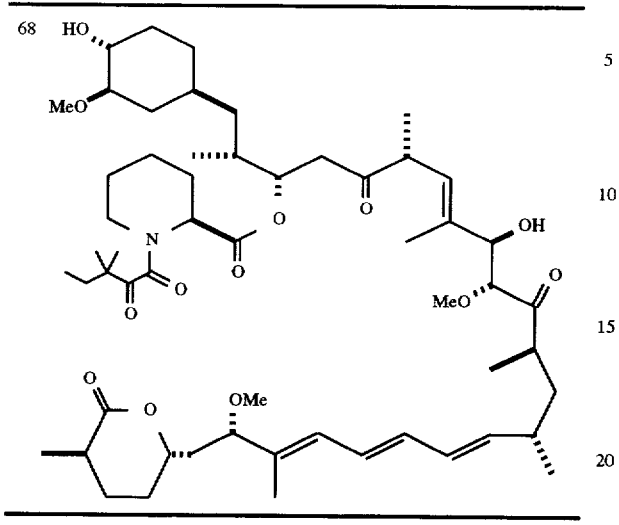 |
TABLE 1
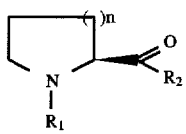
Example/Compound No. Structure
| 69 | 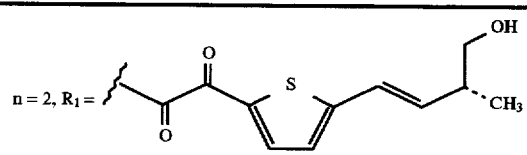 |
|---|---|
| | $R_2$ = Phe-o-tert-butyl |
| 70 | 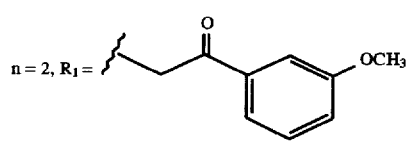 |
| | $R_2$ = Phe-o-tert-butyl |

TABLE 2

| | |
|---|---|
| 71 | $R_1$ = m-OCH$_3$Ph; $R_3^1$ = Val-o-tert-butyl |
| 72 | $R_1$ = m-OCH$_3$Ph; $R_3^1$ = Leu-o-tert-butyl |
| 73 | $R_1$ = m-OCH$_3$Ph; $R_3^1$ = Ileu-o-tert-butyl |
| 74 | $R_1$ = m-OCH$_3$Ph; $R_3^1$ = hexahydro-Phe-o-tert-butyl |
| 75 | $R_1$ = m-OCH$_3$Ph; $R_3^1$ = allylalanine-o-tert-butyl |
| 76 | $R_1$ = B-naphthyl; $R_3^1$ = Val-o-tert-butyl |

TABLE 3

| Example/Compound No. | Structure |
|---|---|
| 77 | $R_1$ = CH$_2$(CO)-m-OCH$_3$PH<br>$R_4^1$ = CH$_2$Ph<br>$R_5^1$ = OCH$_3$ |
| 78 | $R_1$ = CH$_2$(CO)-B-naphthyl<br>$R_4^1$ = CH$_2$Ph<br>$R_5^1$ = OCH$_3$ |

TABLE 4

| Example/Compound No. | Structure |
|---|---|
| 79 | $R_1$ = m-OCH$_3$Ph<br>X = trans-CH=CH |

TABLE 4-continued

| Example/Compound No. | Structure |
|---|---|
| 80 | $R_4^1$ = H<br>Y = OC(o)Ph<br>$R_1$ = m-OCH$_3$Ph<br>X = trans-CH=CH |
| 81 | $R_4^1$ = H<br>Y = OC(o)CF$_3$<br>$R_1$ = m-OCH$_3$Ph<br>X = trans-CH=CH |
| 82 | $R_4^1$ = —<br>Y = —<br>$R_1$ = m-OCH$_3$Ph<br>X = trans-CH=CH<br>$R_4^1$ = H<br>Y = OCH$_2$CH=CH$_2$ |
| 83 | $R_1$ = m-OCH$_3$Ph<br>X = C=O<br>$R_4^1$ = H<br>Y = Ph |

TABLE 1

85

TABLE 2

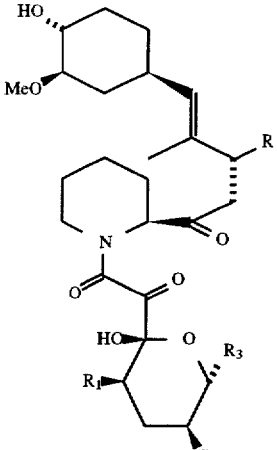

| | |
|---|---|
| 86 | $R_1$ = H, $R_2$ = OMe $R_3$ = $CH_2OMe$ |
| 87 | $R_1$ = H, $R_2$ = $R_3$ = H |
| 88 | $R_1$ = Me, $R_2$ = $R_3$ = H |

| Compound No. | Name of Species |
|---|---|
| 6 | 4-(4-methoxyphenyl)butyl (2S)-1-[2-(3,4,5-trimethoxyphenyl)acetyl]hexahydro-2-pyridinecarboxylate |
| 7 | 4-(4-methoxyphenyl)butyl (2S)-1-[2-(3,4,5-trimethoxyphenyl)acryloyl]hexahydro-2-pyridinecarboxylate |
| 8 | 4-(4-methoxyphenyl)butyl (2S)-1-[2-(3,4,5-trimethoxyphenyl)propanoyl]hexahydro-2-pyridinecarboxylate |
| 9 | 4-(4-methoxyphenyl)butyl (2S)-1-[2-oxo-2-(3,4,5-trimethoxyphenyl)acetyl]hexahydro-2-pyridinecarboxylate |
| 11 | 3-cyclohexylpropyl (2S)-1-(3,3-dimethyl-2-oxopentanoyl)hexahydro-2-pyridinecarboxylate |
| 12 | 3-phenylpropyl (2S)-1-(3,3-dimethyl-2-oxopentanoyl)hexahydro-2-pyridinecarboxylate |
| 13 | 3-(3,4,5-trimethoxyphenyl)propyl (2S)-1-(3,3-dimethyl-2-oxopentanoyl)hexahydro-2-pyridinecarboxylate |
| 14 | (1R)-2,2-dimethyl-1-phenethyl-3-butenyl (2S)-1-(3,3-dimethyl-2-oxopentanoyl)hexahydro-2-pyridinecarboxylate |
| 15 | (1R)-1,3-diphenylpropyl (2S)-1-(3,3-dimethyl-2-oxopentanoyl)hexahydro-2-pyridinecarboxylate |
| 16 | (1R)-1-cyclohexyl-3-phenylpropyl (2S)-1-(3,3-dimethyl-2-oxopentanoyl)hexahydro-2-pyridinecarboxylate |
| 17 | (1S)-1,3-diphenylpropyl (2S)-1-(3,3-dimethyl-2-oxopentanoyl)hexahydro-2-pyridinecarboxylate |
| 18 | (1S)-1-cyclohexyl-3-phenylpropyl (2S)-1-(3,3-dimethyl-2-oxopentanoyl)hexahydro-2-pyridinecarboxylate |
| 19 | (22aS)-15,15-dimethylperhydropyrido[2,1-c][1,9,4]dioxazacyclononadecine-1,12,16,17-tetraone |
| 20 | (24aS)-17,17-dimethylperhydropyrido[2,1-c][1,9,4]dioxazacyclohenicosine-1,14,18,19-tetraone |
| 22 | (3R,4R,23aS)-8-allyl-4,10-dimethyl-3-[2-(3-pyridyl)ethyl]-1,3,4,5,6,7,8,11,12,15,16,17,18,20,21,22,23,23a-octadecahydro-14H-pyrido[2,1-c][1,10,4]dioxazacycloicosine-1,7,14,17,18-pentaone |
| 23 | (3R,4R,24aS)-8-allyl-4,10-dimethyl-3-[2-(3-pyridyl)ethyl]-1,3,4,5,6,7,8,11,12,14,15,16,17,18,19,21,22,23, 24,24a-icosahydropyrido[2,1-c][1,11,4]dioxazacyclohenicosine-1,7,14,18,19-pentaone |
| 24 | (3R,4R,25aS)-8-allyl-4,10-dimethyl-3-[2-(3-pyridyl)ethyl]-1,3,4,5,6,7,8,11,12,15,16,17,18,19,20,22,23, 24,25,25a-icosahydro-14H-pyrido[2,1-c][1,12,4]dioxazacyclodocosine-1,7,14,19,20-pentaone |
| 32 | (1R)-1-(3-benzoylphenyl)-3-phenylpropyl (1R)-2-(3,3-dimethyl-2-oxopentanoyl)cyclohexane-1-carboxylate |
| 33 | (1R)-1-[3-(diallylcarbamoyl)phenyl]-3-phenylpropyl (1R)-2-(3,3-dimethyl-2-oxopentanoyl)cyclohexane-1-carboxylate |
| 35 | ethyl 1-(2-oxo-3-phenylpropanoyl)-2-piperidinecarboxylate |
| 36 | ethyl 1-pyruvoyl-2-piperidinecarboxylate |
| 37 | ethyl 1-(2-oxobutanoyl)-2-piperidinecarboxylate |
| 38 | ethyl 1-(3-methyl-2-oxobutanoyl)-2-piperidinecarboxylate |
| 39 | ethyl 1-(4-methyl-2-oxopentanoyl)-2-piperidinecarboxylate |
| 40 | ethyl 1-(3,3-dimethyl-2-oxobutanoyl)-2-piperidinecarboxylate |
| 41 | ethyl 1-(3,3-dimethyl-2-oxopentanoyl)-2-piperidinecarboxylate |
| 42 | 4-[2-(ethyloxycarbonyl)piperidino]-2,2-dimethyl-3,4-dioxobutyl acetate |
| 43 | ethyl 1-[2-(2-hydroxytetrahydro-2H-2-pyranyl)-2-oxoacetyl]-2-piperidinecarboxylate |
| 44 | ethyl 1-[2-(2-methoxytetrahydro-2H-2-pyranyl)-2-oxoacetyl]-2-piperidinecarboxylate |
| 45 | ethyl 1-[2-(1-hydroxycyclohexyl)-2-oxoacetyl]-2-piperidinecarboxylate |
| 46 | ethyl 1-[2-(1-methoxycyclohexyl)-2-oxoacetyl]-2-piperidinecarboxylate |
| 47 | ethyl 1-(2-cyclohexyl-2-oxoacetyl)-2-piperidinecarboxylate |
| 48 | ethyl 1-(2-oxo-2-piperidinoacetyl)-2-piperidinecarboxylate |
| 49 | ethyl 1-[2-(3,4-dihydro-2H-6-pyranyl)-2-oxoacetyl)-2-piperidinecarboxylate |
| 50 | ethyl 1-(2-oxo-2-phenylacetyl)-2-piperidinecarboxylate |
| 51 | ethyl 1-(4-methyl-2-oxo-1-thioxopentyl)-2-piperidinecarboxylate |
| 52 | 3-phenylpropyl 1-(2-hydroxy-3,3-dimethylpentanoyl)-2-piperidinecarboxylate |
| 53 | (1R)-1-phenyl-3-(3,4,5-trimethoxyphenyl)propyl 1-(3,3-dimethylbutanoyl)-2-piperidinecarboxylate |
| 54 | (1R)-1,3-diphenylpropyl 1-(benzylsulfonyl)-2-piperidinecarboxylate |
| 55 | 3-(3,4,5-trimethoxyphenyl)propyl 1-(benzylsulfonyl)-2-piperidinecarboxylate |
| 56 | 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylic acid |
| 57 | methyl 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |
| 58 | isopropyl 1-(2-[(2R,3R,6S)-6-[(2S,3E,5E,7E,9S,11R)-2,13-dimethyl-12-oxo-3,5,7-tridecatrienyl]-2-hydroxy-3-methyltetrahydro-2H-2-pyranyl)-2-oxoacetyl)-2-piperidinecarboxylate |
| 59 | benzyl 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |
| 60 | 1-phenylethyl 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |

-continued

| Compound No. | Name of Species |
|---|---|
| 61 | (Z)-3-phenyl-2-propenyl 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |
| 62 | 3-(3,4-dimethoxyphenyl)propyl 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |
| 63 | N2-benzyl-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate |
| 64 | N2-(3-phenylpropyl)-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate. |

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of treating a neurological disorder in an animal, comprising:
   administering to an animal an effective amount of a non-immunosuppressive pipecolic acid derivative having an affinity for FKBP-type immunophilins to stimulate growth of damaged peripheral nerves or to promote neuronal regeneration, wherein the FKBP-type immunophilin exhibits rotamase activity and the non-immunosuppressive pipecolic acid derivative inhibits said rotamase activity of the immunophilin.

2. The method of claim 1, wherein the neurological disorder is selected from the group consisting of peripheral neuropathies cause by physical injury or disease state, physical damage to the brain, physical damage to the spinal cord, stroke associated with brain damage, and neurological disorders relating to neurodegeneration.

3. The method of claim 2, wherein the neurological disorder is selected from the group consisting of Alzheimer's Disease, Parkinson's Disease, and amyotrophic lateral sclerosis.

4. The method of claim 1, wherein the non-immunosuppressive pipecolic acid derivative is Way-124,666.

5. The method of claim 1, wherein the non-immunosuppressive pipecolic acid derivative is Rap-Pa.

6. The method of claim 1, wherein the non-immunosuppressive pipecolic acid derivative is SLB-506.

7. The method of claim 1, wherein the non-immunosuppressive pipecolic acid derivative is selected from the group consisting of 6 4-(4-methoxyphenyl)butyl(2S)-1-[2-(3,4,5-trimethoxyphenyl)acetyl]hexahydro-2-pyridinecarboxylate, 7 4-(4-methoxyphenyl)butyl(2S)-1-[2-(3,4,5-trimethoxphenyl)acryloyl]hexahydro-2-pyridinecarboxylate, 8 4-(4-methoxyphenyl)butyl(2S)-1-[2-(3,4,5-trimethoxyphenyl)propanoyl]hexahydro-2-pyridinecarboxylate, 9 4-(4-methoxyphenyl)butyl(2S)-1-[2-oxo-2-(3,4,5-trimethoxyphenyl)acetyl]hexahydro-2-pyridinecarboxylate, 11 3-cyclohexylpropyl(2S)-1-(3,3-dimethyl-2-oxopentanoyl)hexahydro-2-pyridinecarboxylate, 12 3-phenylpropyl(2S)-1-(3,3-dimethyl-2-oxopentanoyl) hexahydro-2-pyridinecarboxylate, 13 3-(3,4,5-trimethoxyphenyl)propyl(2S)-1-(3,3-dimethyl-2-oxopentanoyl)hexahydro-2-pyridinecarboxylate, 14 (1R)-2,2-dimethyl-1-phenethyl-3-butenyl(2S)-1-(3,3-dimethyl-2-oxopentanoyl)hexahydro-2-pyridinecarboxylate, 15 (1R)-1,3-diphenylpropyl(2S)-1-(3,3-dimethyl-2-oxopentanoyl)hexahydro-2-pyridinecarboxylate, 16 (1R)-1-cyclohexyl-3-phenylpropyl(2S)-1-(3,3-dimethyl-2-oxopentanoyl)hexahydro-2-pyridinecarboxylate, 17 (1S)-1,3-diphenylpropyl(2S)-1(3,3-dimethyl-2-oxopentanoyl)hexahydro-2-pyridinecarboxylate, 18 (1S)-1-cyclohexyl-3-phenylpropyl(2S)-1-(3,3-dimethyl-2-oxopentanoyl)hexahydro-2-pyridinecarboxylate, 19 (22aS)-15,15-dimethylperhydropyrido[2,1-c][1,9,4] dioxazacyclononadecine-1,12,16,17-tetraone, 20 (24aS)-17,17-dimethylperhydropyrido[2,1-c][1,9,4] dioxazacyclohenicosine-1,14,18,19-tetraone, 22 (3R,4R,23aS)-8-allyl-4,10-dimethyl-3-[2-(3-pyridyl) ethyl]-1,3,4,5,6,7,8,11,12,15,16,17,18,20,21,22,23,23a-octadecahydro-14H-pyrido[2,1-c][1,10,4] dioxazacycloicosine-1,7,14,17,18-pentaone, 23 (3R,4R,24aS)-8-allyl-4,10-dimethyl-3-[2-(3-pyridyl) ethyl]-1,3,4,5,6,7,8,11,12,14,15,16,17,18,19,21,22,23,24,24a-icosahydropyrido[2,1-c][1,11,4] dioxazacyclohenicosine-1,7,14,18,19-pentaone, 24 (3R,4R,25aS)-8-allyl-4,10-dimethyl-3-[2-(3-pyridyl) ethyl]-1,3,4,5,6,7,8,11,12,15,16,17,18,19,20,22,23,24,25,25a-icosahydro-14H-pyrido[2,1-c][1,12,4] dioxazacyclodocosine-1,7,14,19,20-pentaone, 32 (1R)-1-(3-benzoylphenyl)-3-phenylpropyl(1R)-2-(3,3-dimethyl-2-oxopentanoyl)cyclohexane-1-carboxylate, 33 (1R)-1-[3-(diallylcarbamoyl)phenyl]-3-phenylpropyl (1R)-2-(3,3-dimethyl-2-oxopentanoyl)cyclohexane-1-carboxylate, 35 ethyl 1-(2-oxo-3-phenylpropanoyl)-2-piperidinecarboxylate, 36 ethyl 1-pyruvoyl-2-piperidinecarboxylate, 37 ethyl 1-(2-oxobutanoyl)-2-piperidinecarboxylate, 38 ethyl 1-(3-methyl-2-oxobutanoyl)-2-piperidinecarboxylate, 39 ethyl 1-(4-methyl-2-oxopentanoyl)-2-piperidinecarboxylate, 40 ethyl 1-(3,3-dimethyl-2-oxobutanoyl)-2-piperidinecarboxylate, 41 ethyl 1-(3,3-dimethyl-2-oxopentanoyl)-2-piperidinecarboxylate, 42 4-[2-(ethyloxycarbonyl)piperidinol-2,2-dimethyl-3,4-dioxobutyl acetate, 43 ethyl 1-[2-(2-hydroxytetrahydro-2H-2-pyranyl)-2-oxoacetyl]-2-piperidinecarboxylate, 44 ethyl 1-[2-(2-methoxytetrahydro-2H-2-pyranyl)-2-oxoacetyl]-2-piperidinecarboxylate, 45 ethyl 1-[2-(1-hydroxycyclohexyl)-2-oxoacetyl]-2-piperidinecarboxylate, 46 ethyl 1-[2-(1-methoxycyclohexyl)-2-oxoeretyl]-2-piperidinecarboxylate, 47 ethyl 1-(2-cyclohexyl-2-oxoacetyl)-2-pipiperidinecarboxylate, 48 ethyl 1-(2-oxo-2-piperidinoacetyl)-2-piperidinecarboxylate, 49 ethyl 1-[2-(3,4-dihydro-2H-6-pyranyl)-2-oxoacetyl]-2-piperidinecarboxylate, 50 ethyl 1-(2-oxo-2-phenylacetyl)-2-piperidinecarboxylate, 51 ethyl1-(4-methyl-2-oxo-1-thioxopentyl)-2-piperidinecarboxylate, 52 3-phenylpropyl1-(2-hydroxy-3,3-dimethylpentanoyl)-2-piperidinecarboxylate, 53 (1R)-1-phenyl-3-(3,4,5-trimethoxyphenyl)propyl1-(3,3-dimethylbutanoyl)-2-piperidinecarboxylate, 54 (1R)-1,3-diphenylpropyl1-(benzylsulfonyl)-2-piperidinecarboxylate, 55 3-(3,4,5-trimethoxyphenyl)propyl1-(benzylsulfonyl)-2-piperidinecarboxylate, 56 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylic acid, 57 methyl1-(2-[(2R,3R,6S)-6-[(2S,3E,5E,7E,9S,11R)-2,13,-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, 58 isopropyl1-(2-[(2R,3R,6S)-6-[(2S,3E,5E,7E,9S,11R)-2,13-dimethoxy-3,9,11-trimethyl-12-oxo-3,5,7-tridecatrienyl] -2-hydroxy-3-methyltetrahydro-2H-2-pyranyl)-2-oxoacetyl)-2-piperidinecarboxylate, 59 benzyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, 60 1-phenylethyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, 61 (Z)-3-phenyl-2-propenyl1-(2-(2,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, 62 3-(3,4-dimethoxyphenyl)-propyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, 63 N2-benzyl-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, and 64 N2-(3-phenylpropyl)-1-(2-(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.

8. The method of claim 1 wherein the non-immunosuppressive pipecolic acid derivative is administered orally.

9. The method of claim 1, wherein the non-immunosuppressive pipecolic acid derivative is selected from the group consisting of:

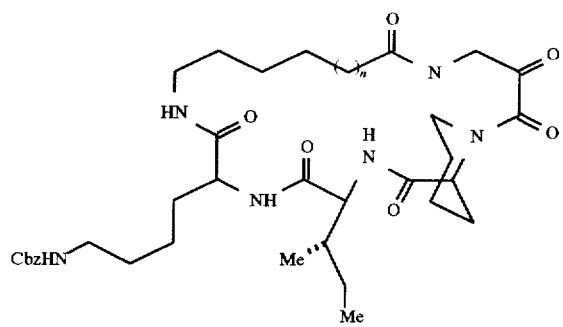

Compounds 3–5 wherein n is 1, 2, or 3;

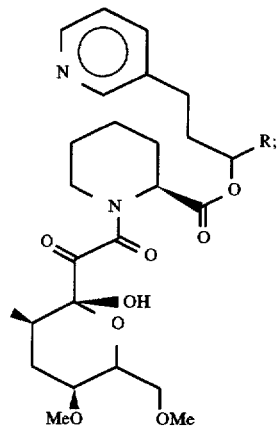

Compound 10

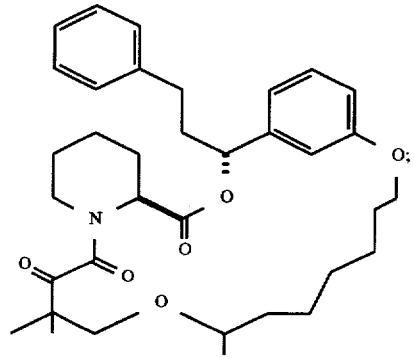

Compound 21

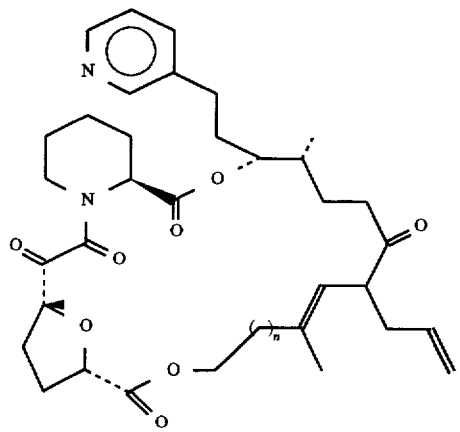

wherein n is 1, 2, or 3.
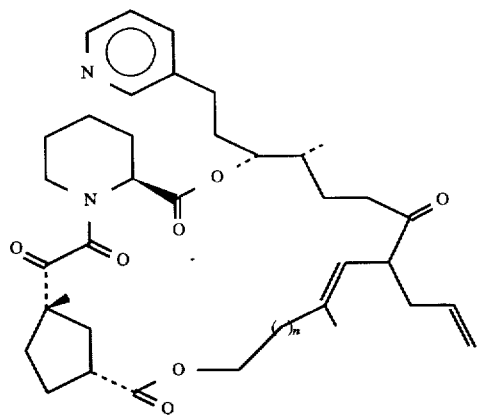
wherein n is 1, 2, or 3.
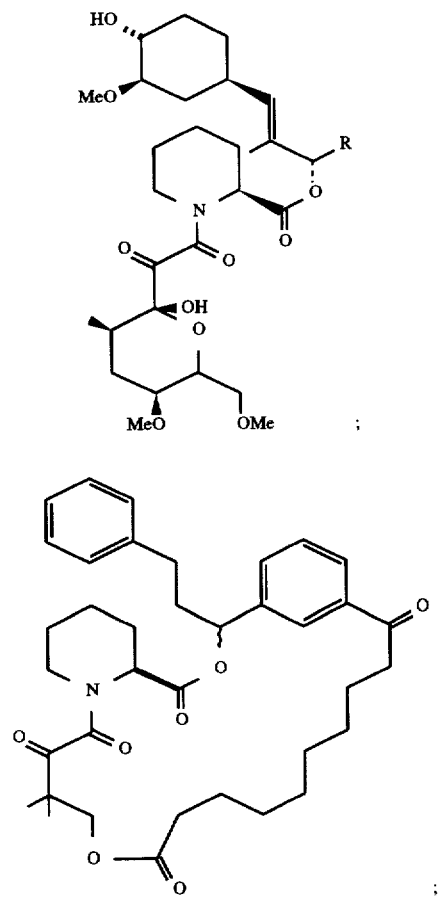
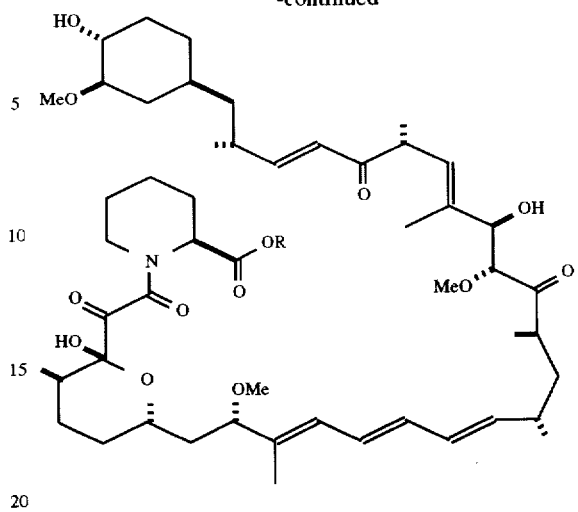
wherein R is Methyl (Me) or benzyl (Bn).
Compound 31
Compound 34
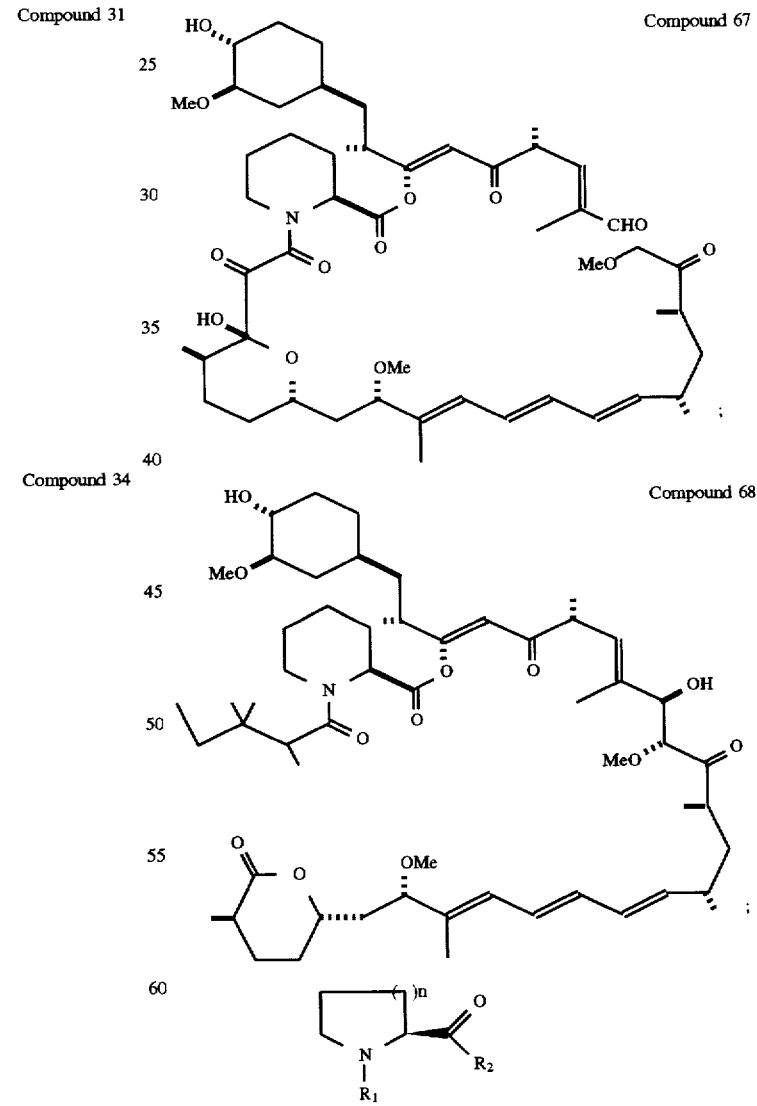
Compound 67
Compound 68 wherein
n=2
R₁=

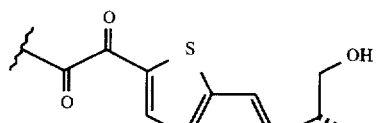

or

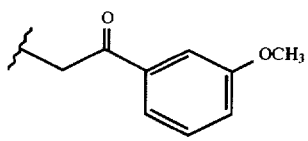

and
R₂=Phe-o-tert-butyl,

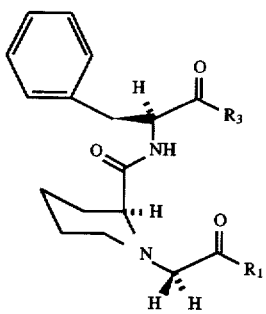

wherein
R₁=m-OCH₃Ph, R₃=Val-o-tert-butyl; Compound 71
R₁=m-OCH₃Ph, R₃=Leu-o-tert-butyl; Compound 72
R₁=m-OCH₃Ph, R₃=Ileu-o-tert-butyl; Compound 73
R₁=m-OCH₃Ph, R₃=hexahydro-Phe-o-tert-butyl; Cmpd 74
R₁=m-OCH₃Ph, R₃=allylalanine-o-tert-butyl; Cmpd 75
R₁=B-naphthyl, R₃=Val-o-tert-butyl; Compound 76

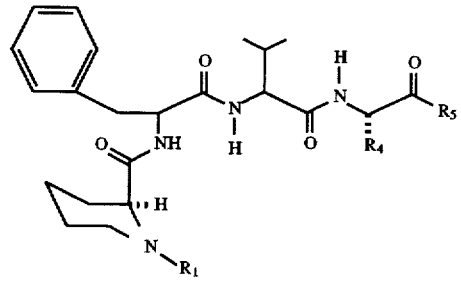

wherein
R₁=CH₂(CO)-m-OCH₃Ph (Compound 77)
R₄=CH₂Ph
R₅=OCH₃
or
R₁=CH₂(CO)-B-naphthyl (Compound 78)
R₄=CH₂Ph
R₅=OCH₃

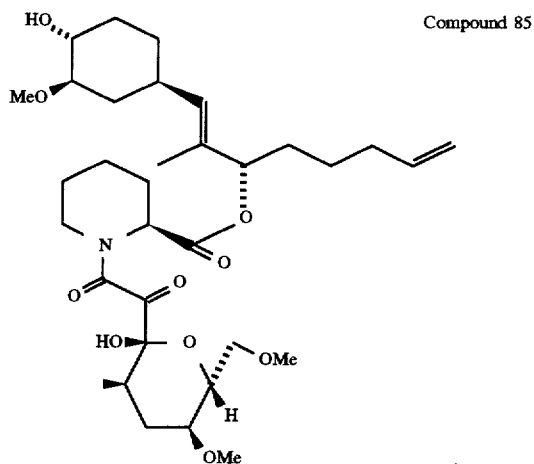

wherein
R₁=m-OCH₃Ph (Compound 79)
X=trans-CH=CH
R₄=H
Y=OC(o)Ph
R₁=m-OCH₃Ph (Compound 80)
X=trans-CH=CH
R₄=H
Y=OC(o)CF₃
R₁=m-OCH₃Ph (Compound 81)
X=trans-CH=CHI
R₄=—
Y=—
R₁=m-OCH₃Ph (Compound 82)
X=trans-CH=CH
R₄=H
Y=OCH₂CH=CH₂
R₁=m-OCH₃Ph (Compound 83)
X=C=O
R₄=H
Y=Ph Compound 85

;

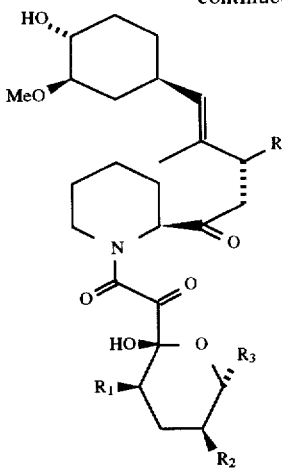

wherein $R_1$=H, $R_2$=OMe, and $R_3$=CH$_2$OMe (Compound 86);
$R_1$=H, $R_2$=H, and $R_3$=H (Compound 87); and
$R_1$=Me, $R_2$=H, and $R_3$=H (Compound 88).

10. A method of treating a neurological disorder in an animal, comprising:

administering to an animal an effective amount of a non-immunosuppressive pipecolic acid derivative having an affinity for FKBP-type immunophilins in combination with an effective amount of a neurotrophic factor selected from the group consisting of neurotrophic growth factor, brain derived growth factor, glial derived growth factor, cilial neurotrophic factor, and neurotropin-3, to stimulate growth of damaged peripheral nerves or to promote neuronal regeneration, wherein the FKBP-type immunophilin exhibits rotamase activity and the non-immunosuppressive pipecolic acid derivative inhibits said rotamase activity of the immunophilin.

11. The method of claim 10, wherein the neurological disorder is selected from the group consisting of peripheral neuropathies cause by physical injury or disease state, physical damage to the brain, physical damage to the spinal cord, stroke associated with brain damage, and neurological disorders relating to neurodegeneration.

12. The method of claim 11, wherein the neurological disorder is selected from the group consisting of Alzheimer's Disease, Parkinson's Disease, and amyotrophic lateral sclerosis.

13. The method of claim 10, wherein the non-immunosuppressive pipecolic acid derivative is Way-124, 666.

14. The method of claim 10, wherein the non-immunosuppressive pipecolic acid derivative is Rap-Pa.

15. The method of claim 10, wherein the non-immunosuppressive pipecolic acid derivative is SLB-506.

16. The method of claim 10, wherein the non-immunosuppressive pipecolic acid derivative is selected from the up consisting of 6 4-(4-methoxyphenyl)butyl(2S)-1-[2-(3,4,5-trimethoxyphenyl)acetyl]hexahydro-2-pyridinecarboxylate, 7 4-(4-methoxyphenyl)butyl(2S)-1-[2-(3,4,5-trimethoxyhenyl)acryloyl]hexahydro-2-pyridinecarboxylate, 8 4-(4-methoxyphenyl)butyl(2S)-1-[2-(3,4,5-trimethoxyphenyl)propanoyl]hexahydro-2-pyridinecarboxylate, 9 4-(4-methoxyphenyl)butyl(2S)-1-[2-oxo-2-(3,4,5-trimethoxyphenyl)acetyl]hexahydro-2-pyridinecarboxylate, 11 3-cyclohexylpropyl(2S)-1-(3,3-dimethyl-2-oxopentanoyl)hexahydro-2-pyridinecarboxylate, 12 3-phenylpropyl(2S)-1-(3,3-dimethyl-2-oxopentanoyl) hexahydro-2-pyridinecarboxylate, 13 3-(3,4,5-trimethoxyphenyl)propyl(2S)-1-(3,3-dimethyl-2-oxopentanoyl)hexahydro-2-pyridinecarboxylate, 14 (1R)-2,2-dimethyl-1-phenethyl-3-butenyl(2S)-1-(3,3-dimethyl-2-oxopentanoyl)hexahydro-2-pyridinecarboxylate, 15 (1R)-1,3-diphenylpropyl(2S)-1-(3,3-dimethyl-2-oxopentanoyl)hexahydro-2-pyridinecarboxylate, 16 (1R)-1-cyclohexyl-3-phenylpropyl(2S)-1-(3,3-dimethyl-2-pentanoyl)hexahydro-2-pyridinecarboxylate, 17 (1S)-1,3-diphenylpropyl(2S)-1-(3,3-dimethyl-2-pentanoyl)hexahydro-2-pyridinecarboxylate, 18 (1S)-1-cyclohexyl-3-phenylpropyl(2S)-1-(3,3-dimethyl-2-oxopentanoyl)hexahydro-2-pyridinecarboxylate, 19 (22aS)-15,15-dimethylperhydropyrido[2,1-c][1,9,4]dioxazacyclononadecine-1,12,16,17-tetraone, 20 (24aS)-17,17-dimethylperhydropyrido[2,1-c][1,9,4]dioxazacyclohenicosine-1,14,18,19-tetraone, 22 (3R,4R,23aS)-8-allyl-4,10-dimethyl-3-[2-(3-pyridyl)ethyl]-1,3,4,5,6,7,8,11,12,15,16,17,18,20,21,22,23,23a-octadecahydro-14H-pyrido[2,1-c][1,10,4]dioxazacycloicosine-1,7,14,17,18-pentaone, 23 (3R,4R,24aS)-8-allyl-4,10-dimethyl-3-[2-(3-pyridyl)ethyl]-1,3,4,5,6,7,8,11,12,14,15,16,17,18,19,21,22,23,24,24a-icosahydropyrido[2,1-c][1,11,4]dioxazacyclohenicosine-1,7,14,18,19-pentaone, 24 (3R,4R,25aS)-8-allyl-4,10-dimethyl-3-[2-(3-pyridyl)ethyl]-1,3,4,5,6,7,8,11,12,15,16,17,18,19,20,22,23,24,25,25a-icosahydro-14H-pyrido[2,1-c][1,12,4]dioxazacyclodocosine-1,7,14,19,20-pentaone, 32 (1R)-1-(3-benzoylphenyl)-3-phenylpropyl(1R)-2-(3,3-dimethyl-2-oxopentanoyl)cyclohexane-1-carboxylate, 33 (1R)-1-[3-(diallylcarbamoyl)-phenyl]-3-phenylpropyl(1R)-2-(3,3-dimethyl-2-oxopentanoyl)cyclohexane-1-carboxylate, 35 ethyl1-(2-oxo-3-phenylpropanoyl)-2-piperidinecarboxylate, 36 ethyl1-pyruvoyl-2-piperidinecarboxylate, 37 ethyl1-(2-oxobutanoyl)-2-piperidinecarboxylate, 38 ethyl1-(3-methyl-2-oxobutanoyl)-2-piperidinecarboxylate, 39 ethyl1-(4-methyl-2-oxooentanoyl)-2-piperidinecarboxylate, 40 ethyl1-(3,3-dimethyl-2-oxobutanoyl)-2-piperidinecarboxylate, 41 ethyl1-(3,3-dimethyl-2-oxopentanoyl)-2-piperidinecarboxylate, 42 4-[2-(ethyloxycarbonyl)piperidino]-2,2-dimethyl-3,4-dioxobutyl acetate, 43 ethyl1-[2-(2-hydroxytetrahydro-2H-2-pyranyl)-2-oxoacetyl]-2-piperidinecarboxylate, 44 ethyl1-[2-(2-methoxytetrahydro-2H-2-pyranyl)-2-oxoacetyl]-2-piperidinecarboxylate, 45 ethyl1-[2-(1-hydroxycyclohexyl)-2-oxoacetyl]-2-piperidinecarboxylate, 46 ethyl1-[2-(1-methoxycyclohexyl)-2-oxoacetyl]-2-piperidinecarboxylate, 47 ethyl1-(2-cyclohexyl-2-oxoacetyl)-2-piperidinecarboxylate, 48 ethyl1-(2-oxo-2-piperidinoacetyl)-2-piperidinecarboxylate, 49 ethyl1-[2-(3,4-dihydro-2H-6-pyranyl)-2-oxoacetyl]-2-piperidinecarboxylate, 50 ethyl1-(2-oxo-2-phenylacetyl)-2-piperidinecarboxylate,
51 ethyl1-(4-methyl-2-oxo-1-thioxopentyl)-2-piperidinecarboxylate,
52 3-phenylpropyl1-(2-hydroxy-3,3-dimethylpentanoyl)-2-piperidinecarboxylate,
53 (1R)-1-phenyl-3-(3,4,5-trimethoxyphenyl)propyl1-(3,3-dimethylbutanoyl)-2-piperidinecarboxylate,
54 (1R)-1,3-diphenylpropyl1-(benzylsulfonyl)-2-piperidinecarboxylate,
55 3-(3,4,5-trimethoxyphenyl)propyl1-(benzylsulfonyl)-2-piperidinecarboxylate,
56 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylic acid,
57 methyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate,
58 isopropyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxyylate,
59 benzyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate,
60 1-phenylethyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate,
61 (Z)-3-phenyl-2-propenyl1-(2-2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate,
62 3-(3,4-dimethoxyphenyl)propyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate,
63 N2-benzyl-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, and
64 N2-(3-phenylpropyl)-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.

17. The method of claim 10 wherein the non-immunosuppressive pipecolic acid derivative is administered orally.

18. The method of claim 10, wherein the non-immunosuppressive pipecolic acid derivative is selected from the group consisting of:

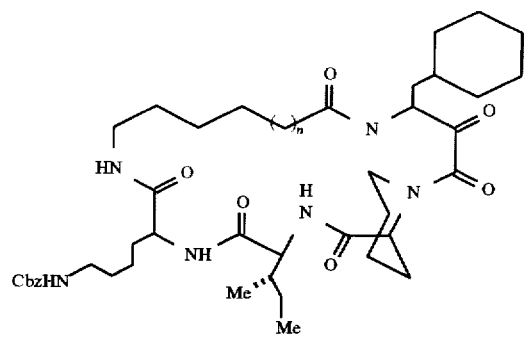

Compounds 3–5 wherein n is 1, 2, or 3;

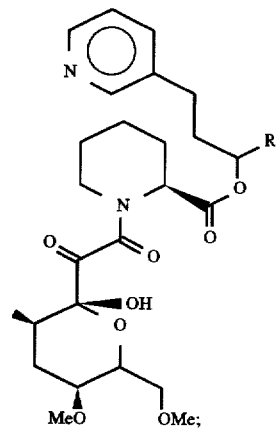

Compound 10

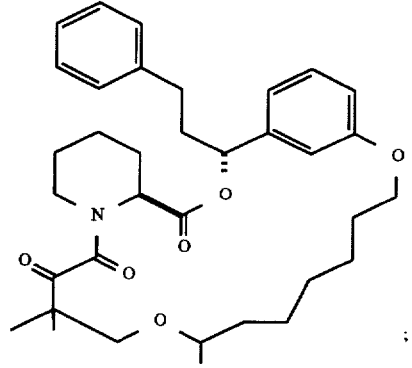

Compound 21

-continued
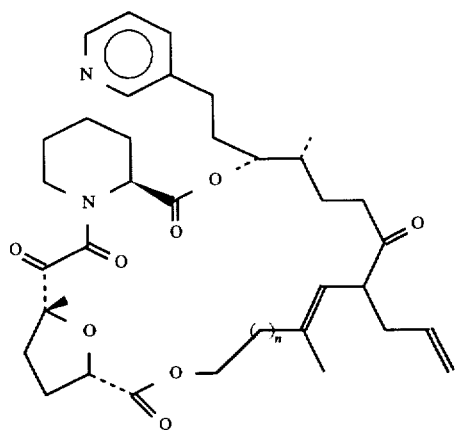
wherein n is 1, 2, or 3,
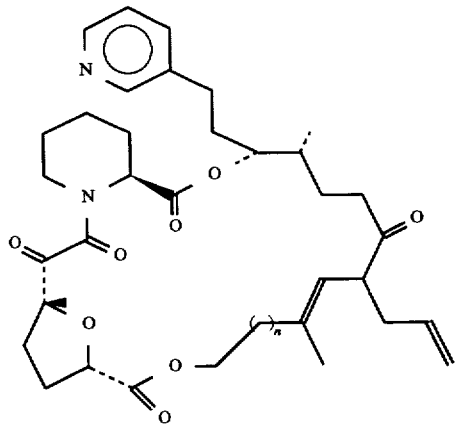
wherein n is 1, 2, or 3,
Compound 31
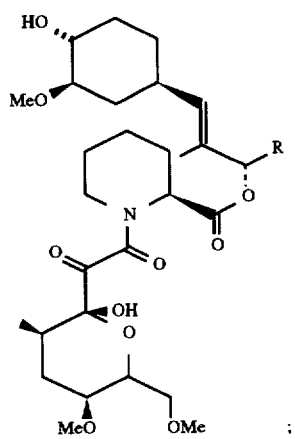
-continued
Compound 34
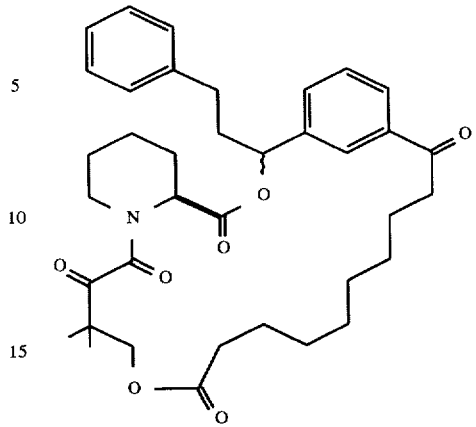
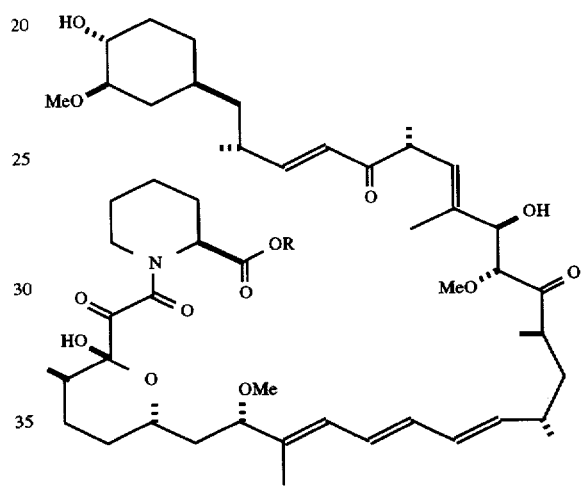
wherein R is Methyl (Me) or Benzyl (Bn),
Compound 67
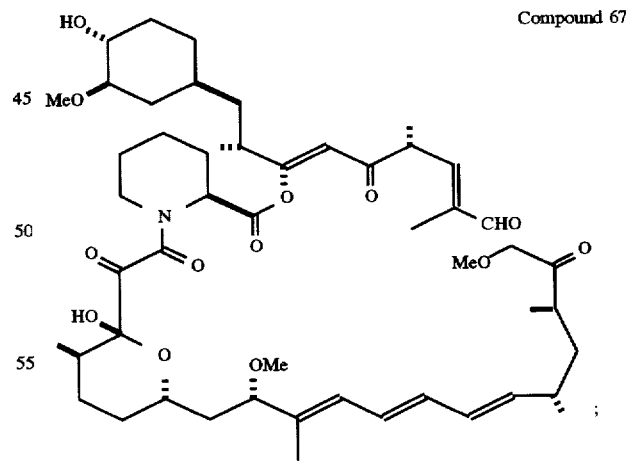

57

-continued

Compound 68

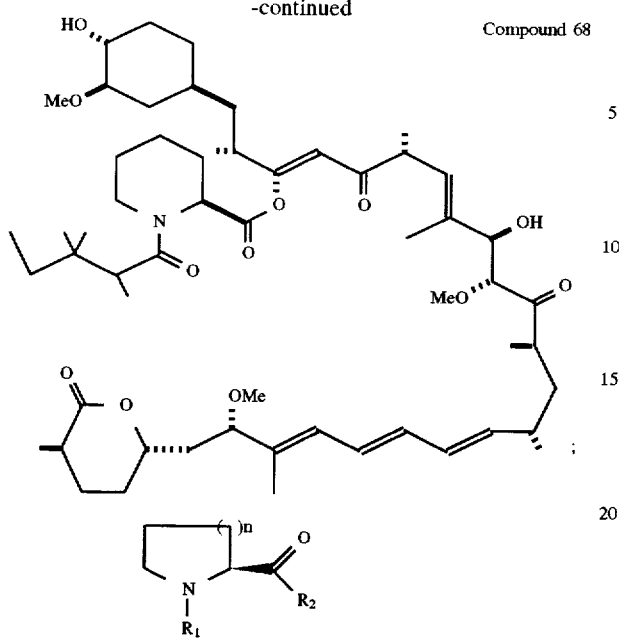

wherein
n=2
$R_1=$

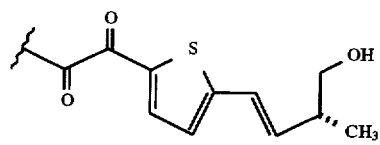

or

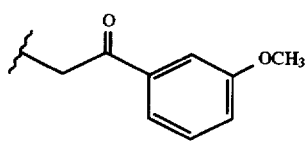

and
$R_2=$Phe-o-tert-butyl.

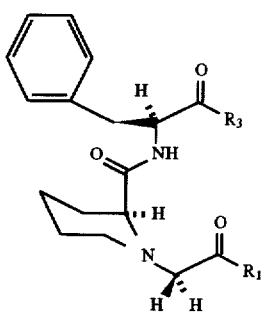

wherein
$R_1=$m-OCH$_3$Ph, $R_3=$Val-o-tert-butyl; Compound 71

58

$R_1=$m-OCH$_3$Ph, $R_3=$Leu-o-tert-butyl; Compound 72
$R_1=$m-OCH$_3$Ph, $R_3=$Ileu-o-tert-butyl; Compound 73
$R_1=$m-OCH$_3$Ph, $R_3=$hexahydro-Phe-o-tert-butyl; Cmpd 74
$R_1=$m-OCH$_3$Ph, $R_3=$allylalanine-o-tert-butyl; Cmpd 75
$R_1=$B-naphthyl, $R_3=$Val-o-tert-butyl; Compound 76

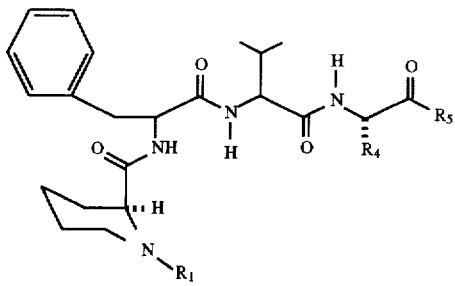

wherein
$R_1=$CH$_2$(CO)-m-OCH$_3$Ph (Compound 77)
$R_4=$CH$_2$Ph
$R_5=$OCH$_3$
or
$R_1=$CH$_2$(CO)-B-naphthyl (Compound 78)
$R_4=$CH$_2$Ph
$R_5=$OCH$_3$

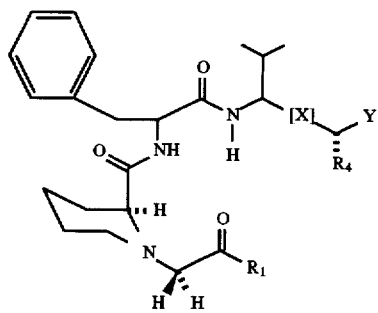

wherein
$R_1=$m-OCH$_3$Ph (Compound 79)
X=trans-CH=CH
$R_4=$H
Y=OC(o)Ph
$R_1=$m-OCH$_3$Ph (Compound 80)
X=trans-CH=CH
$R_4=$H
Y=OC(o)CF$_3$
$R_1=$m-OCH$_3$Ph (Compound 81)
X=trans-CH=CHI
$R_4=$—
Y=—
$R_1=$m-OCH$_3$Ph (Compound 82)
X=trans-CH=CH
$R_4=$H
Y=OCH$_2$CH=CH$_2$
$R_1=$m-OCH$_3$Ph (Compound 83)
X=C=O
$R_4=$H
Y=Ph

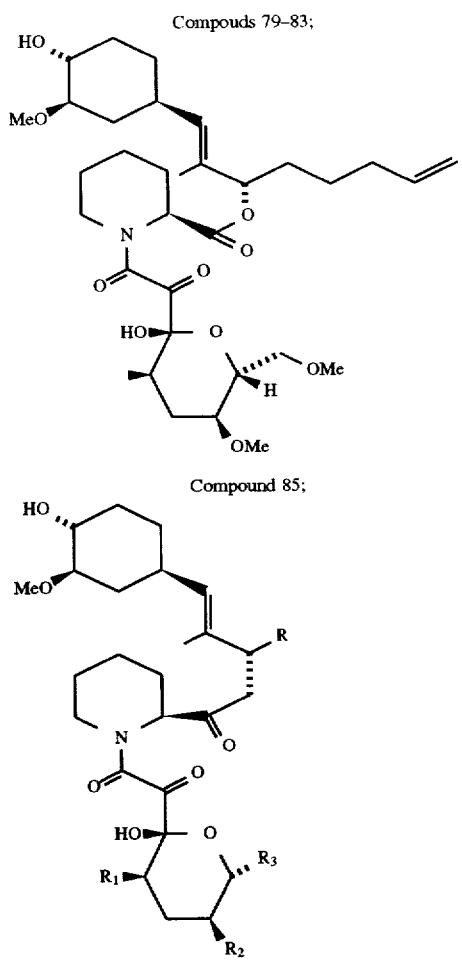

Compouds 79-83;

Compound 85;

wherein
$R_1$=H, $R_2$=OMe, and $R_3$=CH$_2$OME (Compound 86);
$R_1$=H, $R_2$=H, and $R_3$=H (Compound 87); and
$R_1$=Me, $R_2$=H, and $R_3$=H (Compound 88).

19. A method of stimulating growth of damaged peripheral nerves, comprising;
administering to damaged peripheral nerves an effective amount of a non-immunosuppressive pipecolic acid derivative compound having an affinity for FKBP-type immunophilins to stimulate or promote growth of the damaged peripheral nerves, wherein the FKBP-type immunophilins exhibit rotamase activity and the non-immunosuppressive pipecolic acid derivative inhibits said rotamase activity of the immunophilin.

20. The method of claim 19, further comprising administering a neurotrophic factor to stimulate or promote growth of the damaged peripheral nerves selected from the group consisting of neurotrophic growth factor, brain derived growths factor, glial derived growth factor, cilial neurotrophic factor, and neurotropin-3.

21. The method of claim 19, wherein the non-immunosuppressive pipecolic acid derivative is Way-124, 666.

22. The method of claim 19, wherein the non-immunosuppressive pipecolic acid derivative is Rap-Pa.

23. The method of claim 19, wherein the non-immunosuppressive pipecolic acid derivative is SLB-506.

24. The method of claim 19, wherein the non-immunosuppressive pipecolic acid derivative is selected from the group consisting of 6  4-(4-methoxyphenyl)butyl(2S)-1-|2-(3,4,5-trimethoxyphenyl)acetyl|hexahydro-2-pyridinecarboxylate, 7  4-(4-methoxyphenyl)butyl(2S)-1-|2-(3,4,5-trimethoxyphenyl)acryloyl|hexahydro-2-pyridinecarboxylate, 8  4-(4-methoxyphenyl)butyl(2S)-1-|2-(3,4,5-trimethoxyphenyl)propanoyl|hexahydro-2-pyridinecarboxylate.

9  4-(4-methoxyphenyl)butyl(2S)-1-|2-oxo-2-(3,4,5-trimethoxyphenyl)acetyl|hexahydro-2-pyridinecarboxylate, 11  3-cyclohexylpropyl(2S)-1-(3,3-dimethyl-2-oxopentanoyl)hexahydro-2-pyridinecarboxylate, 12  3-phenylpropyl(2S)-1-(3,3-dimethyl-2-oxopentanoyl)hexahydro-2-pyridinecarboxylate, 13  3-(3,4,5-trimethoxyphenyl)propyl(2S)-1-(3,3-dimethyl-2-oxopentanoyl)hexahydro-2-pyridinecarboxylate, 14  (1R)-2,2-dimethyl-1-phenethyl-3-butenyl(2S)-1-(3,3-dimethyl-2-oxopentanoyl)hexahydro-2-pyridinecarboxylate, 15  (1R)-1,3-diphenylpropyl(2S)-1-(3,3-dimethyl-2-oxopentanoyl)hexahydro-2-pyridinecarboxylate, 16  (1R)-1-cyclohexyl-3-phenylpropyl(2S)-1-(3,3-dimethyl-2-oxopentanoyl)hexahydro-2-pyridinecarboxylate, 17  (1S)-1,3-diphenylpropyl(2S)-1-(3,3-dimethyl-2-oxopentanoyl)hexahydro-2-pyridinecarboxylate, 18  (1S)-1-cyclohexyl-3-phenylpropyl(2S)-1-(3,3-dimethyl-2-oxopentanoyl)hexahydro-2-pyridinecarboxylate, 19  (22aS)-15,15-dimethylperhydropyrido[2,1-c||1,9,4] dioxazacyclononadecine-1,12,16,17-tetraone, 20  (24aS)-17,17-dimethylperhydropyrido[2,1-c||1,9,4] dioxazacyclohenicosine-1,14,18,19-tetraone, 22  (3R,4R,23aS)-8-allyl-4,10-dimethyl-3-|2-(3-pyridyl)ethyl|-1,3,4,5,6,7,8,11,12,15,16,17,18,20,21,22,23,23a-octadecahydro-14H-pyrido|2,1-c||1,10,4| dioxazacycloicosine-1,7,14,17,18-pentaone, 23  (3R,4R,24aS)-8-allyl-4,10-dimethyl-3-[2-(3-pyridyl)ethyl|-1,3,4,5,6,7,8,11,12,14,15,16,17,18,19,21,22,23,24,24a-icosahydropyrido]2,1-c]|1,11,4] dioxazacyclohenicosine-1,7,14,18,19-pentaone, 24  (3R,4R,25aS)-8-allyl-4,10-dimethyl-3-|2-(3-pyridyl)ethyl|-1,3,4,5,6,7,8,11,12,15,16,17,18,19,20,22,23,24,25, 25a-icosahydro-14H-pyrido[2,1-c][1,12,4] dioxazacyclodocosine-1,7,14,19,20-pentaone, 32  (1R)-1-(3-benzoylphenyl)-3-phenylpropyl(1R)-2-(3,3-dimethyl-2-oxopentanoyyl)cyclohexane-1-carboxylate, 33  (1R)-1-[3-(diallylcarbamoyl)phenyl]-3-phenylpropyl(1R)-2-(3,3-dimethyl-2-oxopentanoyl)cyclohexane-1-carboxylate, 35  ethyl1-(2-oxo-3-phenylpropanoyl)-2-piperidinecarboxylate.

36  ethyl1-pyruvoyl-2-piperidinecarboxylate.

37  ethyl1-(2-oxobutanoyl)-2-piperidinecarboxylate.

38  ethyl1-(3-methyl-2-oxobutanoyl)-2-piperidinecarboxylate, 39  ethyl1-(4-methyl-2-oxopentanoyl)-2-piperidinecarboxylate, 40  ethyl1-(3,3-dimethyl-2-oxobutanoyl)-2-piperidinecarboxylate, 41  ethyl1-(3,3-dimethyl-2-oxopentanoyl)-2-piperidinecarboxylate, 42  4-[2-(ethyloxycarbonyl)piperidino]-2,2-dimethyl-3,4-dioxobutyl acetate, 43  ethyl1-|2-(2-hydroxytetrahydro-2H-2-pyranyl)-2-oxoacetyl|-2-piperidinecarboxylate.

44  ethyl1-[2-(2-methoxytetrahydro-2H-2-pyranyl)-2-oxoacetyl|-2-piperidinecarboxylate, 45 ethyl1-[2-(1-hydroxycyclohexyl)-2-oxoacetyl]-2-piperidinecarboxylate.
46 ethyl1-[2-(1-methoxycyclohexyl)-2-oxoacetyl]-2-piperidinecarboxylate.
47 ethyl1-(2-cyclohexyl-2-oxoacetyl)-2-piperidinecarboxylate.
48 ethyl1-(2-oxo-2-piperidinoacetyl)-2-piperidinecarboxylate.
49 ethyl1-[2-(3,4-dihydro-2H-6-pyranyl)-2-oxoacetyl)-2-piperidinecarboxylate.
50 ethyl1-(2-oxo-2-phenylacetyl)-2-piperidinecarboxylate.
51 ethyl1-(4-methyl-2-oxo-1-thioxopentyl)-2-piperidinecarboxylate.
52 3-phenylpropyl1-(2-hydroxy-3,3-dimethylpentanoyl)-2-piperidinecarboxylate.
53 (1R)-1-phenyl-3-(3,4,5-trimethoxyphenyl)propyl1-(3,3-dimethylbutanoyl)-2-piperidinecarboxylate.
54 (1R)-1,3-diphenylpropyl1-(benzylsulfonyl)-2-piperidinecarboxylate.
55 3-(3,4,5-trimethoxyphenyl)propyl1-(benzylsulfonyl)-2-piperidinecarboxylate.
56 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylic acid.
57 methyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
58 isopropyl1-(2-[(2R,3R,6S)-6-[(2S,3E,5E,7E,9S,11R)-2,13-dimethoxy-3,9,11-trimethyl-12-oxo-3,5,7-tridecatrienyl]- 2-hydroxy-3-methyltetrahydro-2H-2-pyranyl)-2-oxoacetyl)-2-piperidinecarboxylate.
59 benzyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
60 1-phenylethyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
61 (Z)-3-phenyl-2-propenyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
62 3-(3,4-dimethoxyphenyl)propyl1-(2-[(2R,3R,6S)-6-[(2S,3E,5E,7E,9S,11R)-2,13-dimethoxy-3,9,11-trimethyl-12-oxo-3,5,7-tridecatrienyl)-2-hydroxy-3-methyltetrahydro-2H-2-pyranyl)-2-oxoacetyl)-2-piperidinecarboxylate.
63 N2-benzyl-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, and
64 N2-(3-phenylpropyl)-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.

25. The method of claim 19 wherein the non-immunosuppressive pipecolic acid derivative is administered orally.

26. The method of claim 19, wherein the non-immunosuppressive pipecolic acid derivative is selected from the group consisting of:

Compound 3-5

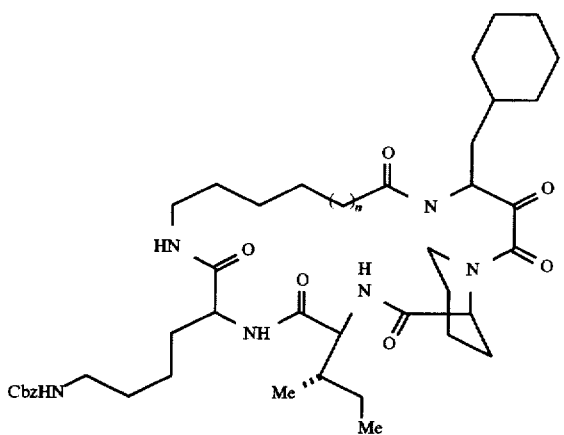

wherein n is 1, 2, or 3;

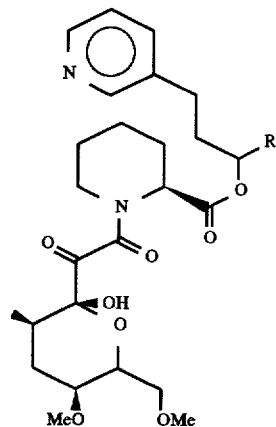

Compound 10;

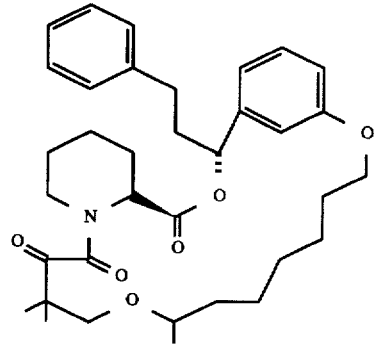

Compound 21;
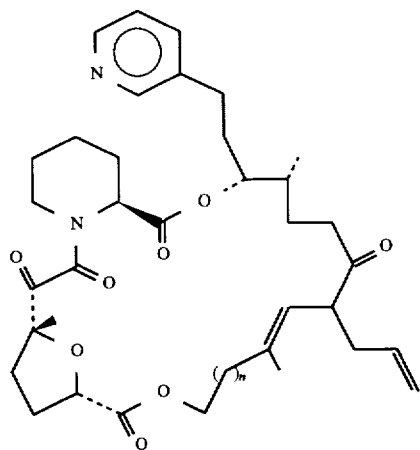
wherein n is 1, 2, or 3.
Compounds 25–27;
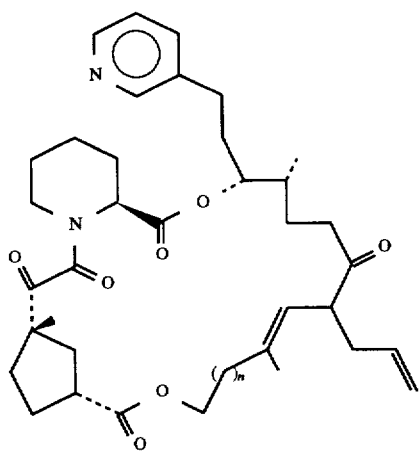
wherein n is 1, 2, or 3.
Compounds 28–30;
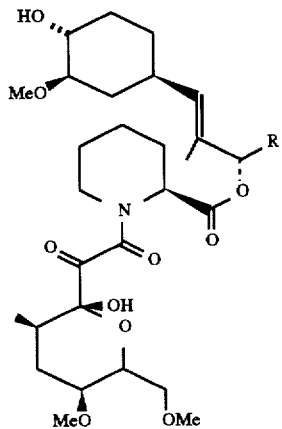
Compounds 28–30;
Compound 31;
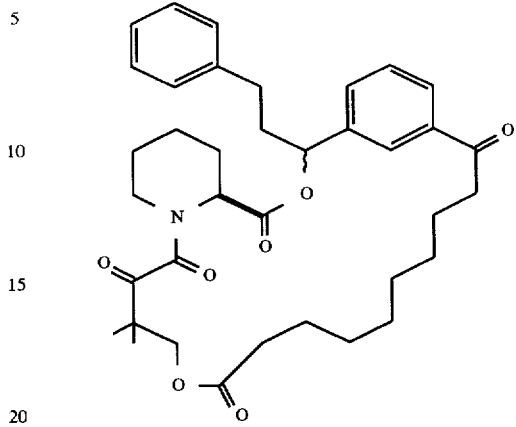
Compound 34;
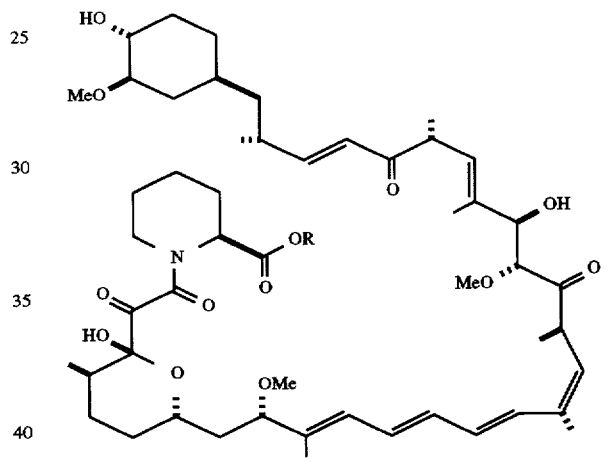
wherein R is Methyl (Me) or Benzyl (Bn).
Compounds 65 and 66;
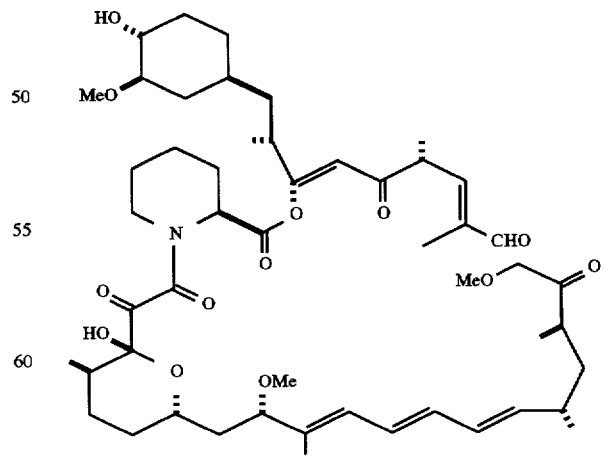

65

-continued
Compound 67;

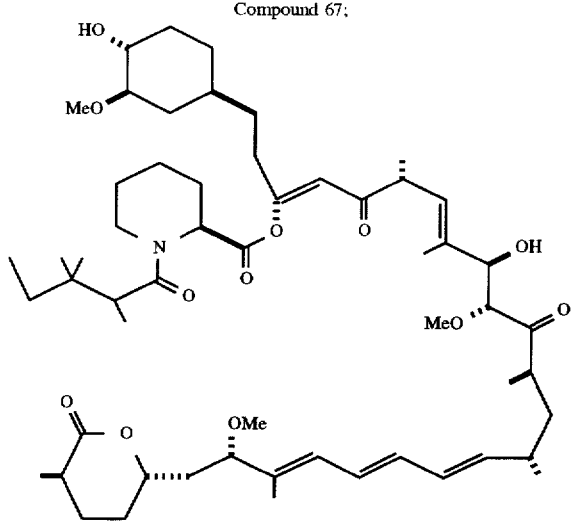

Compound 68;

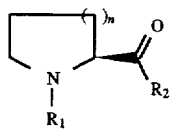

wherein
n=2
R$_1$=

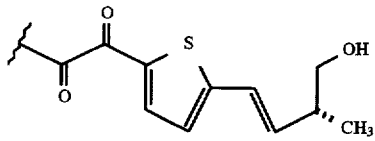

or

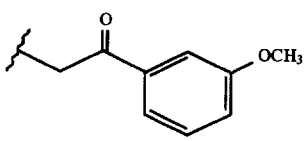

and
R$_2$=Phe-o-tert-butyl,

Compounds 69 and 70;

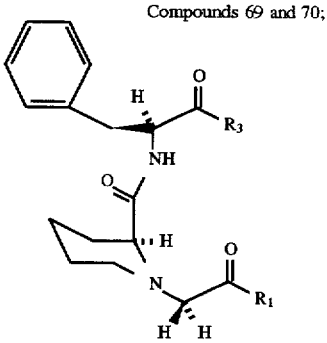

wherein
R$_1$=m-OCH$_3$Ph, R$_3$=Val-o-tert-butyl; Compound 71
R$_1$=m-OCH$_3$Ph, R$_3$=Leu-o-tert-butyl; Compound 72

66

R$_1$=m-OCH$_3$Ph, R$_3$=Ileu-o-tert-butyl; Compound 73
R$_1$=m-OCH$_3$Ph, R$_3$=hexahydro-Phe-o-tert-butyl; Cmpd 74
R$_1$=m-OCH$_3$Ph, R$_3$=allylalanine-o-tert-butyl; Cmpd 75
R$_1$=B-naphthyl, R$_3$=Val-o-tert-butyl; Compound 76

Compounds 71-76;

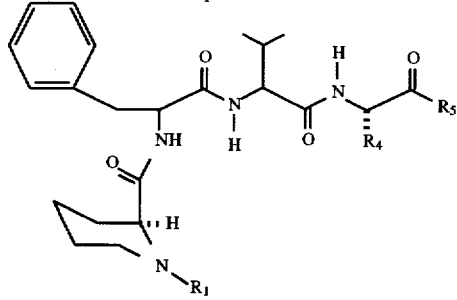

wherein
R$_1$=CH$_2$(CO)-m-OCH$_3$Ph (Compound 77)
R$_4$=CH$_2$Ph
R$_5$=OCH$_3$
or
R$_1$=CH$_2$(CO)-B-naphthyl (Compound 78)
R$_4$=CH$_2$Ph
R$_5$=OCH$_3$ Compounds 77 and 78;

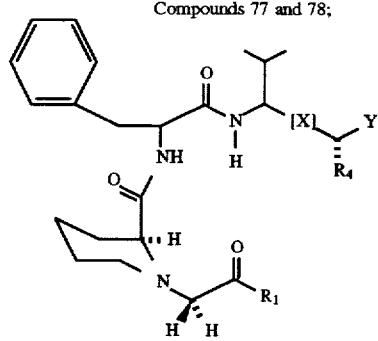

wherein
R$_1$=m-OCH$_3$Ph (Compound 79)
X=trans-CH=CH
R$_4$=H
Y=OC(o)Ph
R$_1$=m-OCH$_3$Ph (Compound 80)
X=trans-CH=CH
R$_4$=H
Y=OC(o)CF$_3$
R$_1$=m-OCH$_3$Ph (Compound 81)
X=trans-CH=CHI
R$_4$=—
Y=—
R$_1$=m-OCH$_3$Ph (Compound 82)
X=trans-CH=CH
R$_4$=H
Y=OCH$_2$CH=CH$_2$
R$_1$=m-OCH$_3$Ph (Compound 83)
X=C=O
R$_4$=H Y=Ph

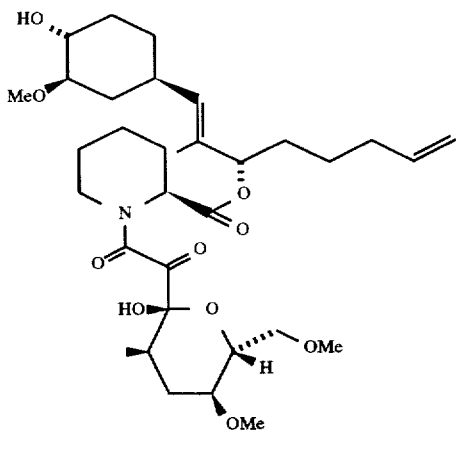

Compound 85;

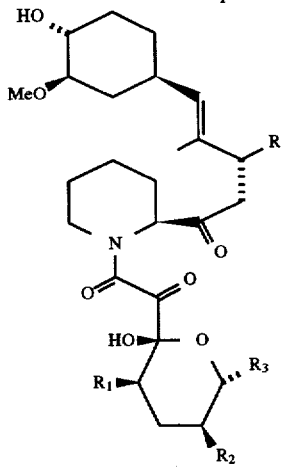

wherein
$R_1$=H, $R_2$=OMe, and $R_3$=CH$_2$OMe (Compound 86);
$R_1$=H, $R_2$=H, and $R_3$=H (Compound 87); and
$R_1$=Me, $R_2$=H, and $R_3$=H (Compound 88).

27. A method for promoting neuronal regeneration and growth in animals, comprising:
administering to an animal an effective amount of a non-immunosuppressive pipecolic acid derivative compound having an affinity for FKBP-type immunophilins to promote neuronal regeneration, wherein the FKBP-type immunophilins exhibit rotamase activity and the non-immunosuppressive pipecolic acid derivative inhibits said rotamase activity of the immunophilin.

28. The method of claim 27, further comprising administering an effective amount of a neurotrophic factor to promote neuronal regeneration selected from the group consisting of neurotrophic growth factor, brain derived growth factor, glial derived growth factor, and neurotropin-3.

29. The method of claim 27, wherein the non-immunosuppressive pipecolic acid derivative is Way-124,666.

30. The method of claim 27, wherein the non-immunosuppressive pipecolic acid derivative is Rap-Pa.

31. The method of claim 27, wherein the non-immunosuppressive pipecolic acid derivative is SLB-506.

32. The method of claim 27, wherein the non-immunosuppressive pipecolic acid derivative is selected from the group consisting of 6  4-(4-methoxyphenyl)butyl(2S)-1-[2-(3,4,5-trimethoxyphenyl)acetyl]hexahydro-2-pyridinecarboxylate.

7  4-(4-methoxpyhenyl)butyl(2S)-1-[2-(3,4,5-trimethoxyphenyl)acryloyl]hexahydro-2-pyridinecarboxylate.

8  4-(4-methoxyphenyl)butyl(2S)-1-[2-(3,4,5-trimethoxyphenyl)-propanoyl]hexahydro-2-pyridinecarboxylate.

9  4-(4-methoxyphenyl)butyl(2S)-1-[2-oxo-2-(3,4,5-trimethoxyphenyl)acetyl]hexahydro-2-pyridinecarboxylate.

11  3-cyclohexylpropyl(2S)-1-(3,3-dimethyl-2-oxopentanoyl)hexahydro-2-pyridinecarboxylate.

12  3-phenylpropyl(2S)-1-(3,3-dimethyl-2-oxonentanoyl)hexahydro-2-pyridinecarboxylate.

13  3-(3,4,5-trimethoxyphenyl)propyl(2S)-1-(3,3-dimethyl-2-oxopentanoyl)hexahydro-2-pyridinecarboxylate.

14  (1R)-2,2-dimethyl-1-phenethyl-3-butenyl(2S)-1-(3,3-dimethyl-2-oxopentanoyl)hexahydro-2-pyridinecarboxylate.

15  (1R)-1,3-diphenylpropyl(2S)-1-(3,3-dimethyl-2-pentanoyl)hexahydro-2-pyridinecarboxylate.

16  (1R)-1-cyclohexyl-3-phenylpropyl(2S)-1-(3,3-dimethyl-2-oxopentanoyl)hexahydro-2-pyridinecarboxylate.

17  (1S)-1,3-diphenylpropyl(2S)-1-(3,3-dimethyl-2-oxopentanoyl)hexahydro-2-pyridinecarboxylate.

18  (1S)-1-cyclohexyl-3-phenylpropyl(2S)-1-(3,3-dimethyl-2-oxopentanoyl)hexahydro-2-pyridinecarboxylate.

19  (22aS)-15,15-dimethylperhydropyrido[2,1-c][1,9,4] dioxazacyclononadecine-1,12,16,17-tetraone.

20  (24aS)-17,17-dimethylperhydropyrido[2,1-c][1,9,4] dioxazacyclohenicosine-1,14,18,19-tetraone.

22  (3R,4R,23aS)-8-allyl-4,10-dimethyl-3-[2-(3-pyridyl)ethyl]-1,3,4,5,6,7,8,11,12,15,16,17,18,20,21,22,23,23a-octadecahydro-14H-pyrido[2,1-c][1,10,4] dioxazacycloicosine-1,7,14,17,18-pentaone.

23  (3R,4R,24aS)-8-allyl-4,10-dimethyl-3-[2-(3-pyridyl)ethyl]-1,3,4,5,6,7,8,11,12,14,15,16,17,18,19,21,22,23,24,24a-icosahydropyrido[2,1-c][1,11,4] dioxazacyclohenicosine-1,7,14,18,19-pentaone.

24  (3R,4R,25aS)-8-allyl-4,10-dimethyl-3-[2-(3-pyridyl)ethyl]-1,3,4,5,6,7,8,11,12,15,16,17,18,19,20,22,23,24,25, 25a-icosahydro-14H-pyrido[2,1c][1,12,4] dioxazacyclodocosine-1,7,14,19,20-pentaone.

32  (1R)-1-(3-benzoylphenyl)-3-phenylpropyl(1R)-2-(3,3-dimethyl-2-oxopentanoyl)cyclohexane-1-carboxylate.

33  (1R)-1-[3-(diallylcarbamoyl)phenyl]-3-phenylpropyl(1R)-2-(3,3-dimethyl-2-oxopentanoyl)cyclohexane-1-carboxylate.

35  ethyl1-(2-oxo-3-phenylpropanoyl)-2-piperidinecarboxylate.

36  ethyl1-pyruvoyl-2-piperidinecarboxylate.

37  ethyl1-(2-oxobutanoyl)-2-piperidinecarboxylate.

38  ethyl1-(3-methyl-2-oxobutanoyl)-2-piperidinecarboxylate.

39  ethyl1-(4-methyl-2-oxopentanoyl)-2-piperidinecarboxylate.

40  ethyl1-(3,3-dimethyl-2-oxobutanoyl)-2-piperidinecarboxylate.

41  ethyl1-(3,3-dimethyl-2-oxopentanoyl)-2-piperidinecarboxylate.

42  4-[2-(ethyloxycarbonyl)piperidino]-2,2-dimethyl-3,4-dioxobutyl acetate.

43  ethyl1-[2-(2-hydroxytetrahydro-2H-2-pyranyl)-2-oxoacetyl]-2-piperidinecarboxylate.

44  ethyl1-[2-(2-methoxytetrahydro-2H-2-pyranyl)-2-oxoacetyl]-2-piperidinecarboxylate.

45 ethyl1-[2-(1-hydroxycyclohexyl)-2-oxoacetyl]-2-piperidinecarboxylate.
46 ethyl1-[2-(1-methoxycyclohexyl)-2-oxoacetyl]-2-piperidinecarboxylate.
47 ethyl1-(2-cyclohexyl-2-oxoacetyl)-2-piperidinecarboxylate.
48 ethyl1-(2-oxo-2-piperidinoacetyl)-2-piperidinecarboxylate.
49 ethyl1-[2-(3,4-dihydro-2H-6-pyranyl)-2-oxoacetyl)-2-piperidinecarboxylate.
50 ethyl1-(2-oxo-2-phenylacetyl)-2-piperidinecarboxylate.
51 ethyl1-(4-methyl-2-oxo-1-thioxopentyl)-2-piperidinecarboxylate.
52 3-phenylpropyl1-(2-hydroxy-3,3-dimethylpentanoyl)-2-piperidinecarboxylate.
53 (1R)-1-phenyl-3-(3,4,5-trimethoxyphenyl)propyl1-(3,3-dimethylbutanoyl)-2-piperidinecarboxylate.
54 (1R)-1,3-diphenylpropyl1-(benzylsulfonyl)-2-piperidinecarboxylate.
55 3-(3,4,5-trimethoxyphenyl)propyl1-(benzylsulfonyl)-2-piperidinecarboxylate.
56 1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylic acid.
57 methyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2-pyranyl)-2-oxoacetyl)-2-piperidinecarboxylate.
58 isopropyl1-(2-[(2R,3R,6S))-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
59 benzyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxyylate.
60 1-phenylethyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
61 (Z)-3-phenyl-2-propenyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
62 3-(3,4-dimethoxyphenyl)propyl1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.
63 N2-benzyl-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate, and
64 N2-(3-phenylpropyl)-1-(2-[(2R,3R,6S)-6-[(2S,3E,5E,7E,9S,11R)-2,13-dimethoxy-3,9,11-trimethyl-12-oxo-3,5,7-tridecatrienyl]-2-hydroxy-3-methyltetrahydro-2H-2-pyranyl)-2-oxoacetyl)-2-piperidinecarboxylate.

33. The method of claim 27 wherein the non-immunosuppressive pipecolic acid derivative is administered orally.

34. The method of claim 27, wherein the non-immunosuppressive pipecolic acid derivative is selected from the group consisting of:

Compound 3–5

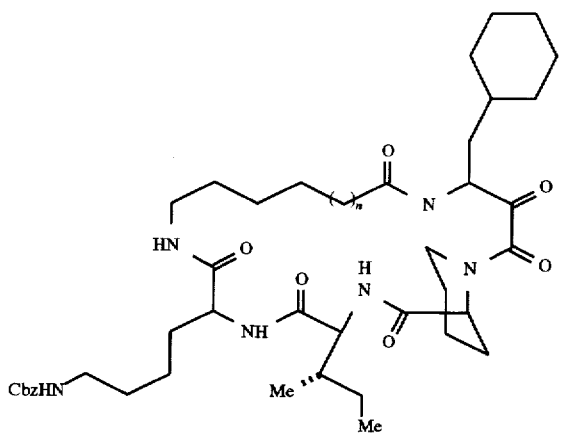

wherein n is 1, 2, or 3;

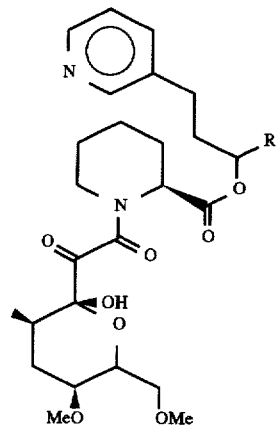

Compound 10;

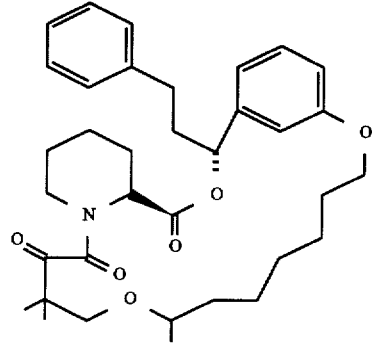

-continued
Compound 21;
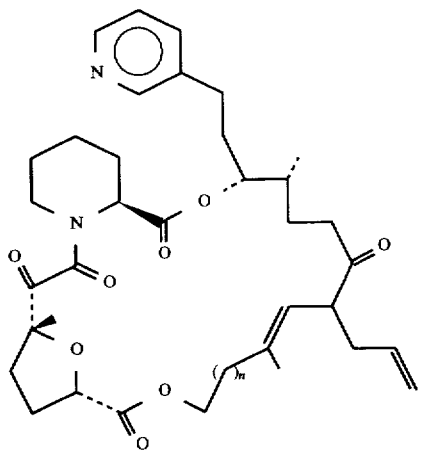
wherein n is 1, 2, or 3.
Compounds 25–27 ;
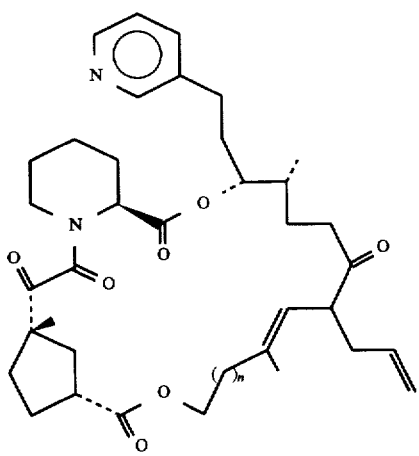
wherein n is 1, 2, or 3.
Compounds 28–30 ;
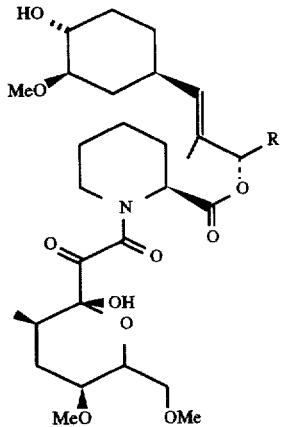
-continued
Compounds 28–30 ;
Compound 31 ;
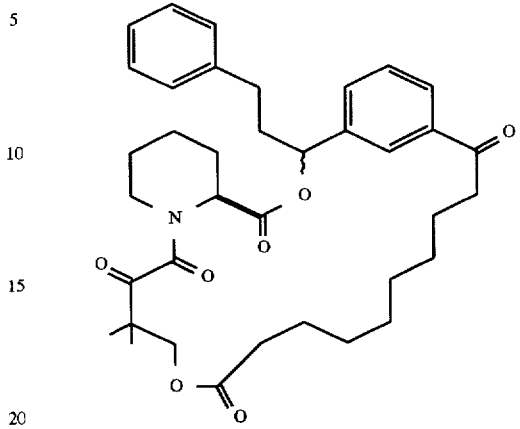
Compound 34;
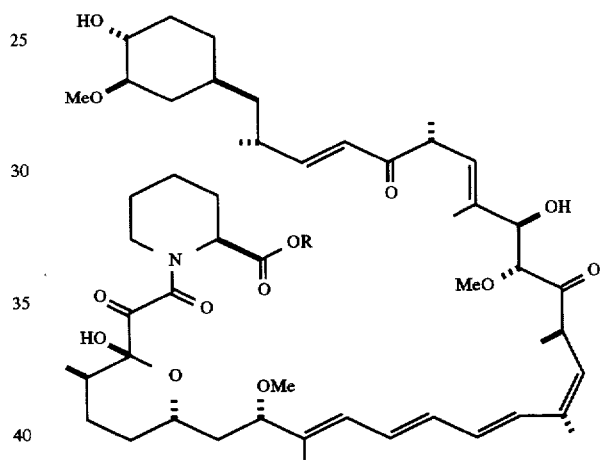
wherein R is Methyl (Me) or Benzyl (Bn).
Compounds 65 and 66;
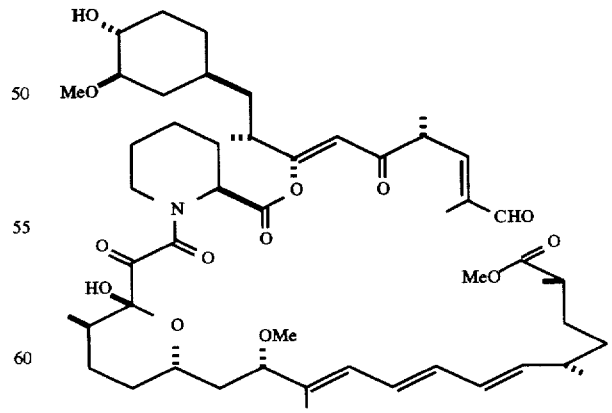

73

-continued

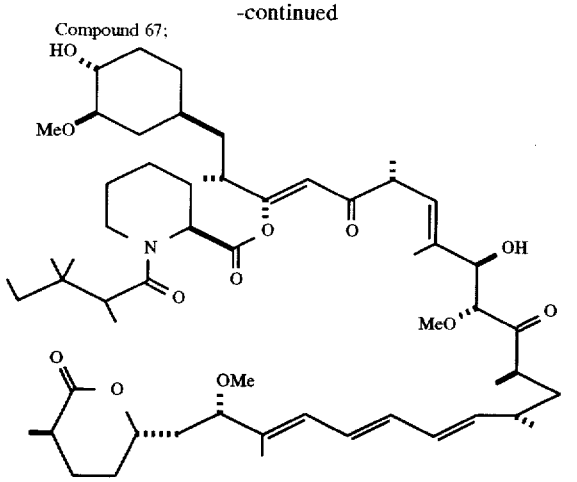

Compound 67;

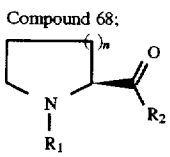

Compound 68;

wherein
n=2
$R_1$=

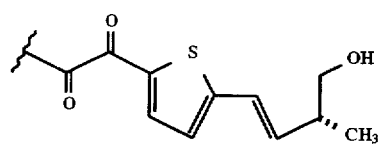

or

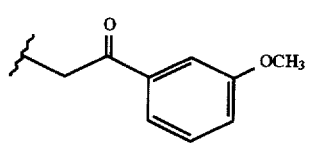

and
$R_2$=Phe-o-tert-butyl.

Compounds 69 and 70;

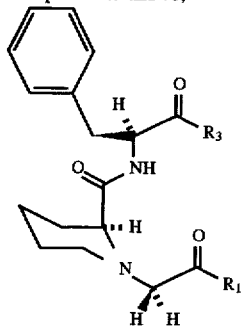

wherein
$R_1$=m-OCH$_3$Ph, $R_3$=Val-o-tert-butyl; Compound 71
$R_1$=m-OCH$_3$Ph, $R_3$=Leu-o-tert-butyl; Compound 72
$R_1$=m-OCH$_3$Ph, $R_3$=Ileu-o-tert-butyl; Compound 73
$R_1$=m-OCH$_3$Ph, $R_3$=hexahydro-Phe-o-tert-butyl; Cmpd 74

74

$R_1$=m-OCH$_3$Ph, $R_3$=allylalanine-o-tert-butyl; Cmpd 75
$R_1$=B-naphthyl, $R_3$=Val-o-tert-butyl; Compound 76

Compounds 71–76;

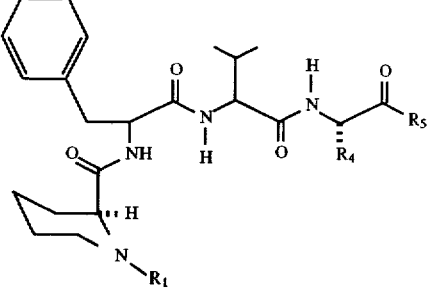

wherein
$R_1$=CH$_2$(CO)-m-OCH$_3$Ph (Compound 77)
$R_4$=CH$_2$Ph
$R_5$=OCH$_3$ or $R_1$=CH$_2$(CO)-B-naphthyl (Compound 78)
$R_4$=CH$_2$Ph
$R_5$=OCH$_3$ Compounds 77 and 78;

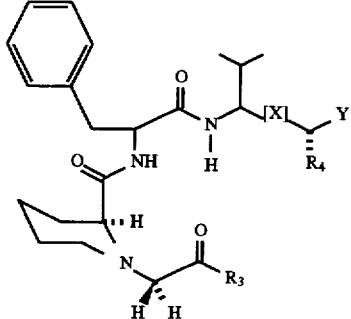

wherein
$R_1$=m-OCH$_3$Ph (Compound 79)
X=trans-CH=CH
$R_4$=H
Y=OC(o)Ph
$R_1$=m-OCH$_3$Ph (Compound 80)
X=trans-CH=CH
$R_4$=H
Y=OC(o)CF$_3$
$R_1$=m-OCH$_3$Ph (Compound 81)
X=trans-CH=CHI
$R_4$=—
Y=—
$R_1$=m-OCH$_3$Ph (Compound 82)
X=trans-CH=CH
$R_4$=H
Y=OCH$_2$CH=CH$_2$
$R_1$=m-OCH$_3$Ph (Compound 83)

X=C=O
R₄=H
Y=Ph
Compounds 79-83;
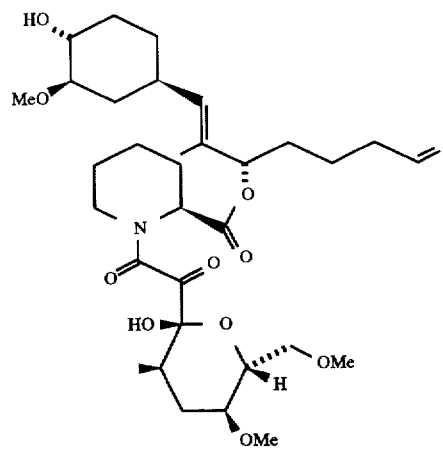
-continued
Compound 85;
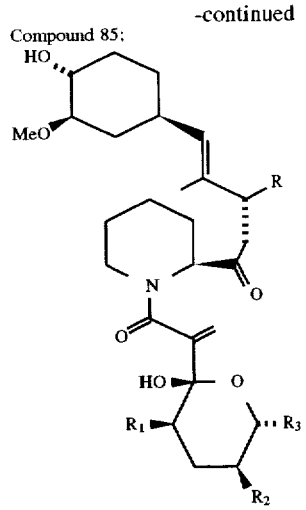
wherein
$R_1$=H, $R_2$=OMe, and $R_3$=CH$_2$OMe (Compound 86);
$R_1$=H, $R_2$=H, and $R_3$=H (Compound 87); and
$R_1$=Me, $R_2$=H, and $R_3$=H (Compound 8 8).
\* \* \* \* \*

UNITED STATES PATENT AND TRADEMARK OFFICE
CERTIFICATE OF CORRECTION

PATENT NO. : 5,798,355
DATED : August 25, 1998
INVENTOR(S) : Steiner et al.

It is certified that error appears in the above-identified patent and that said Letters Patent is hereby corrected as shown below:

Column 1, line 4, please insert
--GOVERNMENT RIGHTS
This invention was supported by grants from the United States government, namely Grant Nos. MH-18501, DA00266, and DA00074, from the USPHS. Accordingly, the government may have certain rights in this invention.--

Signed and Sealed this

Thirteenth Day of April, 1999

Attest:

Q. TODD DICKINSON

*Attesting Officer*  Acting Commissioner of Patents and Trademarks